(12) United States Patent
Shelton, IV et al.

(10) Patent No.: US 7,464,846 B2
(45) Date of Patent: Dec. 16, 2008

(54) SURGICAL INSTRUMENT HAVING A REMOVABLE BATTERY

(75) Inventors: Frederick E. Shelton, IV, New Vienna, OH (US); Kevin R. Doll, Mason, OH (US); Jeffrey S. Swayze, Hamilton, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/344,020

(22) Filed: Jan. 31, 2006

(65) Prior Publication Data

US 2007/0175960 A1  Aug. 2, 2007

(51) Int. Cl.
  *A61B 17/14* (2006.01)
(52) U.S. Cl. .................................. 227/175.1; 227/19
(58) Field of Classification Search ............... 227/19, 227/175.1; 173/217
  See application file for complete search history.

(56) References Cited

U.S. PATENT DOCUMENTS

| | | | |
|---|---|---|---|
| 2,037,727 A | 4/1936 | Chapelle | |
| 3,269,630 A | 8/1966 | Flelscher | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,734,207 A * | 5/1973 | Fishbein | 173/217 |
| 3,819,100 A | 6/1974 | Noiles et al. | |
| 3,892,228 A | 7/1975 | Mitsul | |
| 3,894,174 A | 7/1975 | Cartun | |
| 3,940,844 A | 3/1976 | Colby et al. | |
| 4,213,562 A | 7/1980 | Garrett et al. | |
| 4,331,277 A | 5/1982 | Green | |
| 4,349,028 A | 9/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,442,964 A | 4/1984 | Becht | |
| 4,475,679 A | 10/1984 | Fleury, Jr. | |
| 4,500,024 A | 2/1985 | DiGiovanni et al. | |

(Continued)

FOREIGN PATENT DOCUMENTS

CA  2458946 A1  3/2003

(Continued)

OTHER PUBLICATIONS

European Search Report, Application No. 07250372.5, dated May 24, 2007 (4 pages).

(Continued)

*Primary Examiner*—Brian D. Nash

(57) ABSTRACT

A surgical instrument. The surgical instrument comprises a handle, a battery, a motor, and a lockout system. The handle comprises a primary portion and a grip portion. The grip portion is releasably connected to the primary portion. The battery is within the grip portion. The motor is in electrical communication with the battery. The lockout system is within the handle, and is structured and arranged to block connection of the grip portion to the primary portion after the grip portion is disconnected from the primary portion a predetermined number of times.

10 Claims, 51 Drawing Sheets

U.S. PATENT DOCUMENTS

| | | |
|---|---|---|
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,606,343 A | 8/1986 | Conta et al. |
| 4,608,981 A | 9/1986 | Rothfuss et al. |
| 4,610,383 A | 9/1986 | Rothfuss et al. |
| 4,629,107 A | 12/1986 | Fedotov et al. |
| 4,671,445 A | 6/1987 | Barker et al. |
| 4,709,120 A | 11/1987 | Pearson |
| 4,715,520 A | 12/1987 | Roehr, Jr. et al. |
| 4,728,020 A | 3/1988 | Green et al. |
| 4,728,876 A | 3/1988 | Mongeon et al. |
| 4,729,260 A | 3/1988 | Dudden |
| 4,754,909 A | 7/1988 | Barker et al. |
| 4,767,044 A | 8/1988 | Green |
| 4,790,225 A | 12/1988 | Moody et al. |
| 4,821,939 A | 4/1989 | Green |
| 4,869,414 A | 9/1989 | Green et al. |
| 4,869,415 A | 9/1989 | Fox |
| 4,880,015 A | 11/1989 | Nierman |
| 4,892,244 A | 1/1990 | Fox et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 5,027,834 A | 7/1991 | Pruitt |
| 5,031,814 A | 7/1991 | Tompkins et al. |
| 5,040,715 A | 8/1991 | Green et al. |
| 5,061,269 A | 10/1991 | Muller |
| 5,065,929 A | 11/1991 | Schulze et al. |
| 5,080,556 A | 1/1992 | Carreno |
| 5,084,057 A | 1/1992 | Green et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,156,315 A | 10/1992 | Green et al. |
| 5,171,247 A | 12/1992 | Hughett et al. |
| 5,171,249 A | 12/1992 | Stefanchik et al. |
| 5,200,280 A * | 4/1993 | Karasa .................. 429/65 |
| 5,207,697 A * | 5/1993 | Carusillo et al. ............ 606/167 |
| 5,211,649 A | 5/1993 | Kohler et al. |
| 5,221,036 A | 6/1993 | Takase |
| 5,240,163 A | 8/1993 | Stein et al. |
| 5,246,156 A | 9/1993 | Rothfuss et al. |
| 5,253,793 A | 10/1993 | Green et al. |
| RE34,519 E | 1/1994 | Fox et al. |
| 5,275,323 A | 1/1994 | Schulze et al. |
| 5,307,976 A | 5/1994 | Olson et al. |
| 5,309,927 A | 5/1994 | Welch |
| 5,318,221 A | 6/1994 | Green et al. |
| 5,330,502 A | 7/1994 | Hassler et al. |
| 5,332,142 A | 7/1994 | Robinson et al. |
| 5,339,799 A | 8/1994 | Kami et al. |
| 5,350,400 A | 9/1994 | Esposito et al. |
| 5,379,933 A | 1/1995 | Green et al. |
| 5,383,880 A | 1/1995 | Hooven |
| 5,383,881 A | 1/1995 | Green et al. |
| 5,389,098 A | 2/1995 | Tsuruta et al. |
| 5,391,180 A | 2/1995 | Tovey et al. |
| 5,395,033 A | 3/1995 | Byrne et al. |
| 5,395,312 A | 3/1995 | Desai |
| 5,397,046 A | 3/1995 | Savage et al. |
| 5,403,312 A | 4/1995 | Yates et al. |
| 5,405,344 A | 4/1995 | Williamson et al. |
| 5,409,498 A | 4/1995 | Braddock et al. |
| 5,413,267 A | 5/1995 | Solyntjes et al. |
| 5,413,268 A | 5/1995 | Green et al. |
| 5,415,335 A | 5/1995 | Knodell, Jr. |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,445,304 A | 8/1995 | Plyley et al. |
| 5,447,513 A | 9/1995 | Davison et al. |
| 5,449,365 A | 9/1995 | Green et al. |
| 5,456,401 A | 10/1995 | Green et al. |
| 5,458,579 A | 10/1995 | Chodorow et al. |
| 5,462,215 A | 10/1995 | Viola et al. |
| 5,465,895 A | 11/1995 | Knodel et al. |
| 5,465,896 A | 11/1995 | Allen et al. |
| 5,467,911 A | 11/1995 | Tsuruta et al. |
| 5,470,006 A | 11/1995 | Rodak |
| 5,472,132 A | 12/1995 | Savage et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,518,163 A | 5/1996 | Hooven |
| 5,518,164 A | 5/1996 | Hooven |
| 5,522,817 A | 6/1996 | Sander et al. |
| 5,527,320 A | 6/1996 | Carruthers et al. |
| 5,529,235 A | 6/1996 | Boiarski et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 4,605,001 A | 8/1996 | Rothfuss et al. |
| 5,547,117 A | 8/1996 | Hamblin et al. |
| 5,549,628 A | 8/1996 | Cooper et al. |
| 5,553,675 A * | 9/1996 | Pitzen et al. ................. 173/217 |
| 5,554,169 A | 9/1996 | Green et al. |
| 5,558,665 A | 9/1996 | Kieturakis |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,574,431 A | 11/1996 | McKeown et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,597,107 A | 1/1997 | Knodel et al. |

| | | | | | | |
|---|---|---|---|---|---|---|
| 5,601,224 A | 2/1997 | Bishop et al. | | 5,797,536 A | 8/1998 | Smith et al. |
| 5,603,443 A | 2/1997 | Clark et al. | | 5,797,537 A | 8/1998 | Oberlin et al. |
| 5,605,272 A | 2/1997 | Witt et al. | | 5,797,538 A | 8/1998 | Heaton et al. |
| 5,605,273 A | 2/1997 | Hamblin et al. | | 5,799,857 A | 9/1998 | Robertson et al. |
| 5,607,094 A | 3/1997 | Clark et al. | | 5,807,393 A | 9/1998 | Williamson, IV et al. |
| 5,607,095 A | 3/1997 | Smith et al. | | 5,810,811 A | 9/1998 | Yates et al. |
| 5,609,285 A | 3/1997 | Grant et al. | | 5,817,093 A | 10/1998 | Williamson, IV et al. |
| 5,626,587 A | 5/1997 | Bishop et al. | | 5,817,109 A | 10/1998 | McGarry et al. |
| 5,628,446 A | 5/1997 | Geiste et al. | | 5,817,119 A | 10/1998 | Klieman et al. |
| 5,630,539 A | 5/1997 | Plyley et al. | | 5,820,009 A | 10/1998 | Melling et al. |
| 5,630,540 A | 5/1997 | Blewett | | 5,823,066 A | 10/1998 | Huitema et al. |
| 5,632,432 A | 5/1997 | Schulze et al. | | 5,826,776 A | 10/1998 | Schulze et al. |
| 5,634,584 A | 6/1997 | Okorocha et al. | | 5,829,662 A | 11/1998 | Allen et al. |
| 5,636,779 A | 6/1997 | Palmer | | 5,833,690 A | 11/1998 | Yates et al. |
| 5,636,780 A | 6/1997 | Green et al. | | 5,836,503 A | 11/1998 | Ehrenfels et al. |
| 5,639,008 A | 6/1997 | Gallagher et al. | | 5,836,960 A | 11/1998 | Kolesa et al. |
| 5,643,291 A | 7/1997 | Pier et al. | | 5,839,639 A | 11/1998 | Sauer et al. |
| 5,645,209 A | 7/1997 | Green et al. | | 5,843,132 A * | 12/1998 | Ilvento ........................ 607/10 |
| 5,647,526 A | 7/1997 | Green et al. | | 5,855,311 A | 1/1999 | Hamblin et al. |
| 5,651,491 A | 7/1997 | Heaton et al. | | 5,865,361 A | 2/1999 | Milliman et al. |
| 5,653,373 A | 8/1997 | Green et al. | | 5,871,135 A | 2/1999 | Williamson IV et al. |
| 5,653,374 A | 8/1997 | Young et al. | | 5,873,885 A | 2/1999 | Weidenbenner |
| 5,655,698 A | 8/1997 | Yoon | | 5,878,937 A | 3/1999 | Green et al. |
| 5,657,921 A | 8/1997 | Young et al. | | 5,878,938 A | 3/1999 | Bittner et al. |
| 5,658,300 A | 8/1997 | Bito et al. | | 5,893,506 A | 4/1999 | Powell |
| 5,662,258 A | 9/1997 | Knodel et al. | | 5,894,979 A | 4/1999 | Powell |
| 5,662,260 A | 9/1997 | Yoon | | 5,901,895 A | 5/1999 | Heaton et al. |
| 5,662,662 A | 9/1997 | Bishop et al. | | 5,906,625 A | 5/1999 | Bito et al. |
| 5,667,517 A | 9/1997 | Hooven | | 5,911,353 A | 6/1999 | Bolanos et al. |
| 5,669,544 A | 9/1997 | Schulze et al. | | 5,915,616 A | 6/1999 | Viola et al. |
| 5,673,840 A | 10/1997 | Schulze et al. | | 5,918,791 A | 7/1999 | Sorrentino et al. |
| 5,673,841 A | 10/1997 | Schulze et al. | | 5,931,853 A | 8/1999 | McEwen et al. |
| 5,673,842 A | 10/1997 | Bittner et al. | | 5,938,667 A | 8/1999 | Peyser et al. |
| 5,678,748 A | 10/1997 | Plyley et al. | | 5,941,442 A | 8/1999 | Geiste et al. |
| 5,680,981 A | 10/1997 | Mililli et al. | | 5,951,552 A | 9/1999 | Long et al. |
| 5,680,982 A | 10/1997 | Schulze et al. | | 5,951,574 A | 9/1999 | Stefanchik et al. |
| 5,680,983 A | 10/1997 | Plyley et al. | | 5,954,259 A | 9/1999 | Viola et al. |
| 5,685,474 A | 11/1997 | Seeber | | 5,988,479 A | 11/1999 | Palmer |
| 5,688,270 A | 11/1997 | Yates et al. | | 6,010,054 A | 1/2000 | Johnson et al. |
| 5,690,269 A | 11/1997 | Bolanos et al. | | 6,017,356 A | 1/2000 | Frederick et al. |
| 5,692,668 A | 12/1997 | Schulze et al. | | 6,022,352 A | 2/2000 | Vandewalle |
| 5,693,042 A | 12/1997 | Boiarski et al. | | 6,024,741 A | 2/2000 | Williamson, IV et al. |
| 5,697,543 A | 12/1997 | Burdorff | | 6,024,748 A | 2/2000 | Manzo et al. |
| 5,700,270 A | 12/1997 | Peyser et al. | | 6,032,849 A | 3/2000 | Mastri et al. |
| 5,702,408 A | 12/1997 | Wales et al. | | 6,079,606 A | 6/2000 | Milliman et al. |
| 5,704,534 A | 1/1998 | Huitema et al. | | 6,082,577 A | 7/2000 | Coates et al. |
| 5,706,997 A | 1/1998 | Green et al. | | 6,083,234 A | 7/2000 | Nicholas et al. |
| 5,706,998 A | 1/1998 | Plyley et al. | | 6,099,537 A | 8/2000 | Sugai et al. |
| 5,709,334 A | 1/1998 | Sorrentino et al. | | 6,102,271 A | 8/2000 | Longo et al. |
| 5,709,680 A | 1/1998 | Yates et al. | | 6,109,500 A | 8/2000 | Alli et al. |
| 5,711,472 A | 1/1998 | Bryan | | H1904 H | 10/2000 | Yates et al. |
| 5,713,505 A | 2/1998 | Huitema | | 6,126,670 A * | 10/2000 | Walker et al. ................ 606/176 |
| 5,715,988 A | 2/1998 | Palmer | | 6,131,789 A | 10/2000 | Schulze et al. |
| 5,718,359 A | 2/1998 | Palmer et al. | | 6,155,473 A | 12/2000 | Tompkins et al. |
| 5,732,871 A | 3/1998 | Clark et al. | | 6,156,056 A | 12/2000 | Kearns et al. |
| 5,735,445 A | 4/1998 | Vidal et al. | | 6,162,208 A | 12/2000 | Hipps |
| 5,743,456 A | 4/1998 | Jones et al. | | 6,202,914 B1 | 3/2001 | Geiste et al. |
| 5,747,953 A * | 5/1998 | Philipp ........................ 318/139 | | 6,223,835 B1 * | 5/2001 | Habedank et al. ........... 173/217 |
| 5,749,893 A | 5/1998 | Vidal et al. | | 6,241,139 B1 | 6/2001 | Milliman et al. |
| 5,752,644 A | 5/1998 | Bolanos et al. | | 6,250,532 B1 | 6/2001 | Green et al. |
| 5,758,814 A | 6/1998 | Gallagher et al. | | 6,264,086 B1 | 7/2001 | McGuckin, Jr. |
| 5,762,255 A | 6/1998 | Chrisman et al. | | 6,264,087 B1 | 7/2001 | Whitman |
| 5,762,256 A | 6/1998 | Mastri et al. | | 6,273,897 B1 | 8/2001 | Dalessandro et al. |
| 5,779,130 A | 7/1998 | Alesi et al. | | 6,309,403 B1 | 10/2001 | Minor et al. |
| 5,779,132 A | 7/1998 | Knodel et al. | | 6,315,184 B1 | 11/2001 | Whitman |
| 5,782,396 A | 7/1998 | Mastri et al. | | 6,320,123 B1 | 11/2001 | Reimers |
| 5,782,397 A * | 7/1998 | Koukline ................ 227/176.1 | | 6,325,810 B1 | 12/2001 | Hamilton et al. |
| 5,782,749 A | 7/1998 | Riza | | 6,330,965 B1 | 12/2001 | Milliman et al. |
| 5,782,859 A | 7/1998 | Nicholas et al. | | 6,358,224 B1 | 3/2002 | Tims et al. |
| 5,785,232 A | 7/1998 | Vidal et al. | | 6,416,486 B1 | 7/2002 | Wampler |
| 5,792,165 A | 8/1998 | Klieman et al. | | 6,443,973 B1 | 9/2002 | Whitman |
| 5,794,834 A | 8/1998 | Hamblin et al. | | 6,488,197 B1 | 12/2002 | Whitman |
| 5,796,188 A * | 8/1998 | Bays ........................ 310/50 | | 6,491,201 B1 | 12/2002 | Whitman |

| | | | | | |
|---|---|---|---|---|---|
| 6,503,257 B2 | 1/2003 | Grant et al. | 7,111,769 B2 | 9/2006 | Wales et al. |
| 6,505,768 B2 | 1/2003 | Whitman | 7,114,642 B2 | 10/2006 | Whitman |
| 6,511,468 B1 | 1/2003 | Cragg et al. | 7,128,253 B2 | 10/2006 | Mastri et al. |
| 6,522,101 B2 | 2/2003 | Malackowski | 7,128,254 B2 | 10/2006 | Shelton, IV et al. |
| 6,550,546 B2 | 4/2003 | Thurler et al. | 7,140,527 B2 | 11/2006 | Ehrenfels et al. |
| 6,592,597 B2 | 7/2003 | Grant et al. | 7,143,924 B2 | 12/2006 | Scirica et al. |
| 6,602,252 B2 | 8/2003 | Mollenauer | 7,143,925 B2 | 12/2006 | Shelton, IV et al. |
| 6,619,529 B2 | 9/2003 | Green et al. | 7,143,926 B2 | 12/2006 | Shelton, IV et al. |
| 6,620,166 B1 | 9/2003 | Wenstrom, Jr. et al. | 7,159,750 B2 | 1/2007 | Racenet et al. |
| 6,629,988 B2 | 10/2003 | Weadock | 7,168,604 B2 | 1/2007 | Milliman et al. |
| 6,644,532 B2 | 11/2003 | Green et al. | 7,188,758 B2 | 3/2007 | Viola et al. |
| 6,656,193 B2 | 12/2003 | Grant et al. | 7,207,471 B2 | 4/2007 | Heinrich et al. |
| 6,669,073 B2 | 12/2003 | Milliman et al. | 7,207,472 B2 | 4/2007 | Wukusick et al. |
| 6,681,978 B2 | 1/2004 | Geiste et al. | 7,210,609 B2 | 5/2007 | Leiboff et al. |
| 6,681,979 B2 | 1/2004 | Whitman | 7,225,964 B2 | 6/2007 | Mastri et al. |
| 6,695,199 B2 | 2/2004 | Whitman | 7,246,734 B2 | 7/2007 | Shelton, IV |
| 6,698,643 B2 | 3/2004 | Whitman | 7,258,262 B2 | 8/2007 | Mastri et al. |
| 6,705,503 B1 | 3/2004 | Pedicini et al. | 7,398,908 B2 | 7/2008 | Holsten et al. |
| 6,716,232 B1 | 4/2004 | Vidal et al. | 2002/0117534 A1 | 8/2002 | Green et al. |
| 6,716,233 B1 | 4/2004 | Whitman | 2002/0165541 A1 | 11/2002 | Whitman |
| 6,752,816 B2 | 6/2004 | Culp et al. | 2003/0105478 A1 | 6/2003 | Whitman et al. |
| 6,755,338 B2 | 6/2004 | Hahnen et al. | 2003/0130677 A1 | 7/2003 | Whitman et al. |
| 6,773,438 B1 | 8/2004 | Knodel et al. | 2003/0216778 A1 | 11/2003 | Weadock |
| 6,786,382 B1 | 9/2004 | Hoffman | 2004/0028502 A1 | 2/2004 | Cummins |
| 6,793,652 B1 | 9/2004 | Whitman et al. | 2004/0094597 A1 | 5/2004 | Whitman et al. |
| 6,805,273 B2 | 10/2004 | Bilotti et al. | 2004/0097987 A1 | 5/2004 | Pugsley et al. |
| 6,806,808 B1 | 10/2004 | Watters et al. | 2004/0108357 A1 | 6/2004 | Milliman et al. |
| 6,814,741 B2 | 11/2004 | Bowman et al. | 2004/0111081 A1 | 6/2004 | Whitman et al. |
| 6,817,508 B1 | 11/2004 | Racenet et al. | 2004/0116952 A1 | 6/2004 | Sakurai et al. |
| 6,817,509 B2 | 11/2004 | Geiste et al. | 2004/0122471 A1 | 6/2004 | Toby et al. |
| 6,821,273 B2 | 11/2004 | Mollenauer | 2004/0164123 A1 | 8/2004 | Racenet et al. |
| 6,828,902 B2 | 12/2004 | Casden | 2004/0167572 A1 | 8/2004 | Roth et al. |
| 6,830,174 B2 | 12/2004 | Hillstead et al. | 2004/0173659 A1 | 9/2004 | Green et al. |
| 6,835,199 B2 | 12/2004 | McGuckin, Jr. et al. | 2004/0222268 A1 | 11/2004 | Bilotti et al. |
| 6,843,403 B2 | 1/2005 | Whitman | 2004/0230214 A1 | 11/2004 | Donofrio et al. |
| 6,846,307 B2 | 1/2005 | Whitman et al. | 2004/0232199 A1 | 11/2004 | Shelton, IV et al. |
| 6,846,308 B2 | 1/2005 | Whitman et al. | 2004/0232201 A1 | 11/2004 | Wenchell et al. |
| 6,846,309 B2 | 1/2005 | Whitman et al. | 2004/0243151 A1 | 12/2004 | Demmy et al. |
| 6,849,071 B2 | 2/2005 | Whitman et al. | 2004/0243176 A1 | 12/2004 | Hahnen et al. |
| RE38,708 E | 3/2005 | Bolanos et al. | 2005/0006434 A1 | 1/2005 | Wales et al. |
| 6,877,647 B2 | 4/2005 | Green et al. | 2005/0021026 A1 | 1/2005 | Baily |
| 6,905,057 B2 | 6/2005 | Swayze et al. | 2005/0023324 A1 | 2/2005 | Doll et al. |
| 6,945,444 B2 | 9/2005 | Gresham et al. | 2005/0033357 A1 | 2/2005 | Braun |
| 6,953,138 B1 | 10/2005 | Dworak et al. | 2005/0070925 A1 | 3/2005 | Shelton, IV et al. |
| 6,953,139 B2 | 10/2005 | Milliman et al. | 2005/0070958 A1 | 3/2005 | Swayze et al. |
| 6,959,852 B2 | 11/2005 | Shelton, IV et al. | 2005/0072827 A1 | 4/2005 | Mollenauer |
| 6,964,363 B2 | 11/2005 | Wales et al. | 2005/0103819 A1 | 5/2005 | Racenet et al. |
| 6,978,921 B2 | 12/2005 | Shelton, IV et al. | 2005/0107824 A1 | 5/2005 | Hillstead et al. |
| 6,978,922 B2 | 12/2005 | Bilotti et al. | 2005/0119669 A1 | 6/2005 | Demmy |
| 6,981,628 B2 | 1/2006 | Wales | 2005/0125009 A1 | 6/2005 | Perry et al. |
| 6,981,941 B2 | 1/2006 | Whitman et al. | 2005/0131390 A1 | 6/2005 | Heinrich et al. |
| 6,986,451 B1 | 1/2006 | Mastri et al. | 2005/0143759 A1 | 6/2005 | Kelly |
| 6,988,649 B2 | 1/2006 | Shelton, IV et al. | 2005/0145671 A1 | 7/2005 | Viola |
| 6,988,650 B2 | 1/2006 | Schwemberger et al. | 2005/0165415 A1 | 7/2005 | Wales |
| 7,000,818 B2 | 2/2006 | Shelton, IV et al. | 2005/0171522 A1 | 8/2005 | Christopherson |
| 7,000,819 B2 | 2/2006 | Swayze et al. | 2005/0173490 A1 | 8/2005 | Shelton, IV |
| 7,032,798 B2 | 4/2006 | Whitman et al. | 2005/0184121 A1 | 8/2005 | Heinrich |
| 7,032,799 B2 | 4/2006 | Viola et al. | 2005/0187576 A1 | 8/2005 | Whitman et al. |
| 7,036,680 B1 | 5/2006 | Flannery | 2005/0189397 A1 | 9/2005 | Jankowski |
| 7,044,352 B2 | 5/2006 | Shelton, IV et al. | 2005/0192609 A1 | 9/2005 | Whitman et al. |
| 7,044,353 B2 | 5/2006 | Mastri et al. | 2005/0203550 A1 | 9/2005 | Laufer et al. |
| 7,048,687 B1 | 5/2006 | Reuss et al. | 2005/0216055 A1 | 9/2005 | Scirica et al. |
| 7,055,730 B2 | 6/2006 | Ehrenfels et al. | 2005/0230453 A1 | 10/2005 | Viola |
| 7,055,731 B2 | 6/2006 | Shelton, IV et al. | 2005/0263562 A1 | 12/2005 | Shelton, IV et al. |
| 7,059,508 B2 | 6/2006 | Shelton, IV et al. | 2005/0263563 A1 | 12/2005 | Racenet et al. |
| 7,066,944 B2 | 6/2006 | Laufer et al. | 2005/0274768 A1 | 12/2005 | Cummins et al. |
| 7,070,083 B2 | 7/2006 | Jankowski | 2006/0008787 A1 | 1/2006 | Hayman et al. |
| 7,077,856 B2 | 7/2006 | Whitman | 2006/0011699 A1 | 1/2006 | Olson et al. |
| 7,083,075 B2 | 8/2006 | Swayze et al. | 2006/0025811 A1 | 2/2006 | Shelton, IV |
| 7,090,673 B2 | 8/2006 | Dycus et al. | 2006/0025812 A1 | 2/2006 | Shelton, IV |
| 7,090,684 B2 | 8/2006 | McGuckin, Jr. et al. | 2006/0025813 A1 | 2/2006 | Shelton et al. |
| 7,097,089 B2 | 8/2006 | Marczyk | 2006/0025816 A1 | 2/2006 | Shelton |
| 7,098,794 B2 | 8/2006 | Lindsay et al. | 2006/0047303 A1 | 3/2006 | Ortiz et al. |

| | | |
|---|---|---|
| 2006/0047308 A1 | 3/2006 | Ortiz et al. |
| 2006/0049229 A1 | 3/2006 | Milliman et al. |
| 2006/0060630 A1 | 3/2006 | Shelton, IV et al. |
| 2006/0087442 A1 | 4/2006 | Smith et al. |
| 2006/0097026 A1 | 5/2006 | Shelton, IV |
| 2006/0100643 A1 | 5/2006 | Laufer et al. |
| 2006/0108393 A1 | 5/2006 | Heinrich et al. |
| 2006/0122636 A1 | 6/2006 | Bailley et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2006/0190029 A1 | 8/2006 | Wales |
| 2006/0190031 A1 | 8/2006 | Wales et al. |
| 2006/0226196 A1 | 10/2006 | Hueil et al. |
| 2006/0229665 A1 | 10/2006 | Wales et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0027469 A1 | 2/2007 | Smith et al. |
| 2007/0034666 A1 | 2/2007 | Holsten et al. |
| 2007/0034668 A1 | 2/2007 | Holsten et al. |
| 2007/0045379 A1 | 3/2007 | Shelton |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Oritz et al. |
| 2007/0102476 A1 | 5/2007 | Shelton, IV et al. |
| 2007/0106317 A1 | 5/2007 | Shelton, IV et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 9412228 U | 9/1994 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0033548 B1 | 5/1986 |
| EP | 0639349 A2 | 2/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0669104 A1 | 8/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0770355 A1 | 5/1997 |
| EP | 0503662 B1 | 6/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0667119 B1 | 7/1998 |
| EP | 0603472 B1 | 11/1998 |
| EP | 0878169 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0705570 B1 | 4/2004 |

| | | | |
|---|---|---|---|
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1621141 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1300117 B1 | 8/2007 |
| FR | 1112936 A | 3/1956 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/29639 A1 | 11/1995 |
| WO | WO 96/35464 A1 | 11/1996 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 00/057796 A1 | 10/2000 |
| WO | WO 00/72762 A1 | 12/2000 |
| WO | WO 00/72765 A1 | 12/2000 |
| WO | WO 01/05702 A1 | 1/2001 |
| WO | WO 01/010482 A1 | 2/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/30297 A2 | 4/2002 |
| WO | WO 02/32322 A2 | 4/2002 |
| WO | WO 02/043571 A2 | 6/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094747 A1 | 11/2003 |
| WO | WO 2003/094746 A1 | 11/2003 |
| WO | WO 03/101313 A1 | 12/2003 |
| WO | WO 03/105702 A2 | 12/2003 |
| WO | WO 2004/006980 A2 | 1/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |

OTHER PUBLICATIONS

European Search Report, Application No. 07250372.5, dated Aug. 13, 2007 (9 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

\* cited by examiner

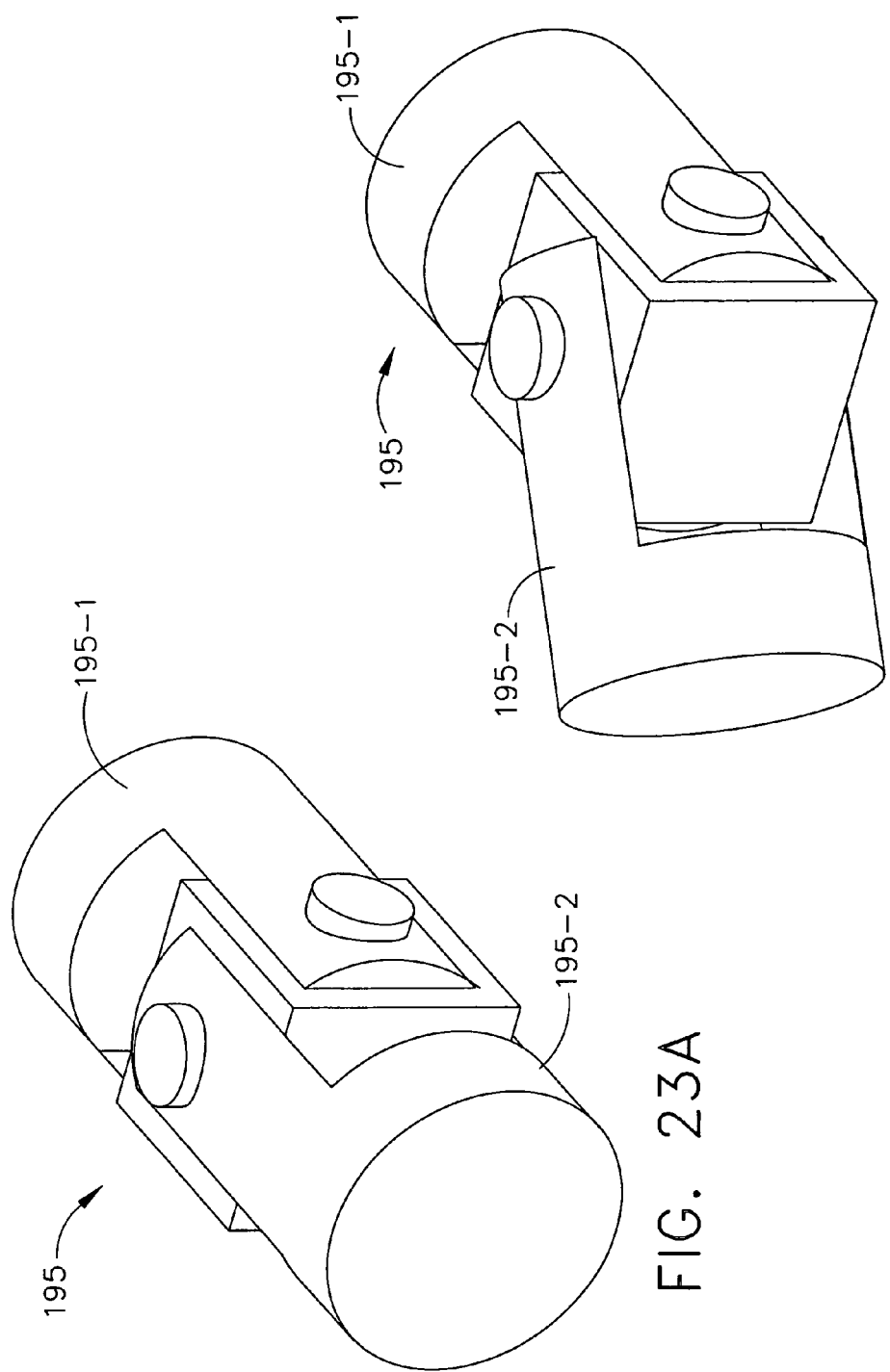

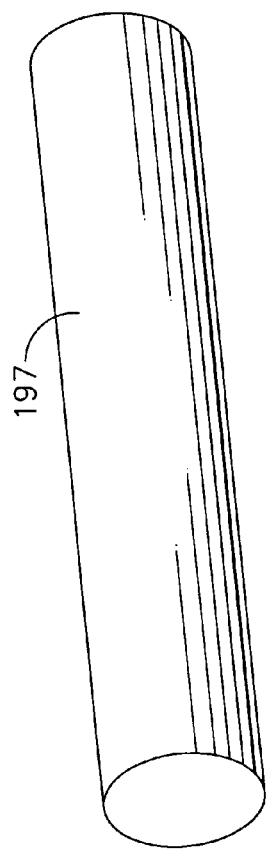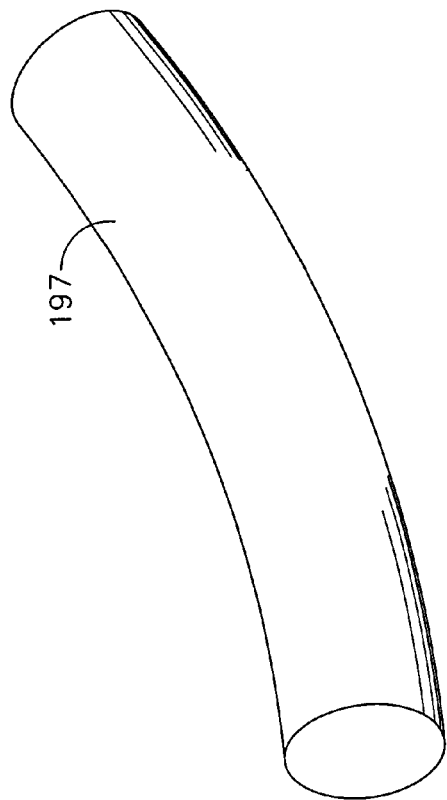

SURGICAL INSTRUMENT HAVING A REMOVABLE BATTERY

CROSS-REFERENCE TO RELATED APPLICATIONS

This application is related to the following concurrently-filed U.S. patent applications, which are incorporated herein by reference:

(1) MOTOR-DRIVEN SURGICAL CUTTING AND FASTENING INSTRUMENT WITH USER FEEDBACK SYSTEM; Inventors: Frederick E. Shelton, IV, John Ouwerkerk and Jerome R. Morgan (K&LNG 050519/END5687USNP);

(2) MOTOR-DRIVEN SURGICAL CUTTING AND FASTENING INSTRUMENT WITH LOADING FORCE FEEDBACK; Inventors: Frederick E. Shelton, IV, John N. Ouwerkerk, Jerome R. Morgan, and Jeffrey S. Swayze (K&LNG 050516/END5692USNP);

(3) MOTOR-DRIVEN SURGICAL CUTTING AND FASTENING INSTRUMENT WITH TACTILE POSITION FEEDBACK; Inventors: Frederick E. Shelton, IV, John N. Ouwerkerk, Jerome R. Morgan, and Jeffrey S. Swayze (K&LNG 050515/END5693USNP);

(4) MOTOR-DRIVEN SURGICAL CUTTING AND FASTENING INSTRUMENT WITH ADAPTIVE USER FEEDBACK; Inventors: Frederick E. Shelton, IV, John N. Ouwerkerk, and Jerome R. Morgan (K&LNG 050513/END5694USNP);

(5) MOTOR-DRIVEN SURGICAL CUTTING AND FASTENING INSTRUMENT WITH ARTICULATABLE END EFFECTOR; Inventors: Frederick E. Shelton, IV and Christoph L. Gillum (K&LNG 050692/END5769USNP);

(6) MOTOR-DRIVEN SURGICAL CUTTING AND FASTENING INSTRUMENT WITH MECHANICAL CLOSURE SYSTEM; Inventors: Frederick E. Shelton, IV and Christoph L. Gillum (K&LNG 050693/END5770USNP);

(7) SURGICAL CUTTING AND FASTENING INSTRUMENT WITH CLOSURE TRIGGER LOCKING MECHANISM; Inventors: Frederick E. Shelton, IV and Kevin R. Doll (K&LNG 050694/END5771USNP);

(8) GEARING SELECTOR FOR A POWERED SURGICAL CUTTING AND FASTENING STAPLING INSTRUMENT; Inventors: Frederick E. Shelton, IV, Jeffrey S. Swayze, Eugene L. Timperman (K&LNG 050697/END5772USNP);

(9) SURGICAL INSTRUMENT HAVING RECORDING CAPABILITIES; Inventors: Frederick E. Shelton, IV, John N. Ouwerkerk, and Eugene L. Timperman (K&LNG 050698/END5773USNP);

(10) ELECTRONIC LOCKOUTS AND SURGICAL INSTRUMENT INCLUDING SAME; Inventors: Jeffrey S. Swayze, Frederick E. Shelton, IV, Kevin R. Doll (K&LNG 050700/END5775USNP);

(11) ENDOSCOPIC SURGICAL INSTRUMENT WITH A HANDLE THAT CAN ARTICULATE WITH RESPECT TO THE SHAFT; Inventors: Frederick E. Shelton, IV, Jeffrey S. Swayze, Mark S. Ortiz, and Leslie M. Fugikawa (K&LNG 050701/END5776USNP);

(12) ELECTRO-MECHANICAL SURGICAL CUTTING AND FASTENING INSTRUMENT HAVING A ROTARY FIRING AND CLOSURE SYSTEM WITH PARALLEL CLOSURE AND ANVIL ALIGNMENT COMPONENTS; Inventors: Frederick E. Shelton, IV, Stephen J. Balek and Eugene L. Timperman (K&LNG 050702/END5777USNP);

(13) DISPOSABLE STAPLE CARTRIDGE HAVING AN ANVIL WITH TISSUE LOCATOR FOR USE WITH A SURGICAL CUTTING AND FASTENING INSTRUMENT AND MODULAR END EFFECTOR SYSTEM THEREFOR; Inventors: Frederick E. Shelton, IV, Michael S. Cropper, Joshua M. Broehl, Ryan S. Crisp, Jamison J. Float, Eugene L. Timperman (K&LNG 050703/END5778USNP); and

(14) SURGICAL INSTRUMENT HAVING A FEEDBACK SYSTEM; Inventors: Frederick E. Shelton, IV, Jerome R. Morgan, Kevin R. Doll, Jeffrey S. Swayze and Eugene L. Timperman (K&LNG 050705/EDN5780USNP).

BACKGROUND

This application discloses an invention that is related, generally and in various embodiments, to motor-driven surgical instruments having a removable battery.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which discloses an endocutter with distinct closing and firing actions. A clinician using this device is able to close the jaw members upon tissue to position the tissue prior to firing. Once the clinician has determined that the jaw members are properly gripping tissue, the clinician can then fire the surgical stapler with either single or multiple firing strokes, thereby severing and stapling the tissue. The simultaneous severing and stapling avoids complications that may arise when performing such actions sequentially with different surgical tools that respectively only sever or staple.

One specific advantage of being able to close upon tissue before firing is that the clinician is able to-verify via-an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest for lower force-to-fire (FTF) to a level that all or a great majority of surgeons can handle. One known solution to lower FTF it use $CO_2$ or electrical motors. These devices have not faired much better than traditional hand-powered devices, but for a different reason. Surgeons typically prefer to experience proportionate force distribution to that being experienced by the end-effector in the forming the staple to assure them that the cutting/stapling cycle is complete, with the upper limit within the capabilities of most surgeons (usually around 15-30lbs). They also typically want to maintain control of deploying the staple and being able to stop at anytime if the forces felt in the handle of the device feel too great or for some other clinical reason. These user-feedback effects are not suitably realizable in present motor-driven endocutters. As a result, there is a general lack of acceptance by physicians of motor-drive endocutters where the cutting/stapling operation is actuated by merely pressing a button.

A growing number of motor-driven surgical instruments are powered by one or more batteries disposed within the instrument. In many jurisdictions, regulations require that each battery be sterilized before being disposed within the instrument and/or before use of the instrument in a medical procedure. Many jurisdictions also require that each battery be disposed of in a manner that is different than the manner the remainder of the instrument may be disposed of.

For a variety of reasons, a motor-driven surgical instrument may need to have one or more of its batteries replaced. Surgical instrument manufacturers invest significant amounts of capital to develop more advanced models of motor-driven surgical instruments. Based at least in part on the number of instruments the manufacturer projects will be sold for a particular model, a portion of the development cost associated with the particular model is generally factored in to the purchase price of each instrument. Some of these motor-driven surgical instruments are designed to only be used a limited number of times. Accordingly, if a number of the instruments are used more times than the instruments are designed for, the manufacturer may fail to fully recoup the development cost associated with the particular model.

SUMMARY

This application discloses a surgical instrument. According to various embodiments, the surgical instrument comprises a handle, a battery, a motor, and a lockout system. The handle comprises a primary portion and a grip portion. The grip portion is releasably connected to the primary portion. The battery is within the grip portion. The motor is in electrical communication with the battery. The lockout system is within the handle, and is structured and arranged to block connection of the grip portion to the primary portion after the grip portion is disconnected from the primary portion a predetermined number of times.

According to other embodiments, the surgical instrument comprises a handle, a battery, and a motor. The handle comprises a primary portion and a grip portion. The grip portion is releasably connected to the primary portion. A portion of the grip portion is structured and arranged to break off of the grip portion and remain in contact with the primary portion when the grip portion is disconnected from the primary portion. The battery is within the grip portion. The motor is in electrical communication with the battery.

According to other embodiments, the surgical instrument comprises a handle, a battery, a motor, and a counter. The handle comprises a primary portion and a grip portion. The grip portion is releasably connected to the primary portion. The battery is within the grip portion. The motor is in electrical communication with the battery. The counter is within the handle, and is structured and arranged to open a motor interlock.

DRAWINGS

Various embodiments of the disclosed invention are described herein by way of example in conjunction with the following figures.

Figure 41:
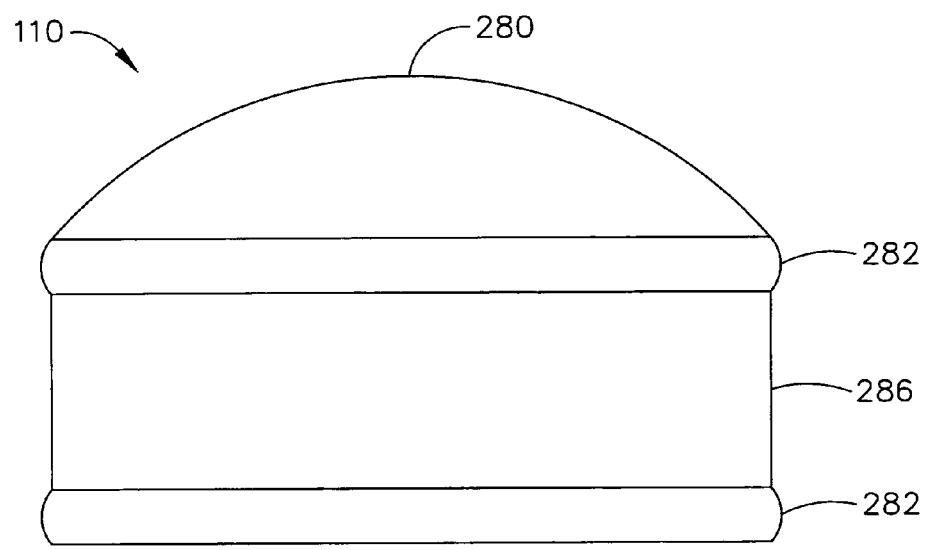
Figure 42:
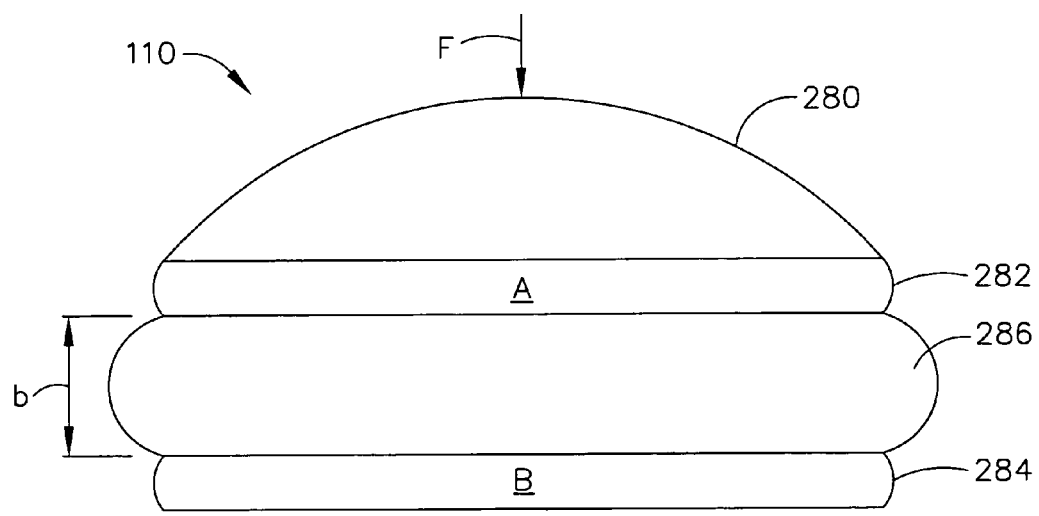
Figure 43:
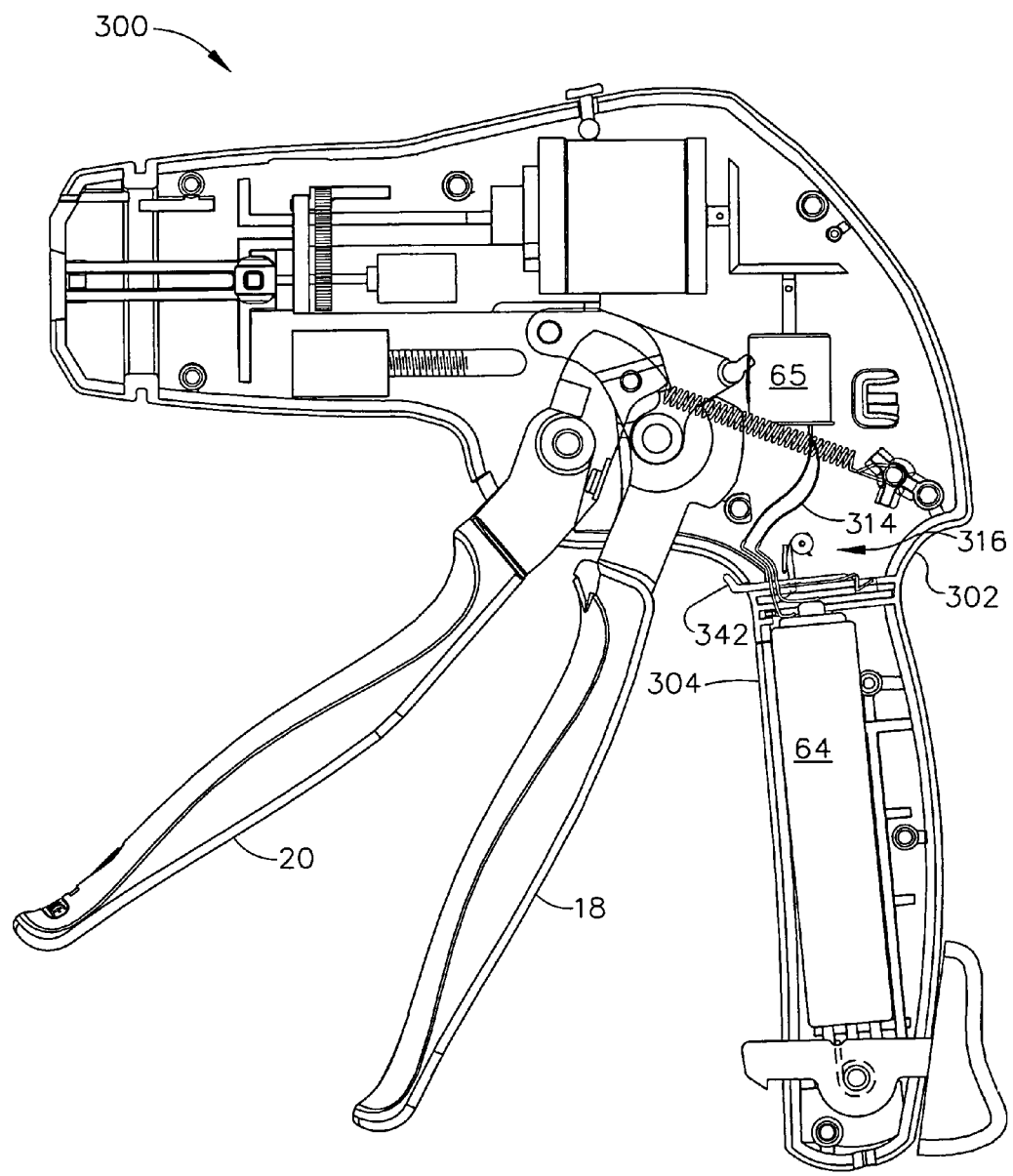
Figure 44:
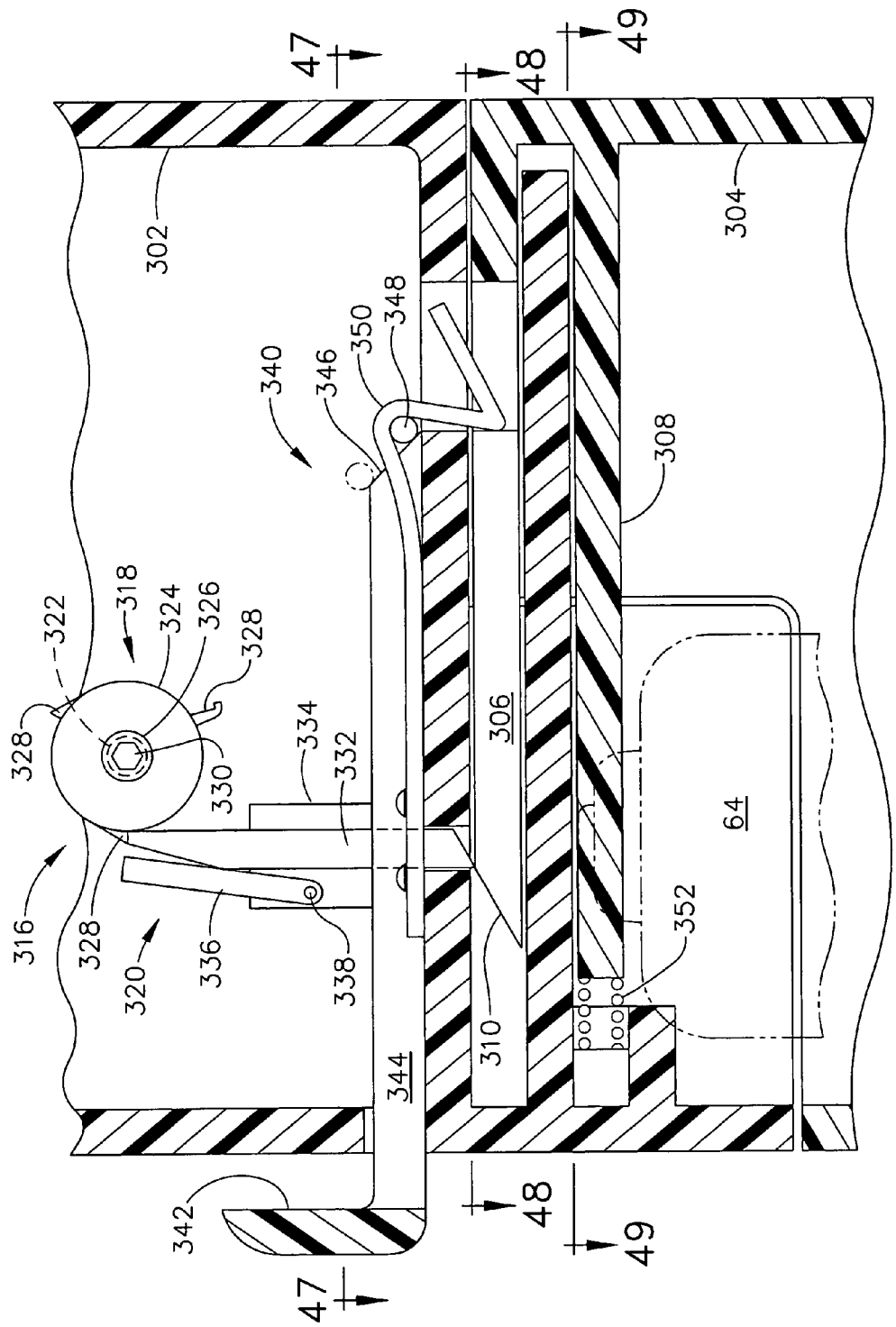
Figure 45:
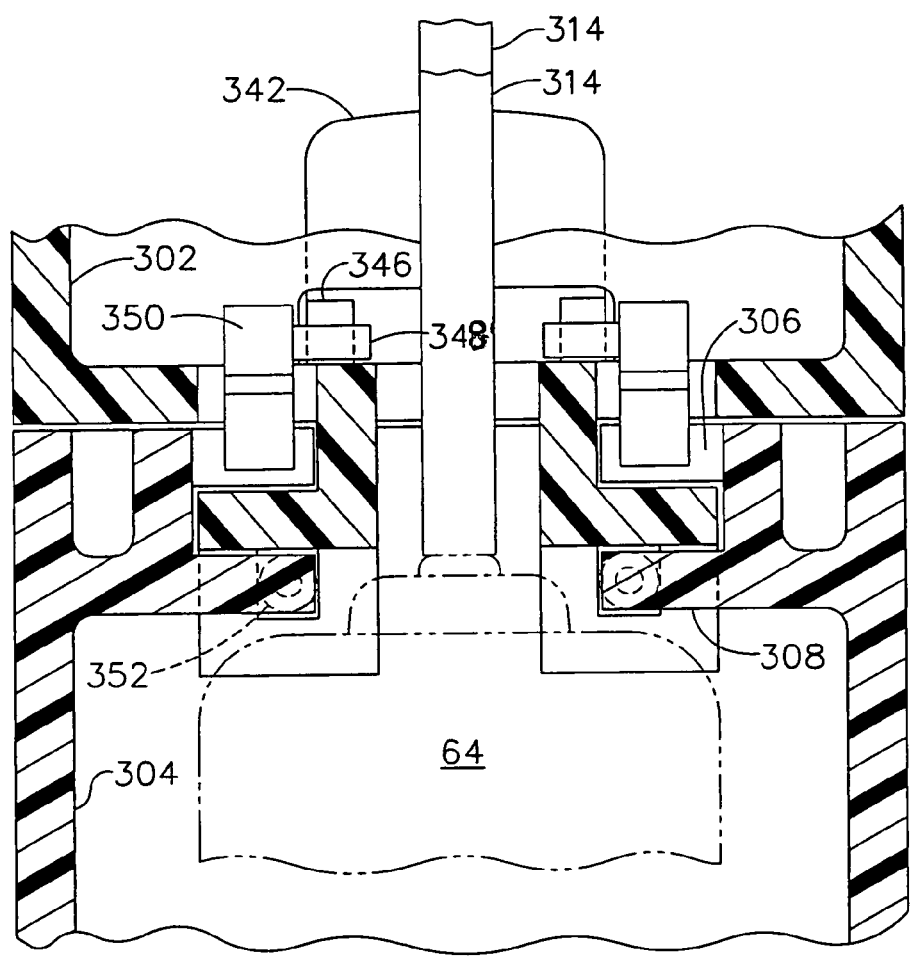
Figure 46:
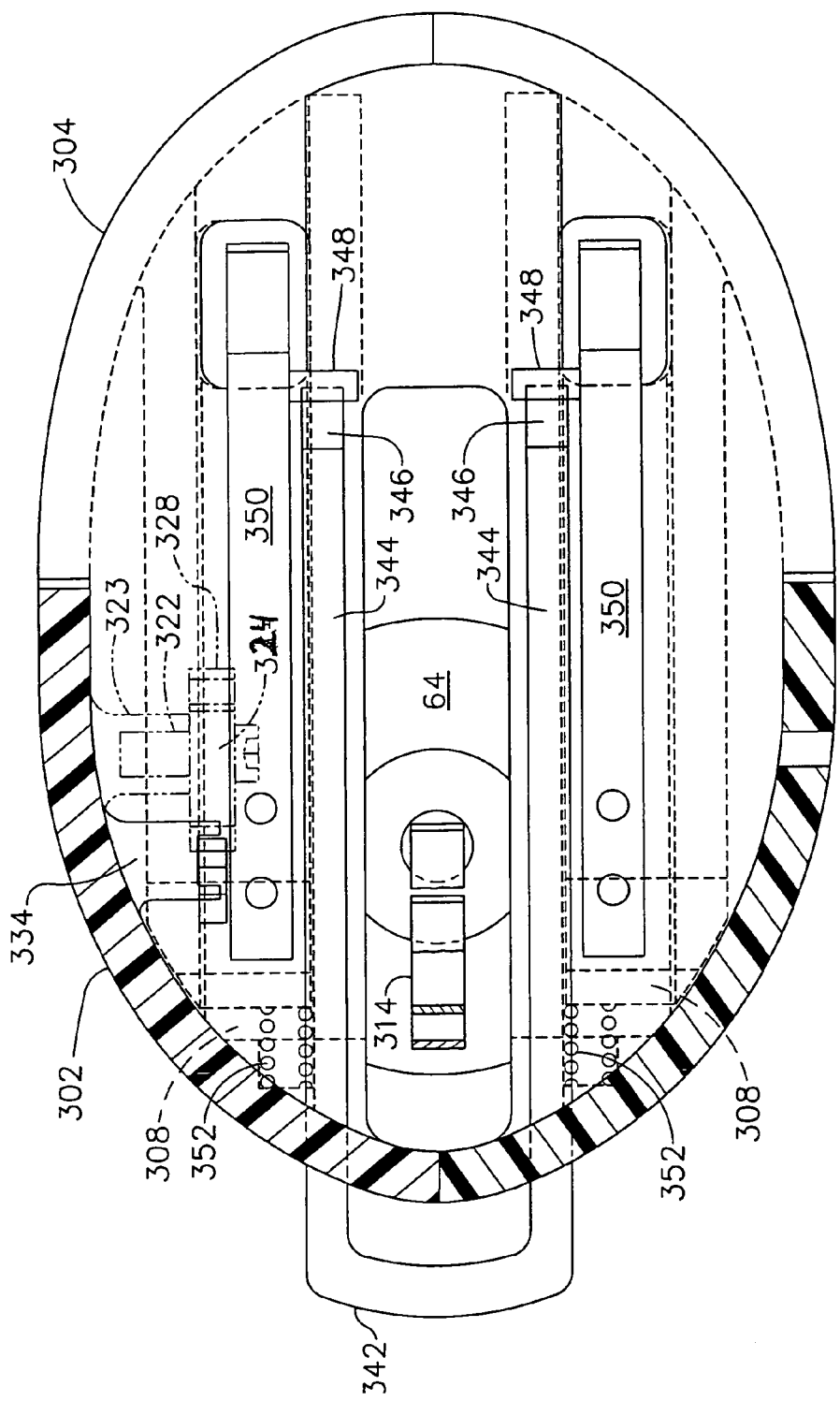
Figure 47:
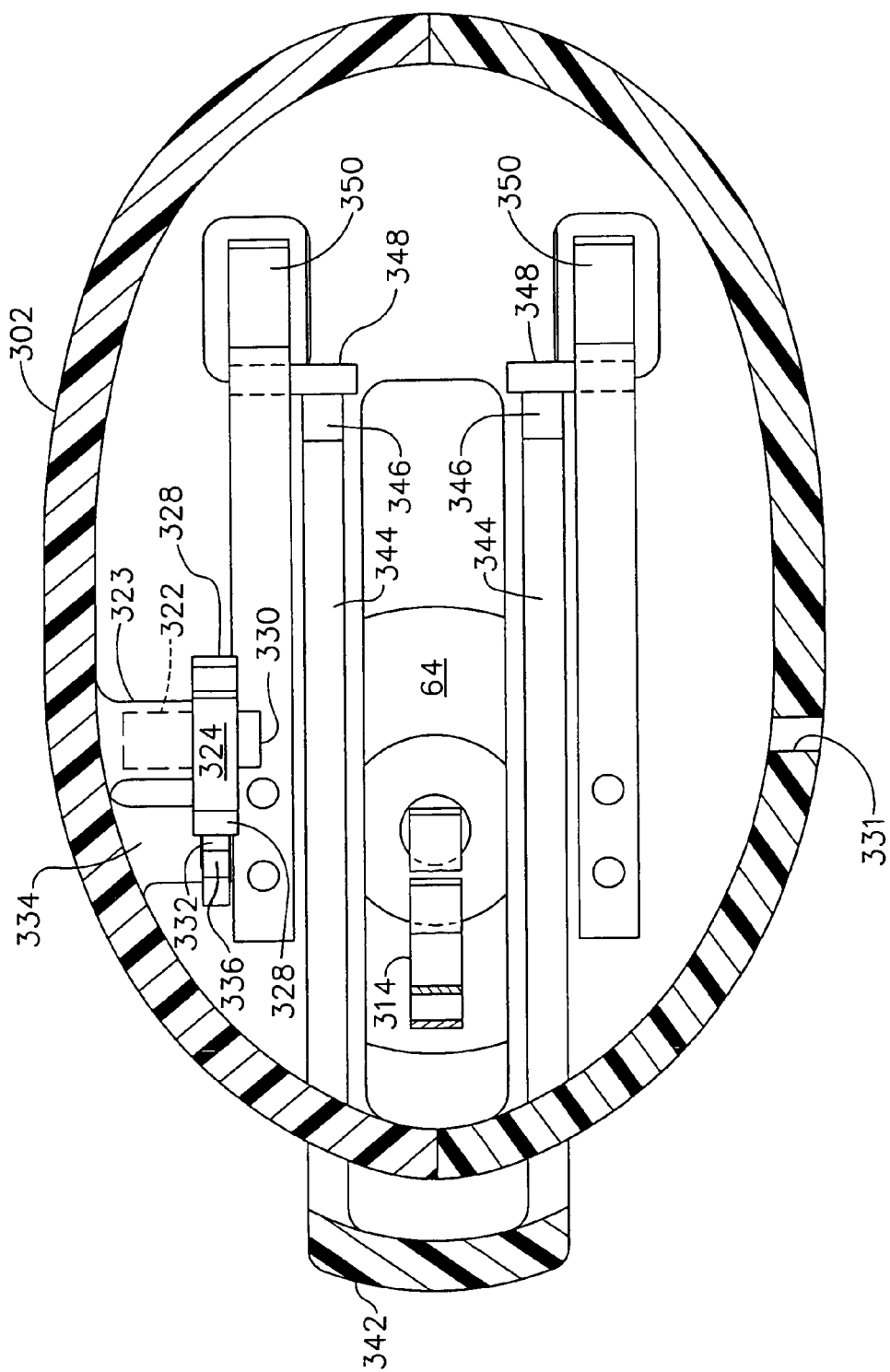
Figure 48:
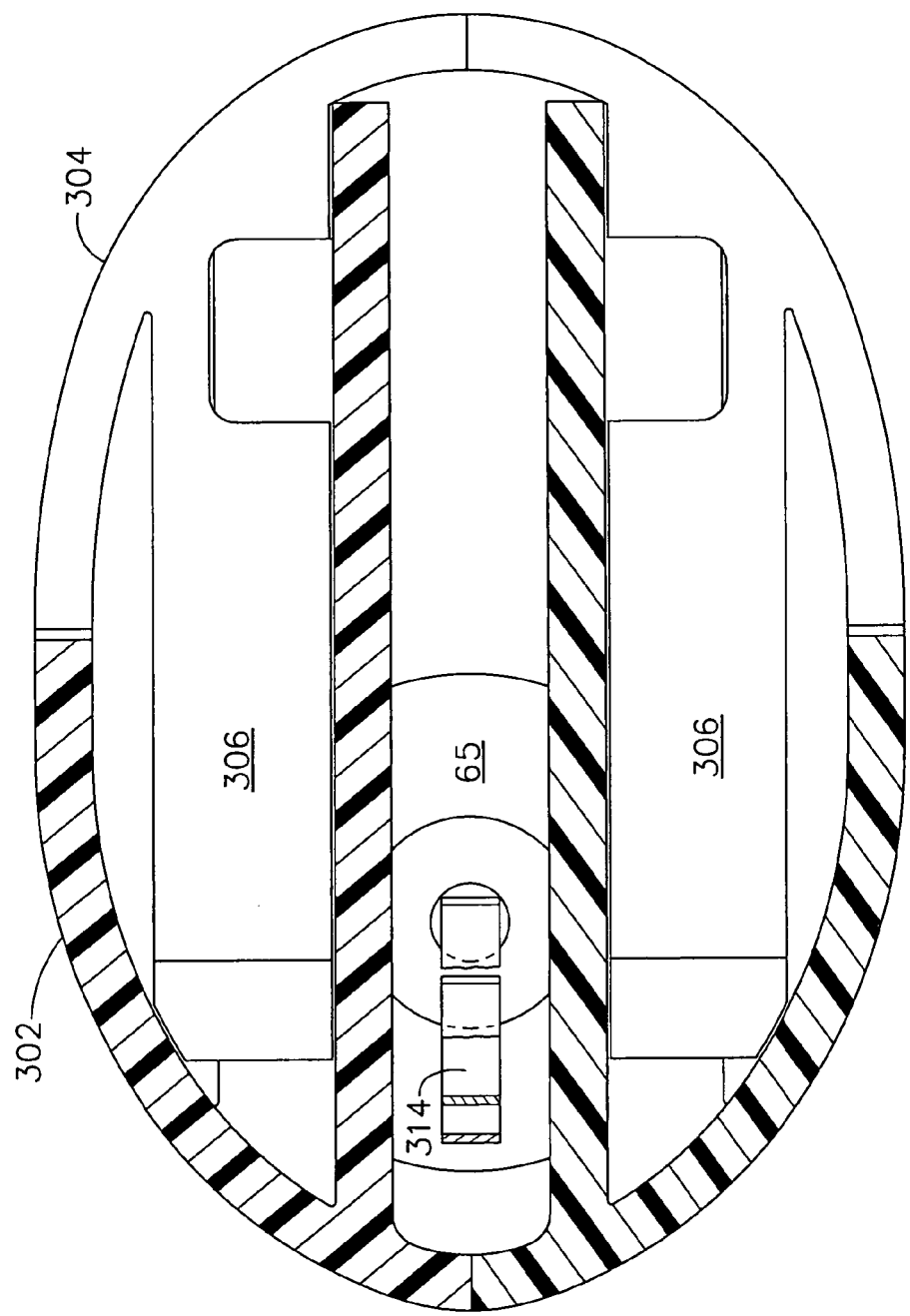
Figure 49:
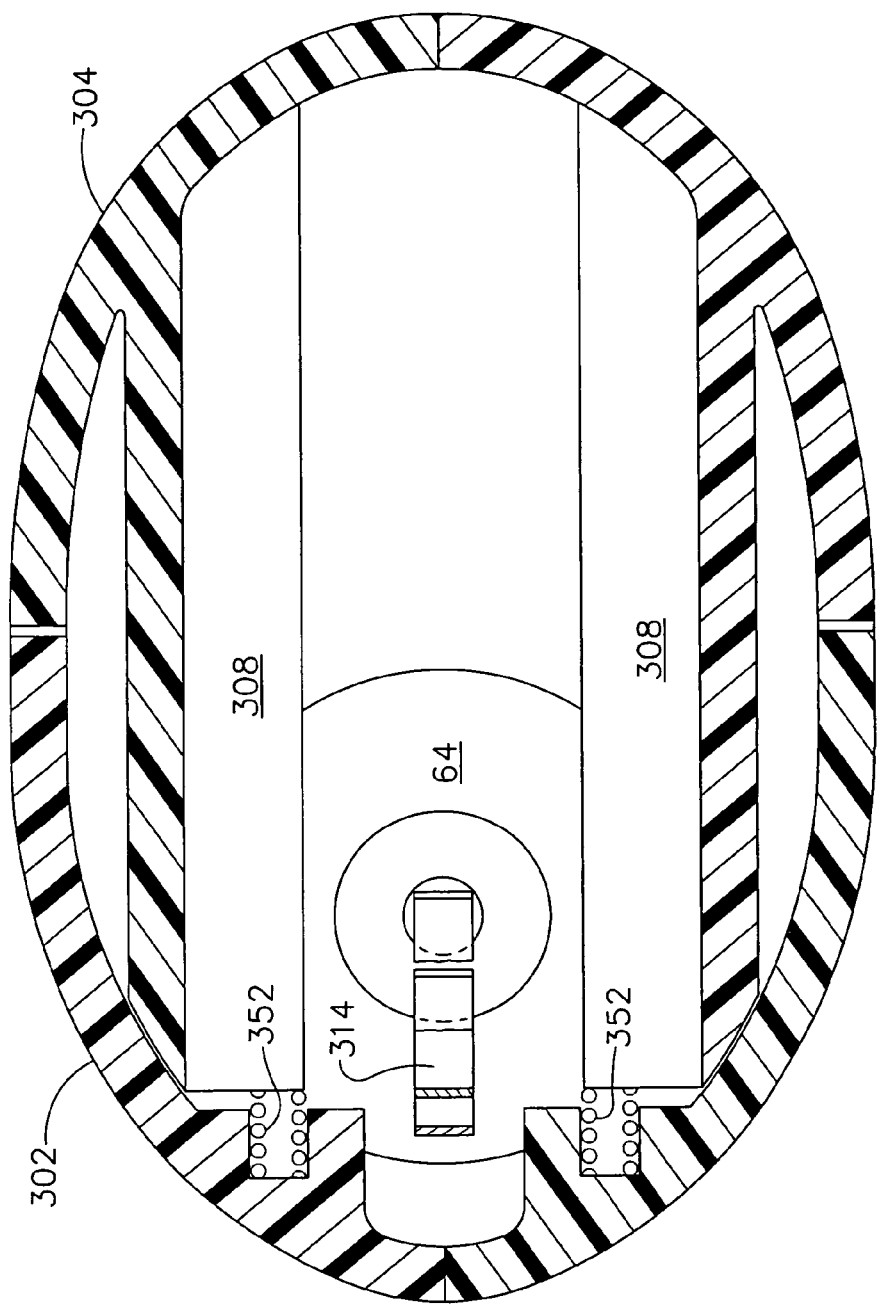
Figure 56:
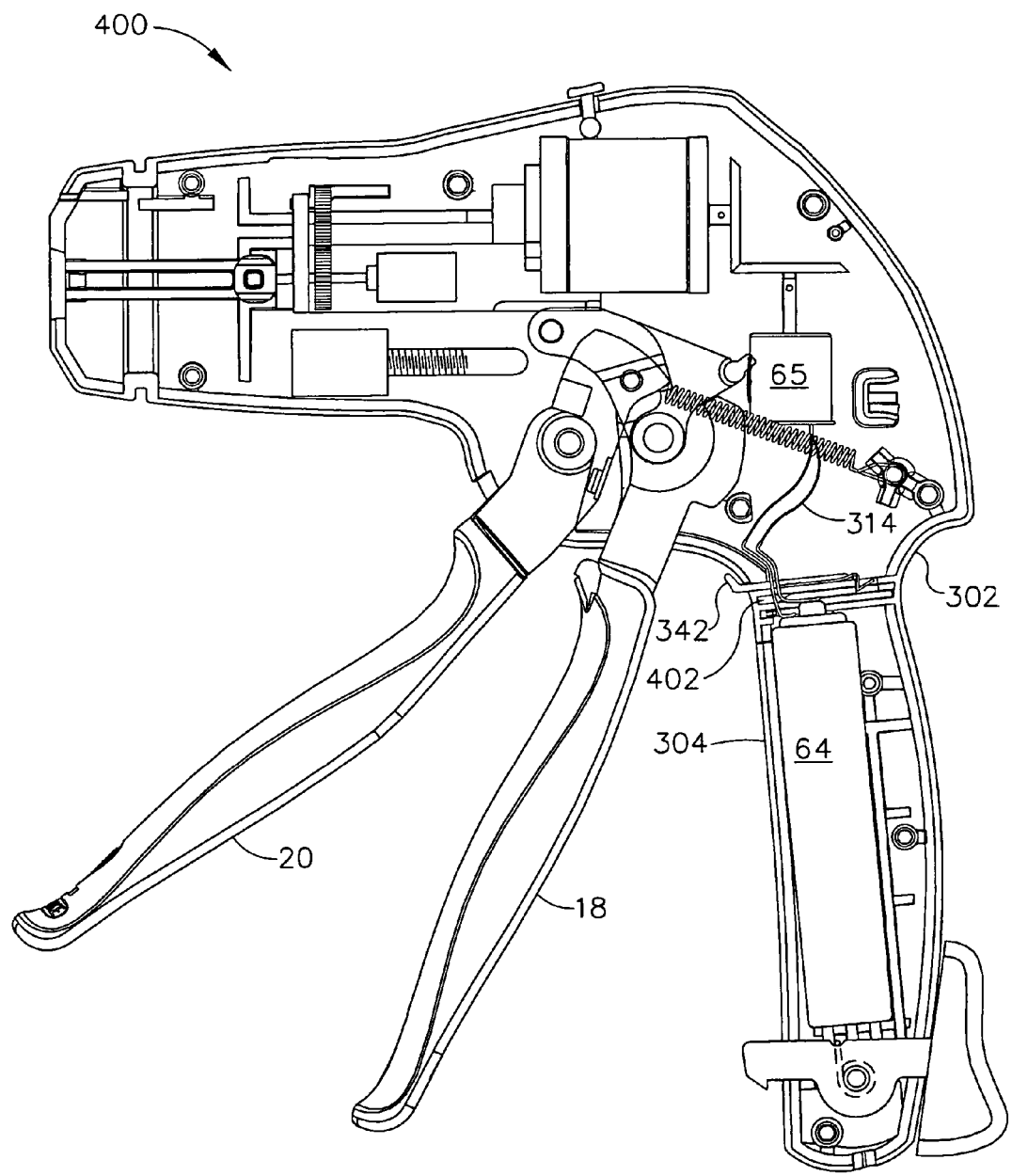
Figure 57:
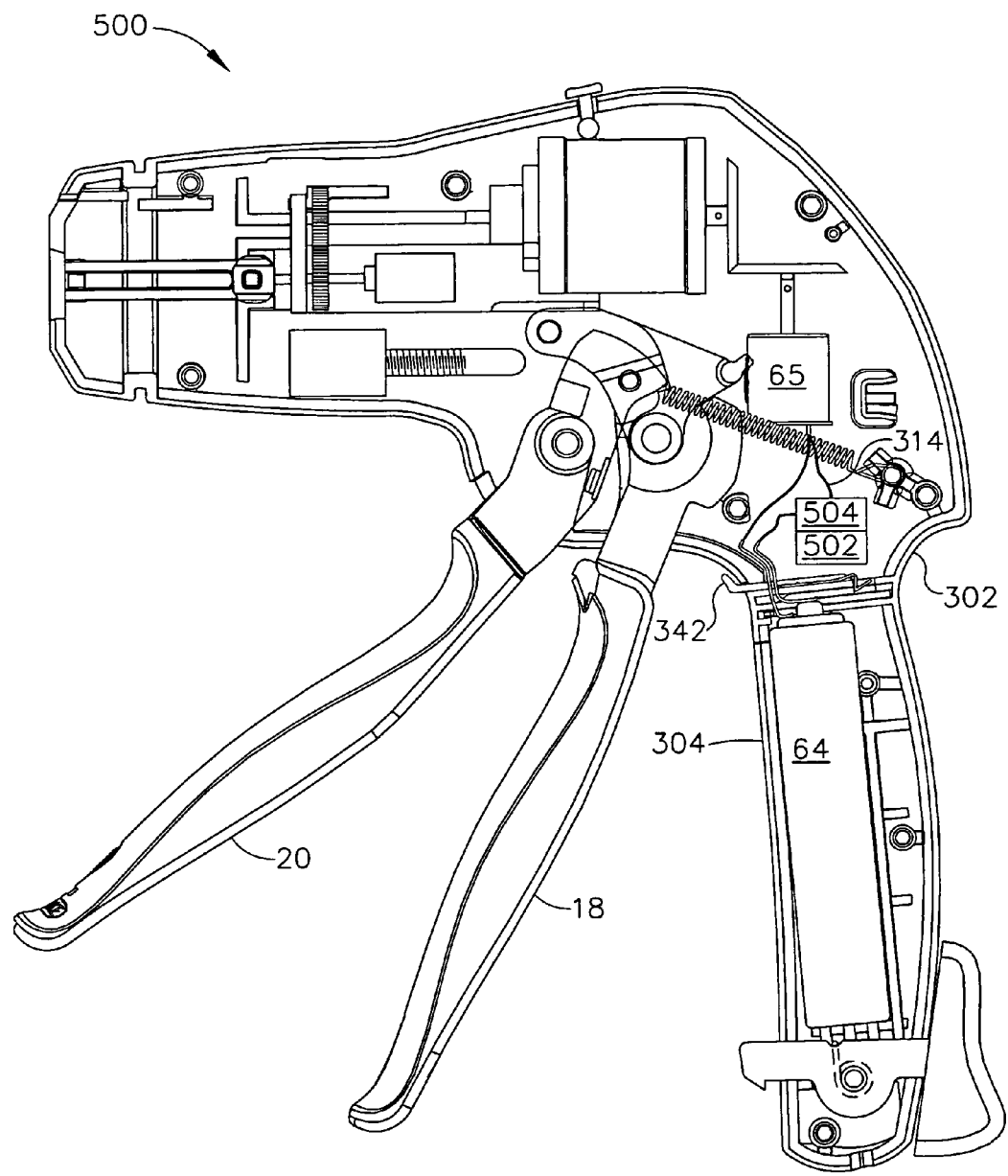
Figure 58:
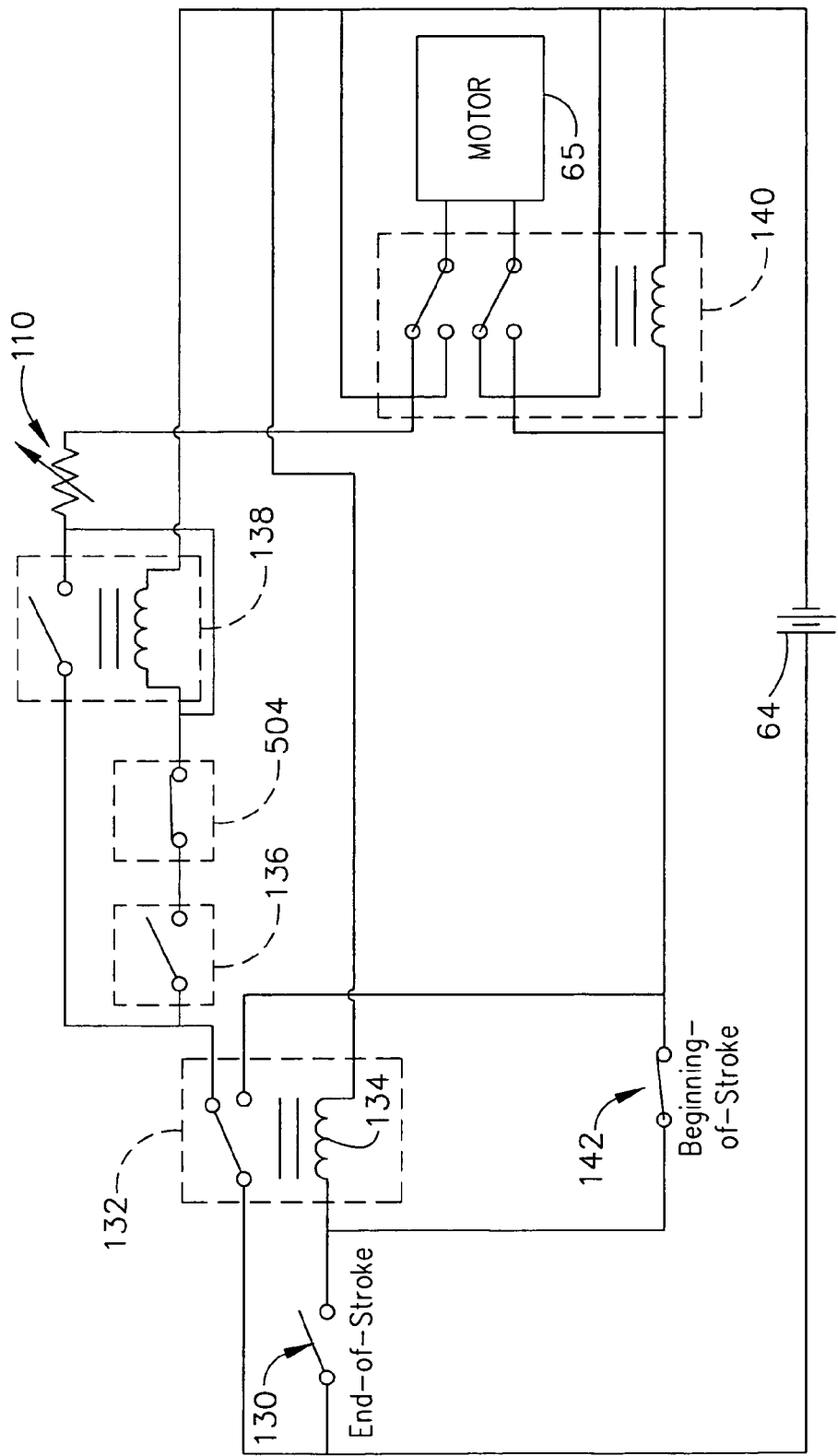

FIGS. 23A-B show a universal joint ("u-joint") that may be employed at the articulation point of the instrument according to various embodiments;

FIGS. 24A-B shows a torsion cable that may be employed at the articulation point of the instrument according to various embodiments;

FIGS. 25-31 illustrate a surgical cutting and fastening instrument with power assist according to various embodiments;

FIGS. 32-36 illustrate a surgical cutting and fastening instrument with power assist according to various embodiments;

FIGS. 37-40 illustrate a surgical cutting and fastening instrument with tactile feedback according to various embodiments;

FIGS. 41-42 illustrate various embodiments of a proportional sensor;

FIG. 43 is a cross-sectional view of a portion of a surgical instrument according to various embodiments;

FIG. 44 is a cross-sectional view of a portion of a surgical instrument according to various embodiments;

FIG. 45 is a cross-sectional view of a portion of a surgical instrument according to various embodiments;

FIG. 46 is a composite view of portions of a surgical instrument according to various embodiments;

FIG. 47 is a cross-section view of the surgical instrument of FIG. 44 along line 5-5;

FIG. 48 is a cross-section view of the surgical instrument of FIG. 44 along line 6-6;

FIG. 49 is a cross-section view of the surgical instrument of FIG. 44 along line 7-7;

FIGS. 50-55 are schematics showing the operation of a portion of a surgical instrument according to various embodiemnts;

FIG. 56 is a cross-sectional view of a portion of a surgical instrument according to various embodiments;

FIG. 57 is a cross-sectional view of a portion of a surgical instrument according to various embodiments; and FIG. 58 is a schematic diagram of a circuit used in the surgical instrument of FIG. 57 according to various embodiments.

DETAILED DESCRIPTION

It is to be understood that at least some of the figures and descriptions of the disclosed invention have been simplified to illustrate elements that are relevant for a clear understanding of the disclosed invention, while eliminating, for purposes of clarity, other elements. Those of ordinary skill in the art will recognize, however, that these and other elements may be desirable. However, because such elements are well known in the art, and because they do not facilitate a better understanding of the disclosed invention, a discussion of such elements is not provided herein.

Figure 1:
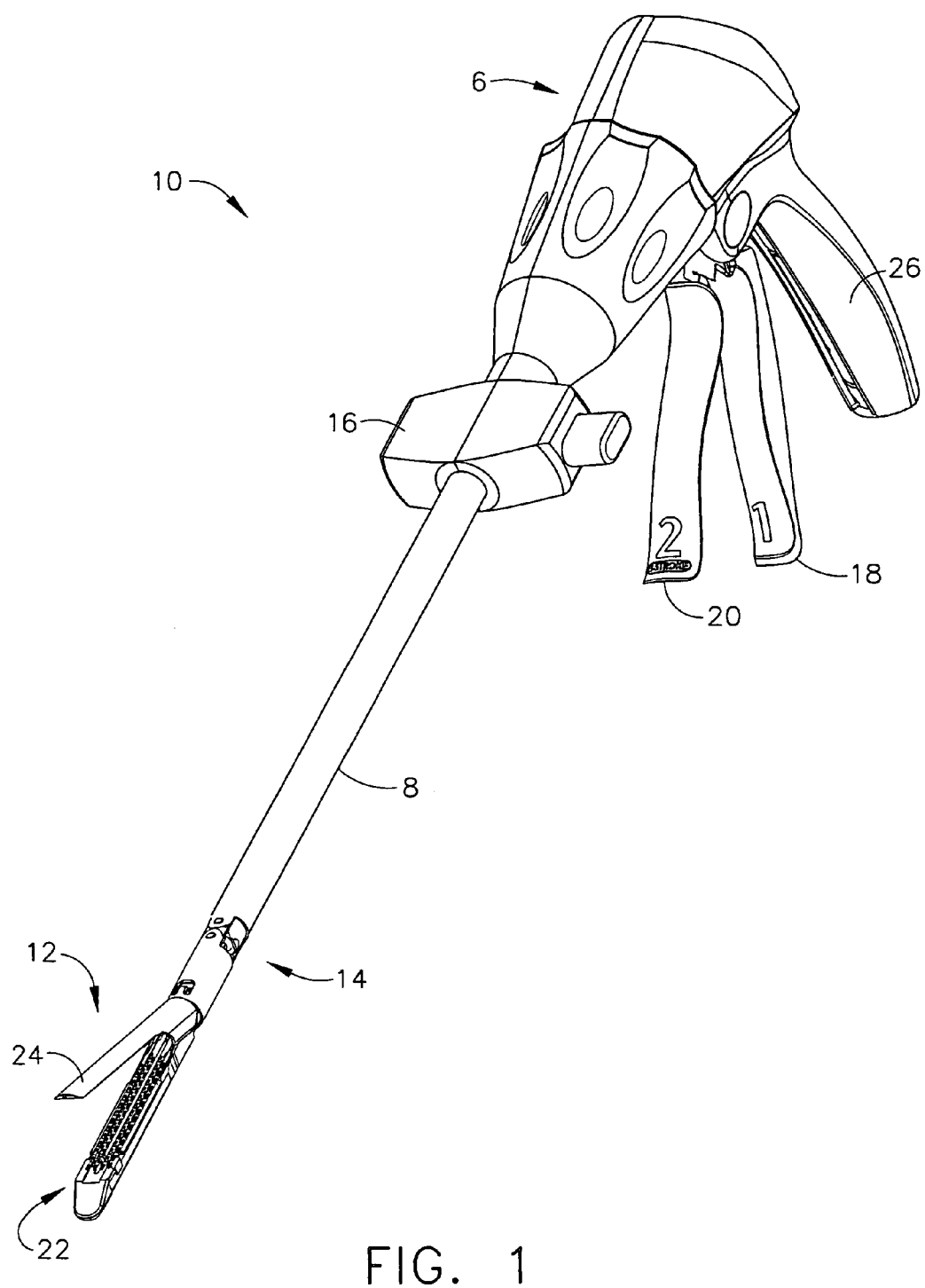
FIGS. 1 and 2 are perspective views of a surgical cutting and fastening instrument according to various embodiments.
Figure 2:
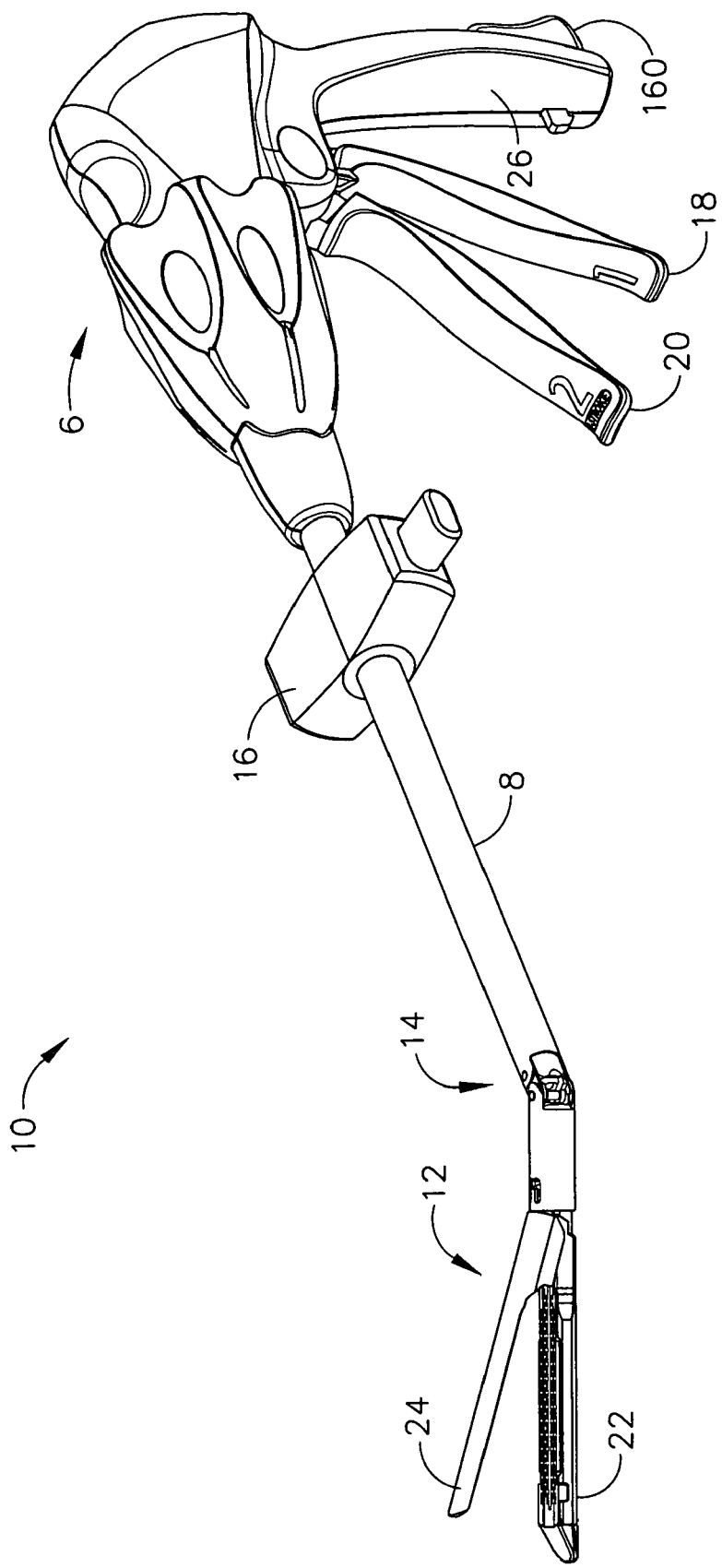

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button 160 on the handle 6, and in this example, on the pistol grip 26 of the handle 6, when depressed may release the locked closure trigger 18.

Figure 3:
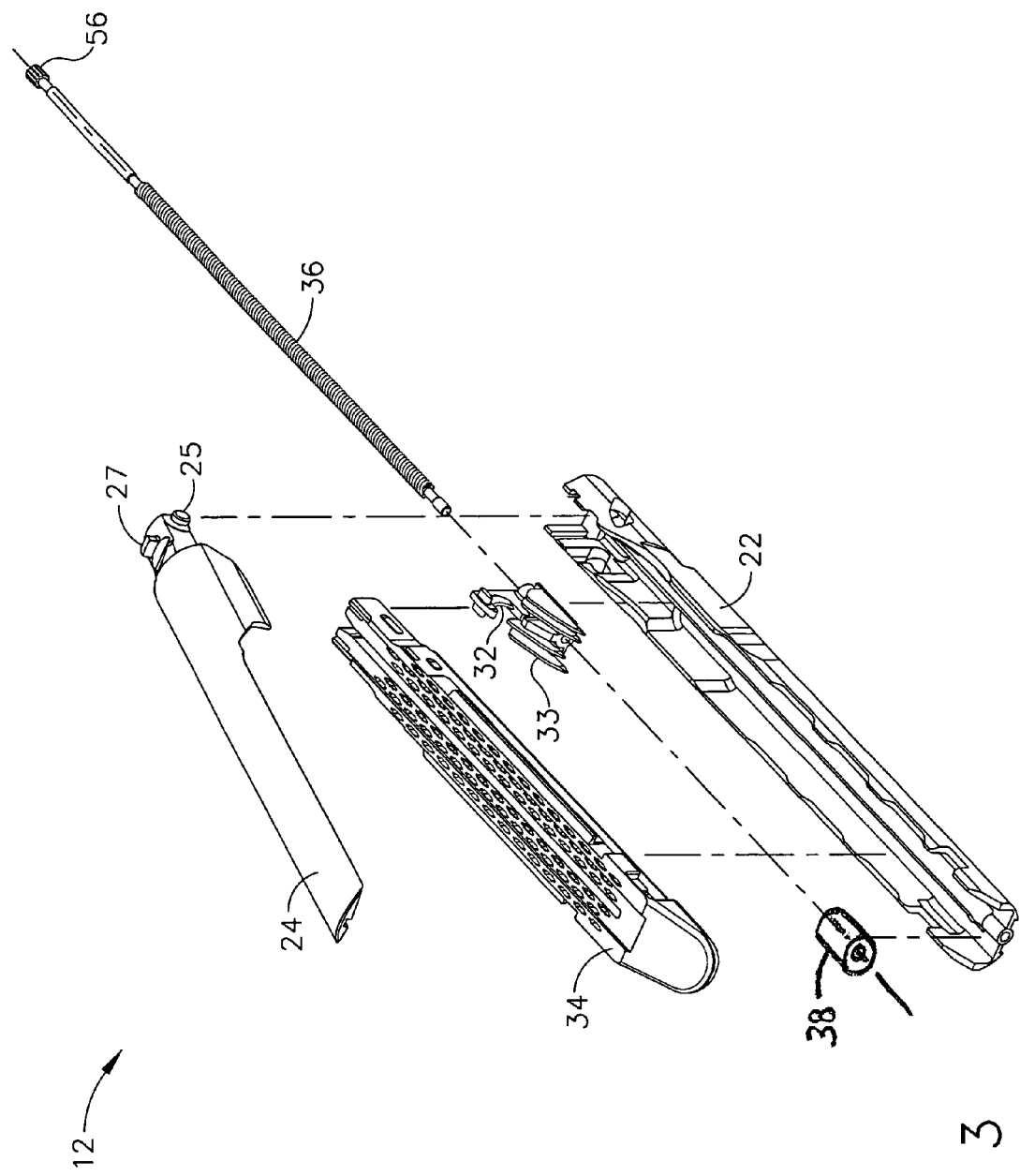
FIGS. 3-5 are exploded views of an end effector and shaft of the instrument according to various embodiments.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. U.S. Pat. No. 6,978,921, entitled "Surgical Stapling Instrument Incorporating An E-Beam Firing Mechanism," which is incorporated herein by reference, provides more details about such two-stroke cutting and fastening instruments. According to various embodiments, the sled 33 may be an integral part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,810,811, entitled "Electrosurgical Hemostatic Device," which is incorporated herein by reference, discloses a cutting instrument that uses RF energy to fasten the severed tissue. U.S. patent application Ser. No. 11/267,811, entitled "Surgical Stapling Instruments Structured For Delivery Of Medical Agents" and U.S. patent application Ser. No. 11/267,383, entitled "Surgical Stapling Instruments Structured For Pump-Assisted Delivery Of Medical Agents," both of which are also incorporated herein by reference, disclose cutting instruments that use adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
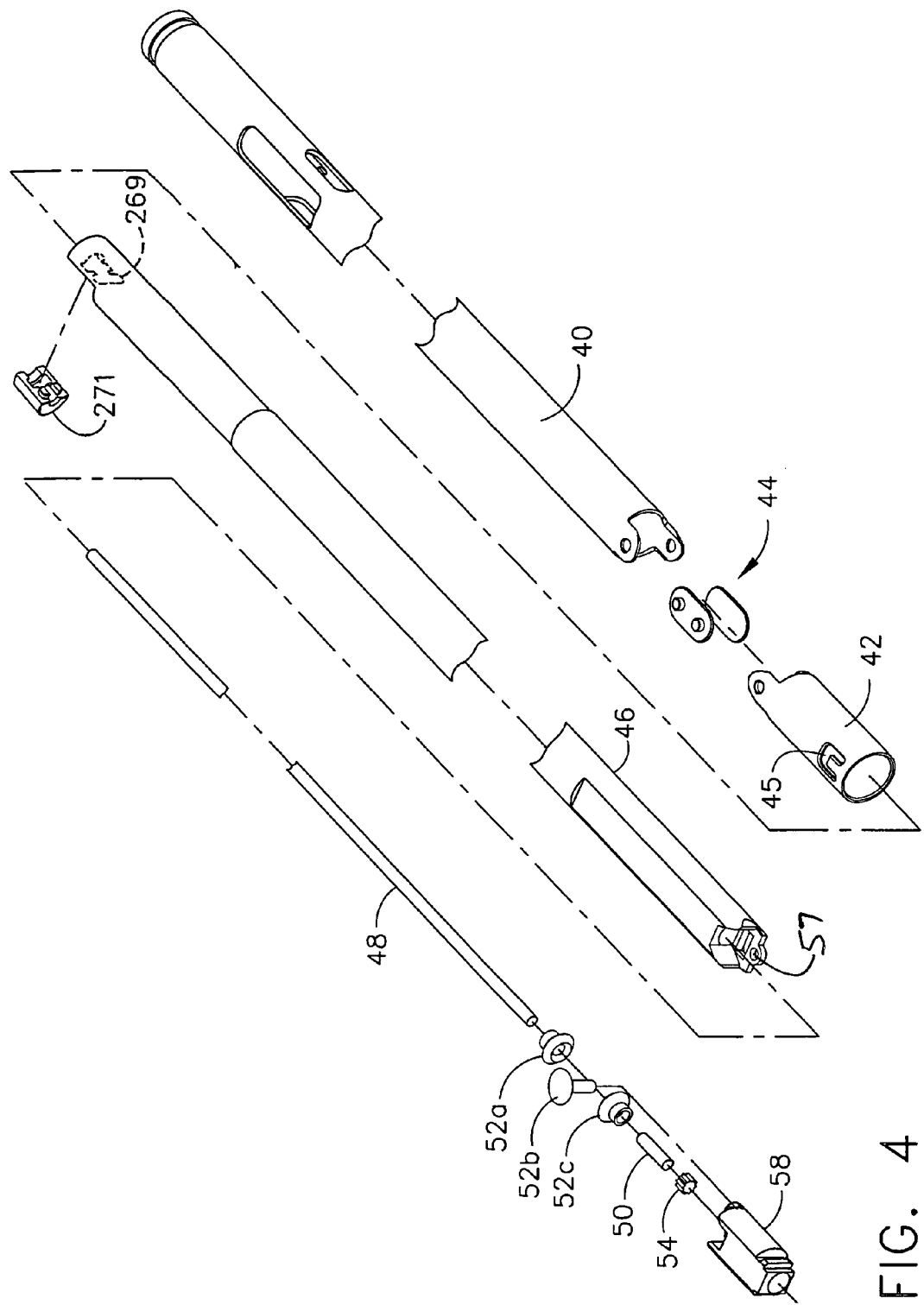
Figure 5:
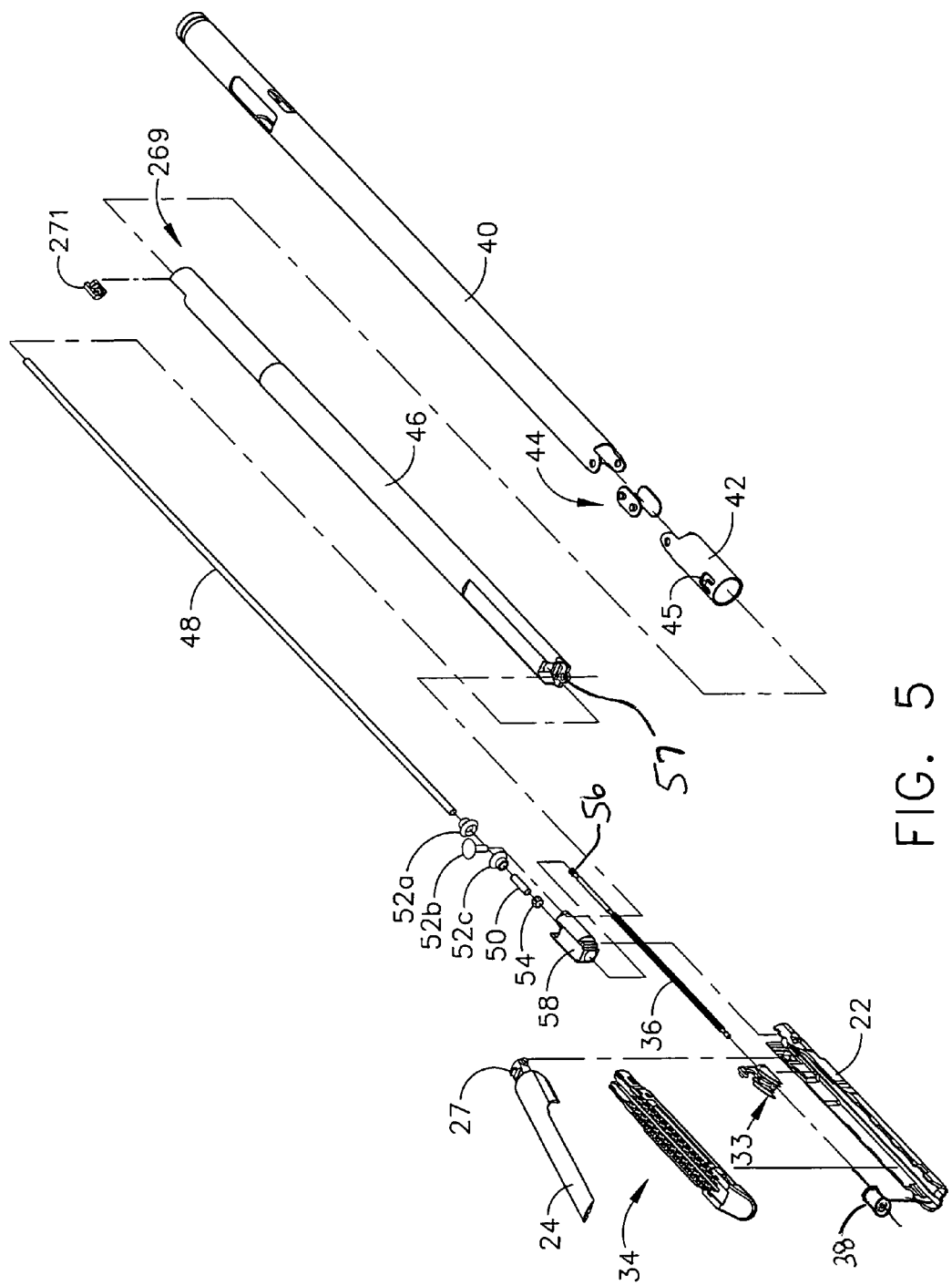
Figure 6:
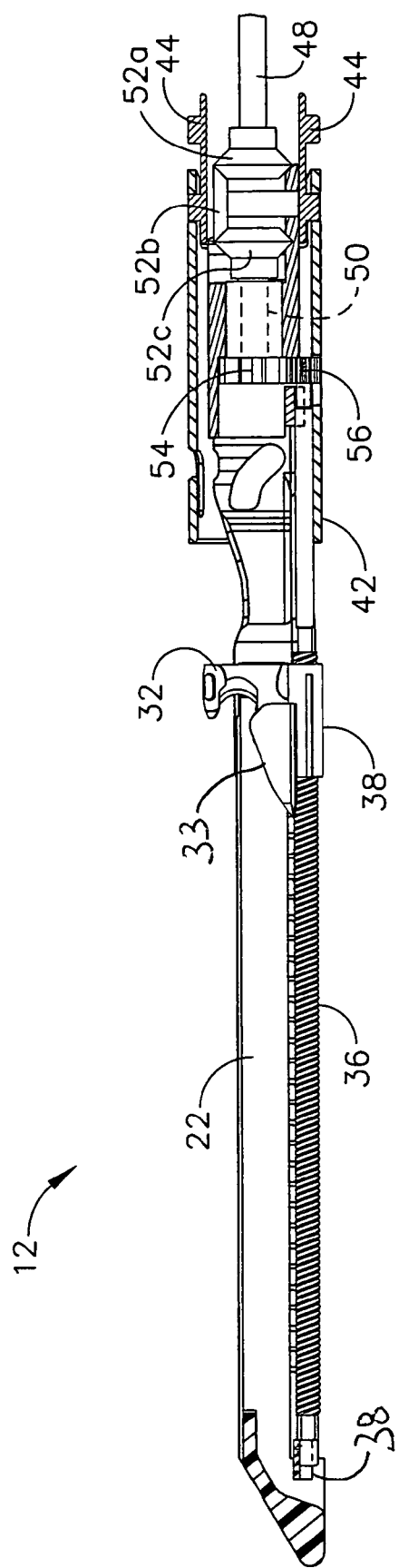
FIG. 6 is a side view of the end effector according to various embodiments.
Figure 7:
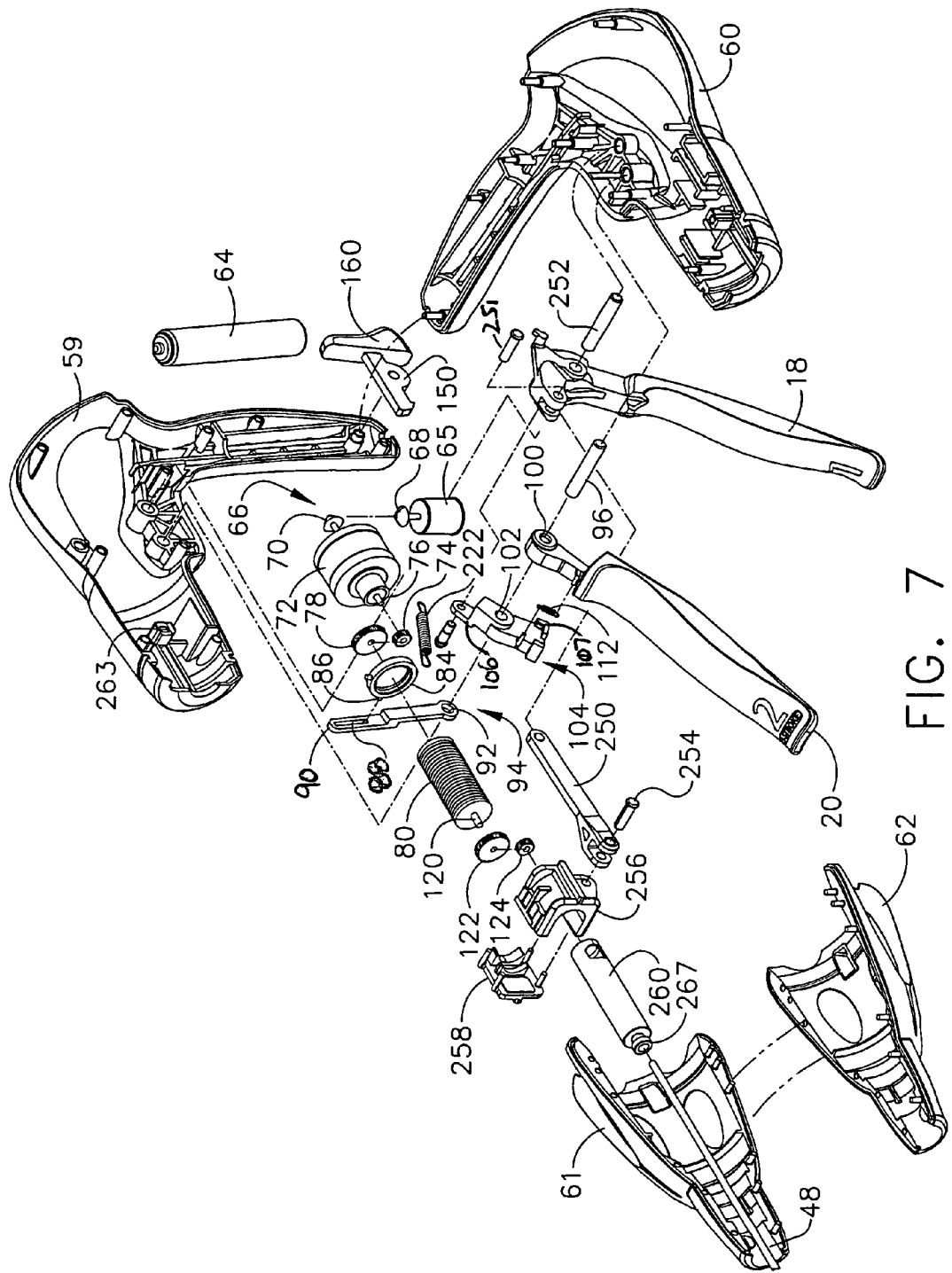
FIG. 7 is an exploded view of the handle of the instrument according to various embodiments.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. When the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife/sled driving member 32 to travel longitudinally along the channel 22 to cut any tissue clamped within the end effector 12. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38 is threaded on the helical drive screw 36. The bearing 36 is also connected to the knife 32. When the helical drive screw 36 forward rotates, the bearing 38 traverses the helical drive screw 36 distally, driving the cutting instrument 32 and, in the process, the sled 33 to perform the cutting/stapling operation. The sled 33 may be made of, for example, plastic, and may have a sloped distal surface. As the sled 33 traverses the channel 22, the sloped forward surface may push up or drive the staples in the staple cartridge 34 through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

Because of the lack of user feedback for the cutting/stapling operation, there is a general lack of acceptance among physicians of motor-driven surgical instruments where the cutting/stapling operation is actuated by merely pressing a button. In contrast, embodiments of the present invention provide a motor-driven endocutter with user-feedback of the deployment, force, and/or position of the cutting instrument in the end effector.

FIGS. 7-10 illustrate an exemplary embodiment of a motor-driven endocutter, and in particular the handle 6 thereof, that provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
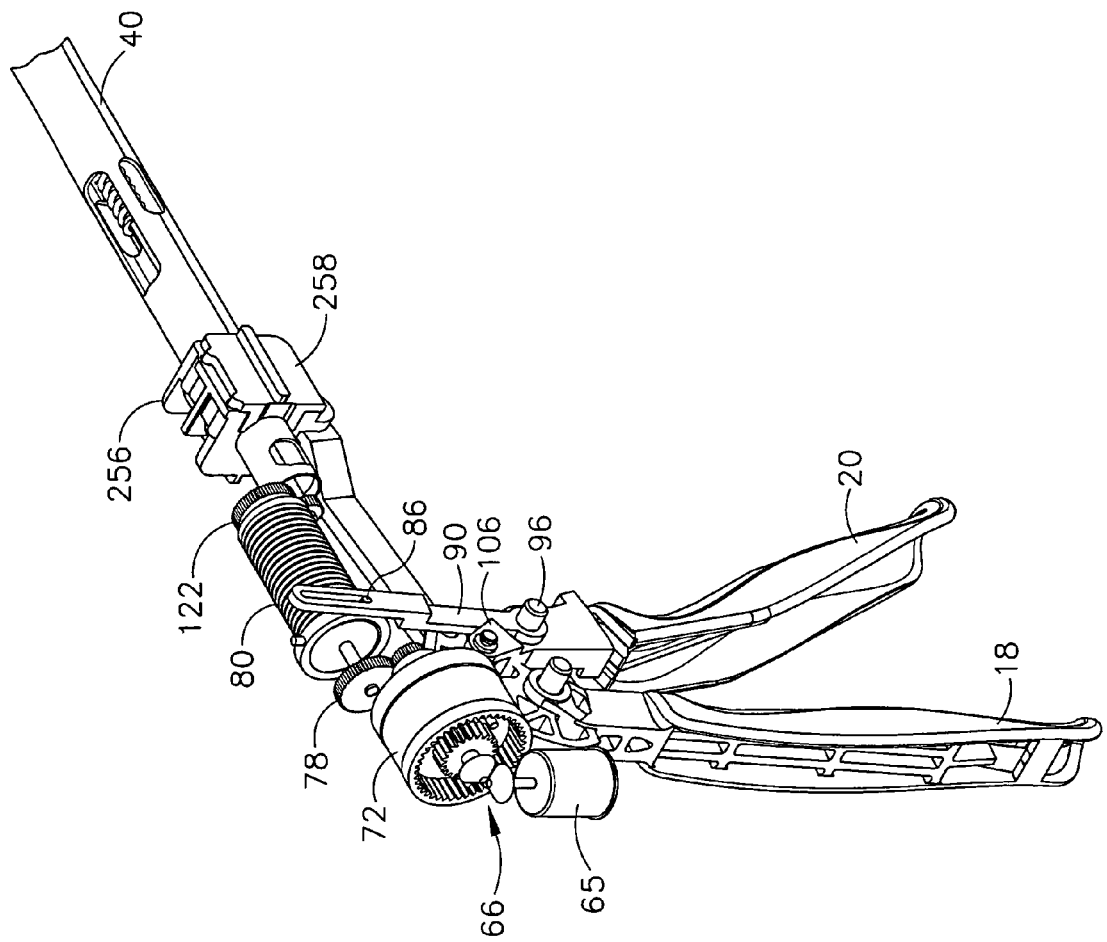
FIGS. 8 and 9 are partial perspective views of the handle according to various embodiments.
Figure 9:
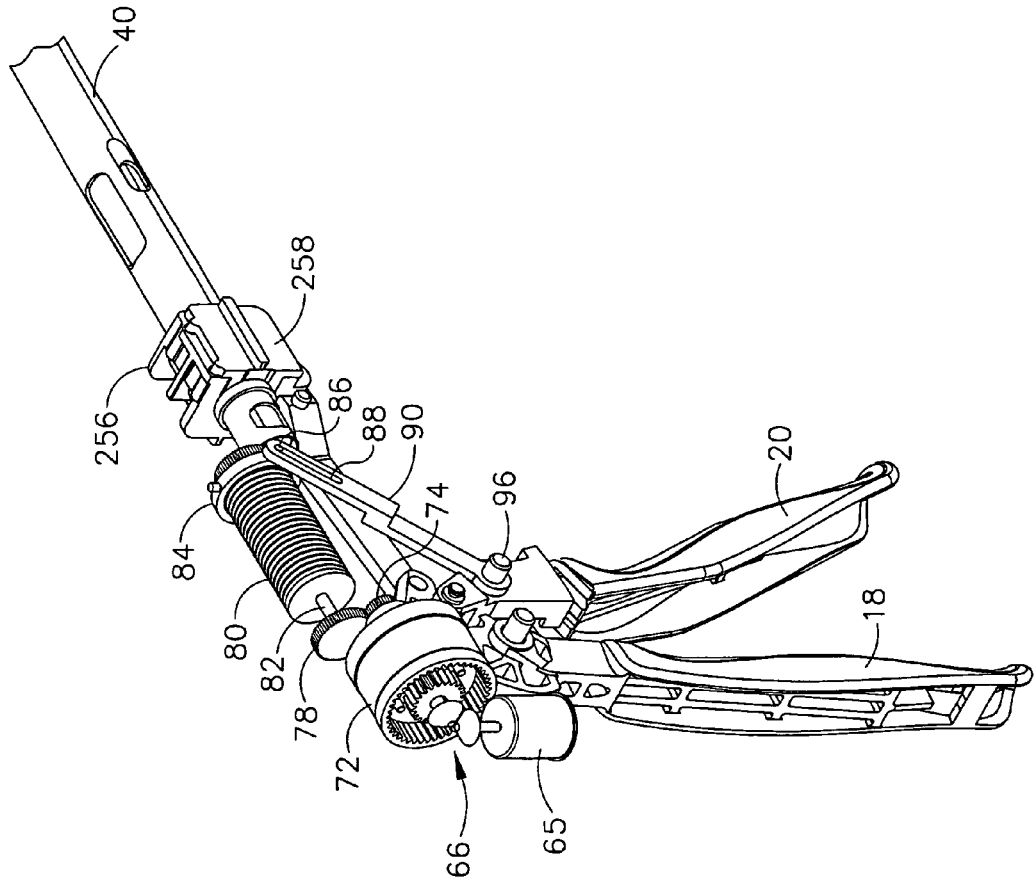
Figure 10:
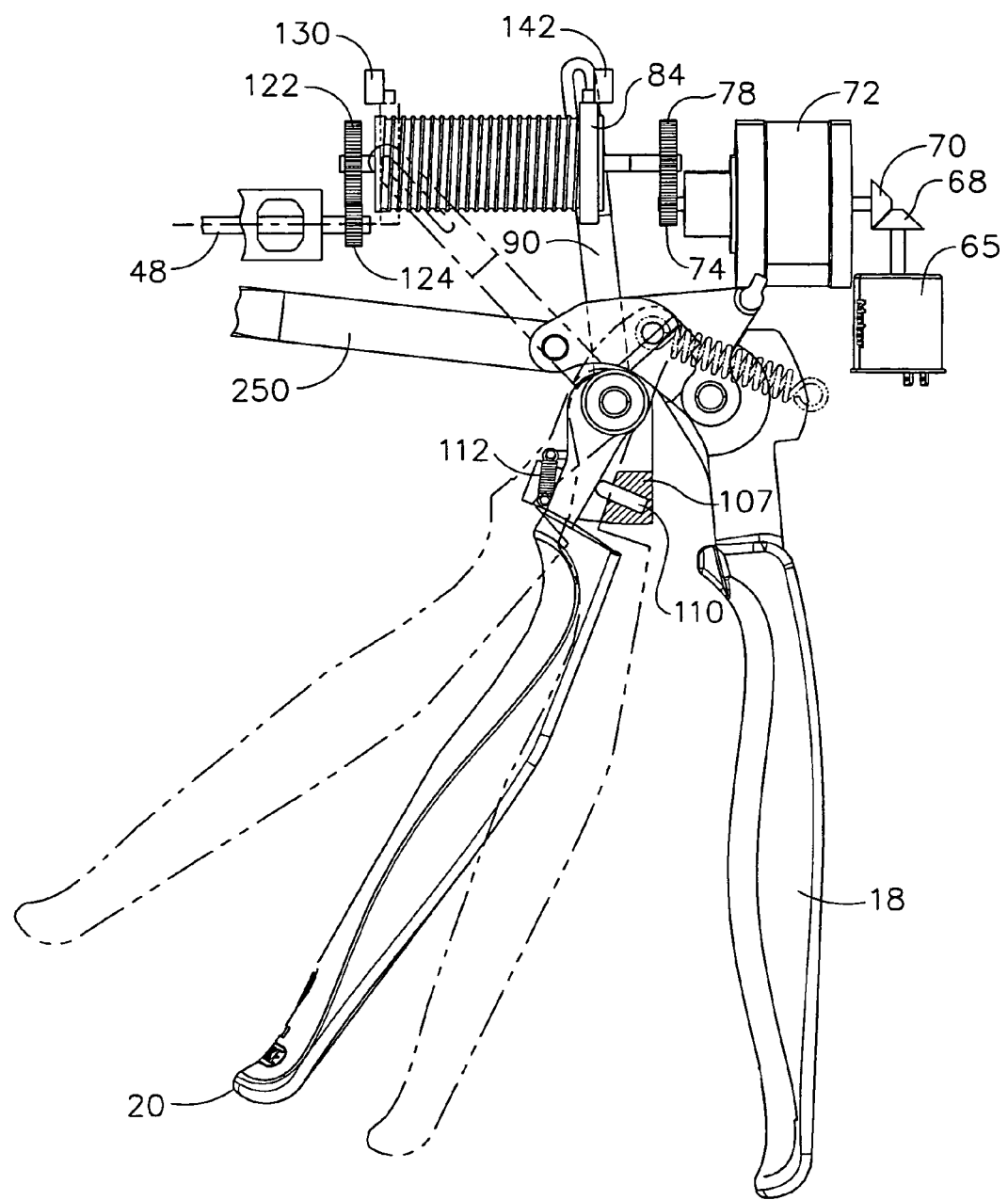
FIG. 10 is a side view of the handle according to various embodiments.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

FIGS. 41 and 42 illustrate two states of a variable sensor that may be used as the run motor sensor 110 according to various embodiments of the present invention. The sensor 110 may include a face portion 280, a first electrode (A) 282, a second electrode (B) 284, and a compressible dielectric material 286 (e.g., EAP) between the electrodes 282, 284. The sensor 110 may be positioned such that the face portion 280 contacts the firing trigger 20 when retracted. Accordingly, when the firing trigger 20 is retracted, the dielectric material 286 is compressed, as shown in FIG. 42, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric material 286 is compressed due to retraction of the firing trigger 20 (denoted as force "F" in FIG. 42) is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximally, which causes the distal closure tube 42 to slide proximally, which by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 18 from the locked position.

Figure 11:
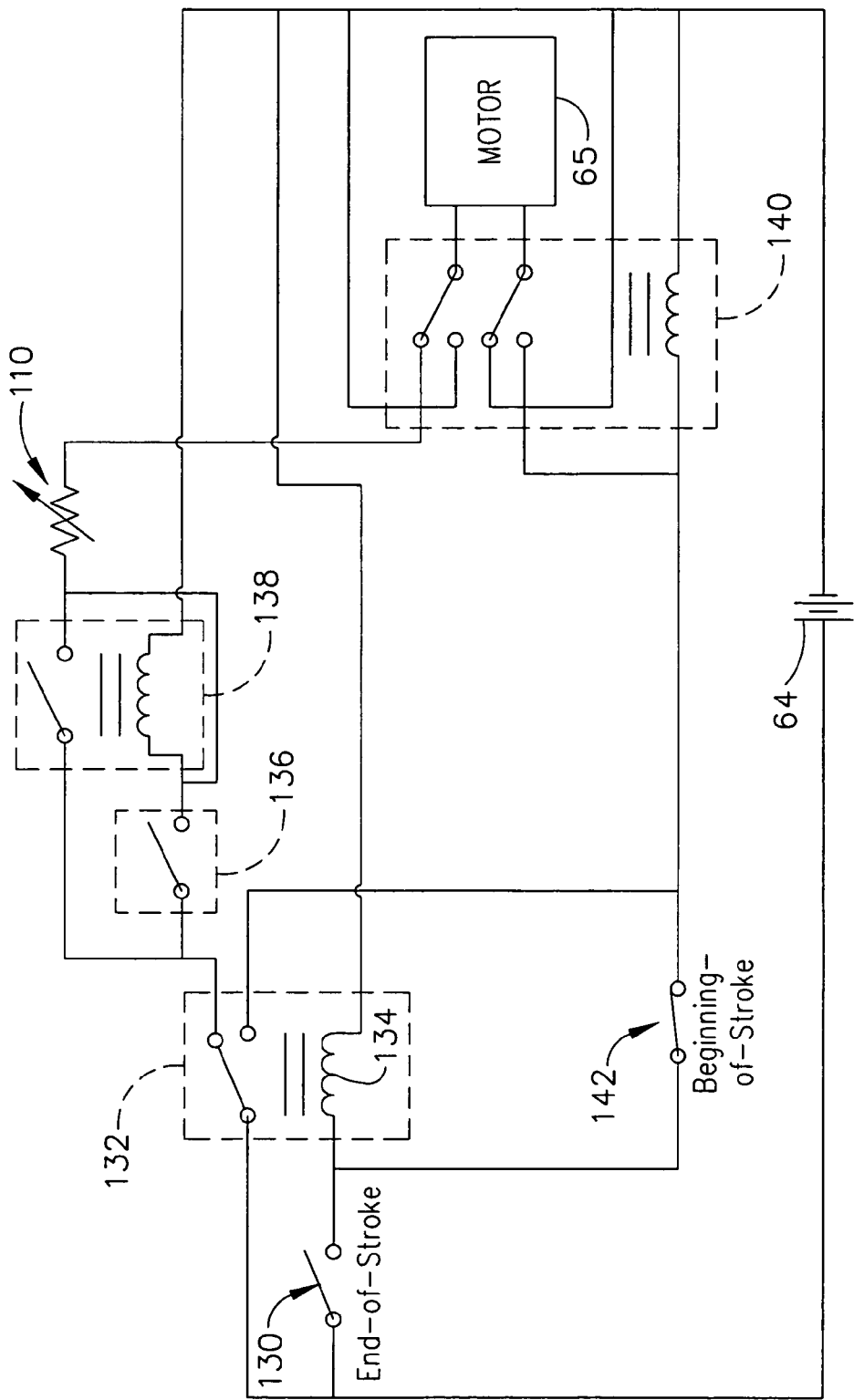
FIG. 11 is a schematic diagram of a circuit used in the instrument according to various embodiments.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow therethrough. If the normally-open reverse motor sensor switch 130 is open (meaning the end of the end effector stroke has not been reached), current will flow to a single pole, double throw relay 132. Since the reverse motor sensor switch 130 is not closed, the coil 134 of the relay 132 will not be energized, so the relay 132 will be in its non-energized state. The circuit also includes a cartridge lockout sensor switch 136. If the end effector 12 includes a staple cartridge 34, the sensor switch 136 will be in the closed state, allowing current to flow. Otherwise, if the end effector 12 does not include a staple cartridge 34, the sensor switch 136 will be open, thereby preventing the battery 64 from powering the motor 65.

When the staple cartridge 34 is present, the sensor switch 136 is closed, which energizes a single pole, single throw relay 138. When the relay 138 is energized, current flows through the relay 138, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 132. This causes the relay 132 to assume its energized state (not shown in FIG. 11), which causes current to bypass the cartridge lockout sensor switch 136 and variable resistor 110, and instead causes current to flow to both the normally-closed double pole, double throw relay 140 and back to the motor 65, but in a manner, via the relay 140, that causes the motor 65 to reverse its rotational direction.

Because the stop motor sensor switch 142 is normally-closed, current will flow back to the relay 132 to keep it energized until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
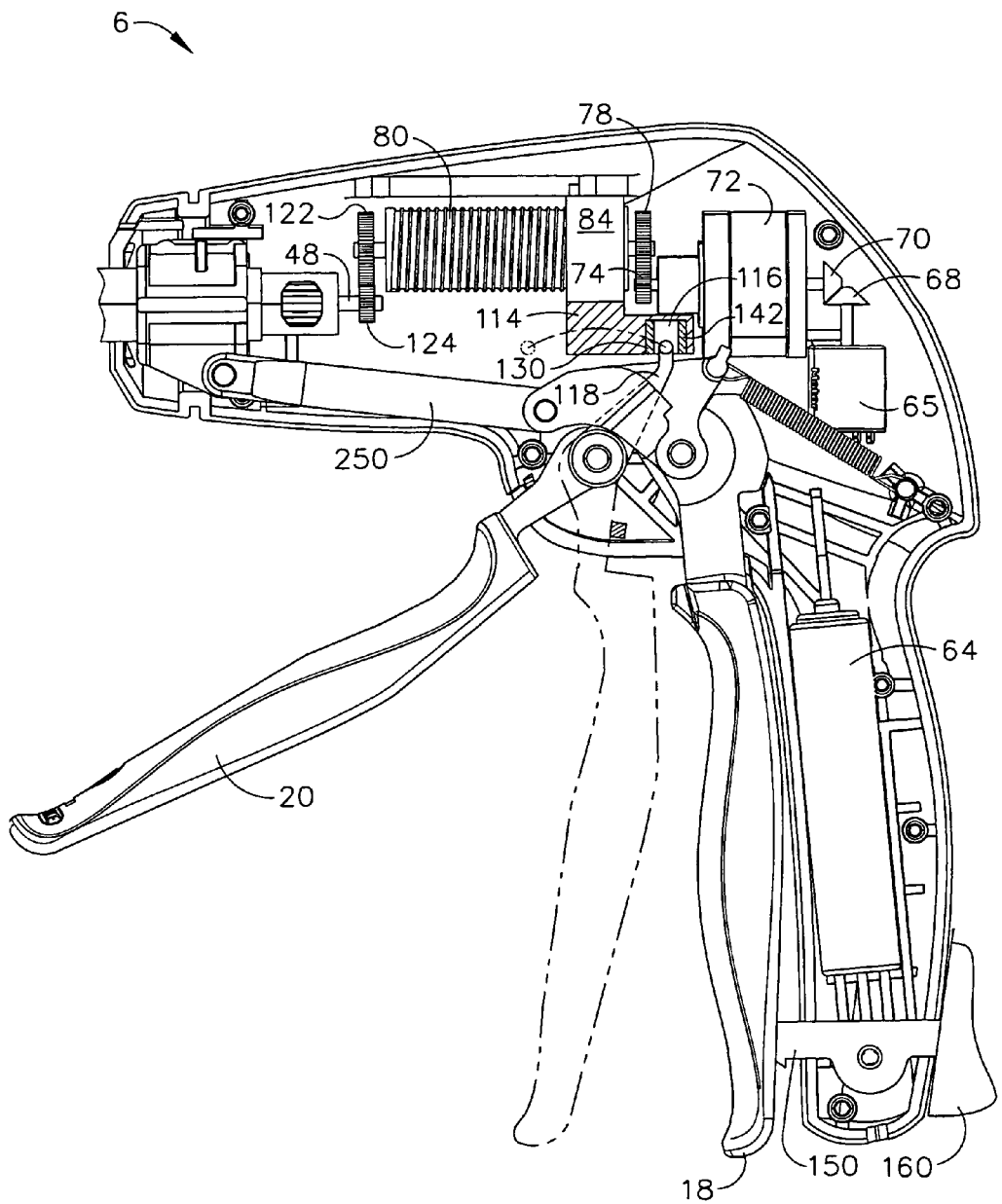
FIGS. 12-13 are side views of the handle according to various embodiments.

FIG. 12 is a side-view of the handle 6 of a power-assist motorized endocutter according to another embodiment. The embodiment of FIG. 12 is similar to that of FIGS. 7-10 except that in the embodiment of FIG. 12, there is no slotted arm 90 connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 116.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate CCW with the firing trigger 20 due to the forward motion stop 107 that engages the firing trigger 20. The CCW rotation of the middle piece 104 cause the arm 118 to rotate CCW with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm 118 will contact and thereby trip the stop motor sensor 142. Such actions may reverse and stop the motor 65, respectively, as described above.

Figure 13:
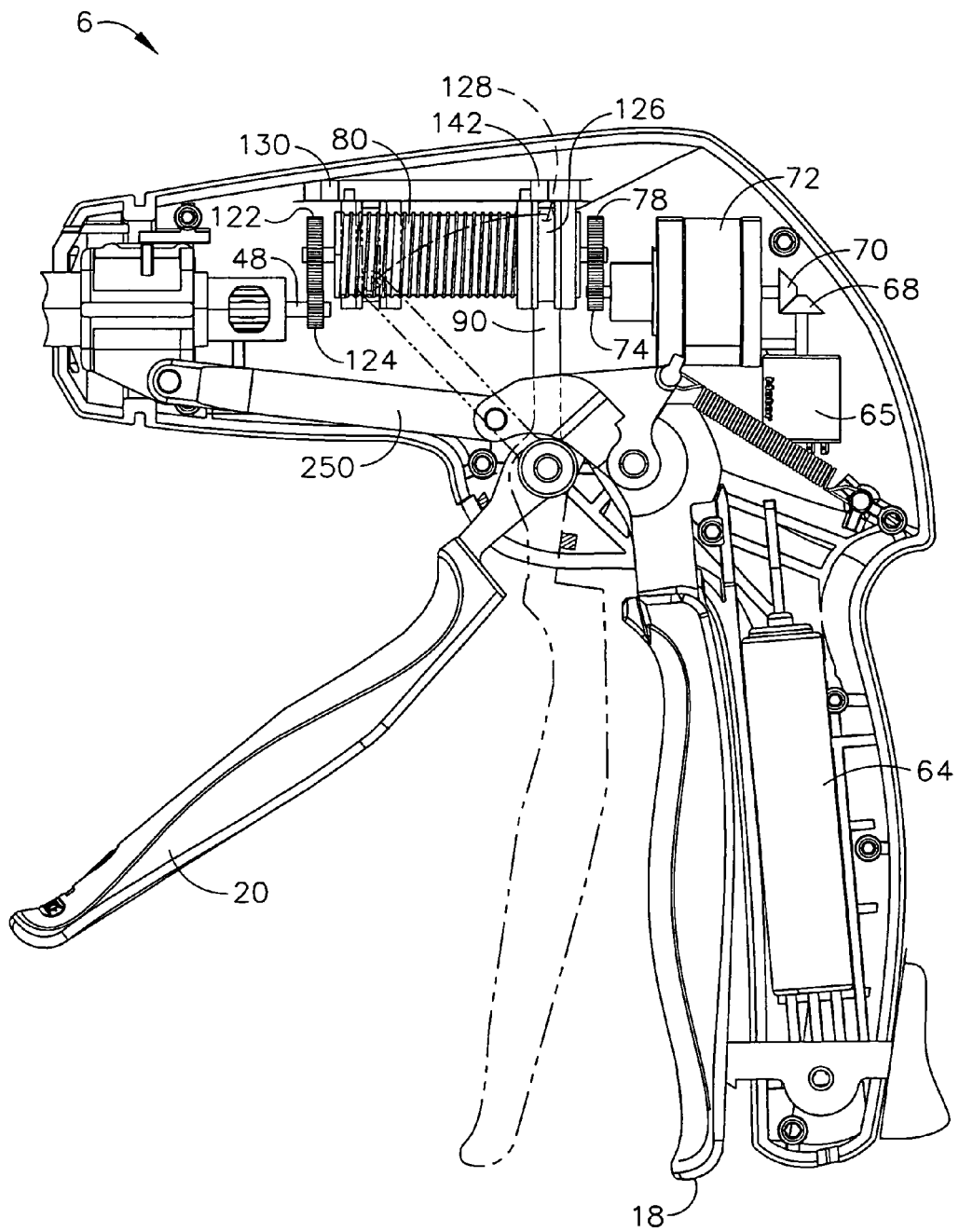

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates CCW as the ring 84 advances due to the post 128 being disposed in the channel 126, as shown in FIG. 13.

Figure 14:
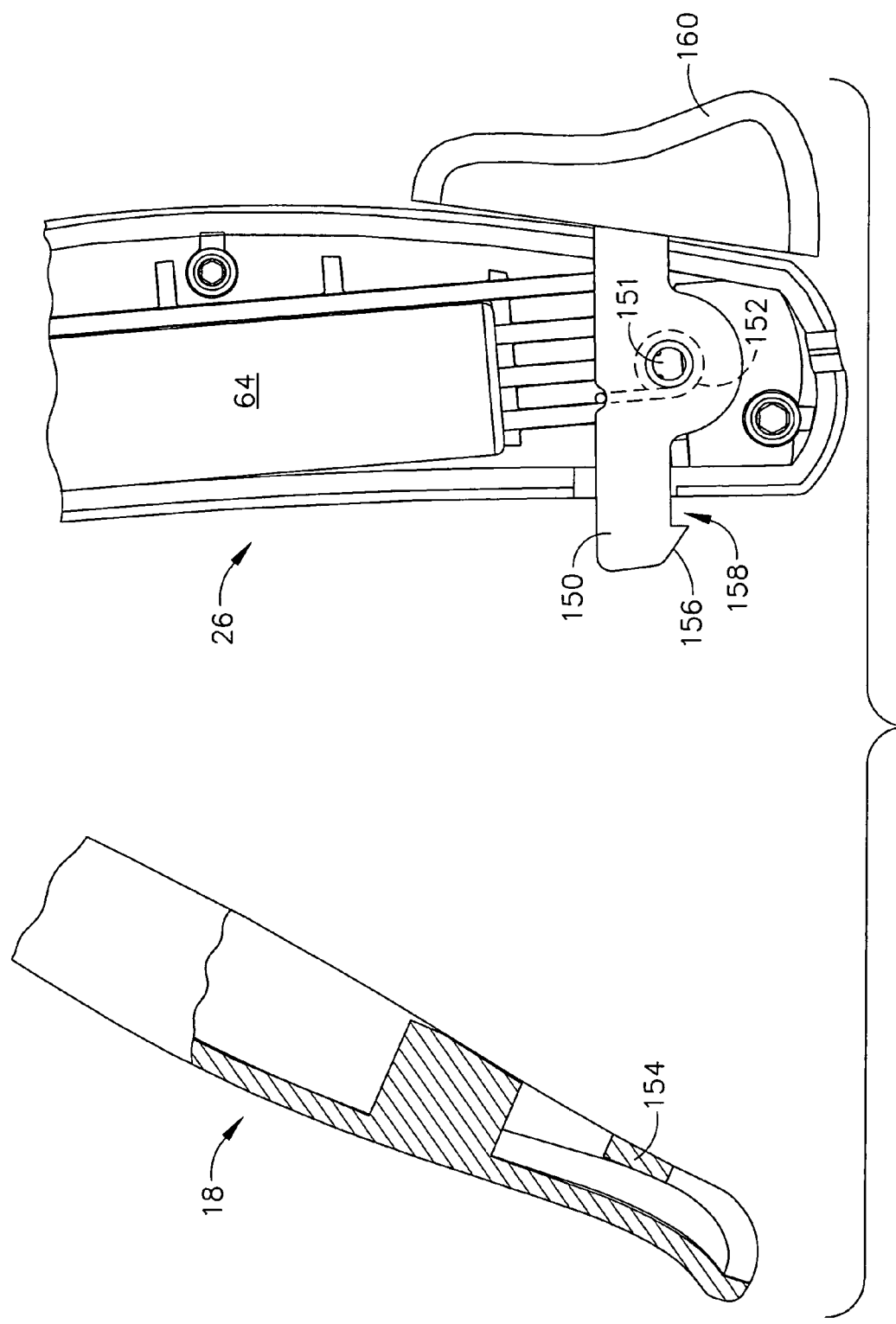
FIGS. 14-22 illustrate different mechanisms for locking the closure trigger according to various embodiments.
Figure 15:
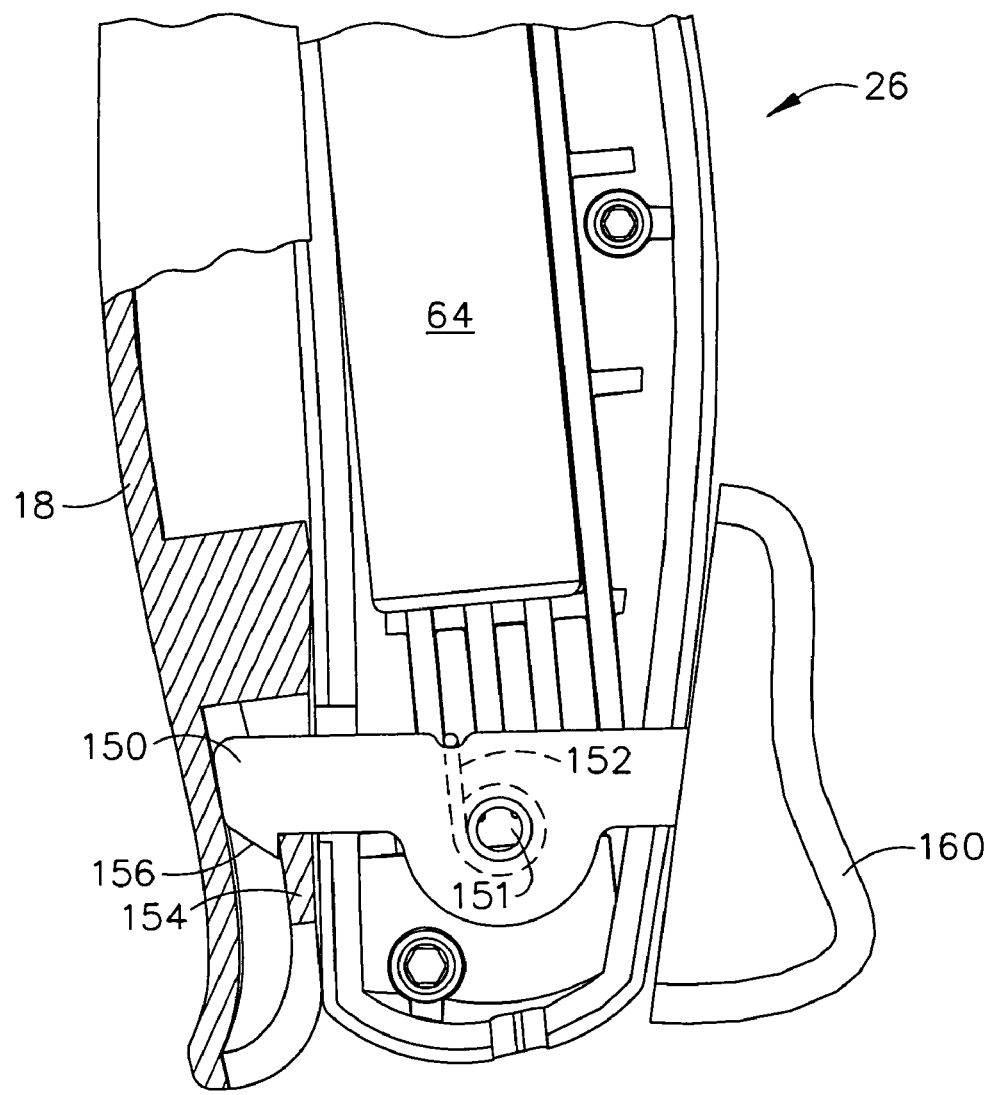

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 14-15) until the closure bar 154 completely passes the sloped portion 156 into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158.

Figure 16:
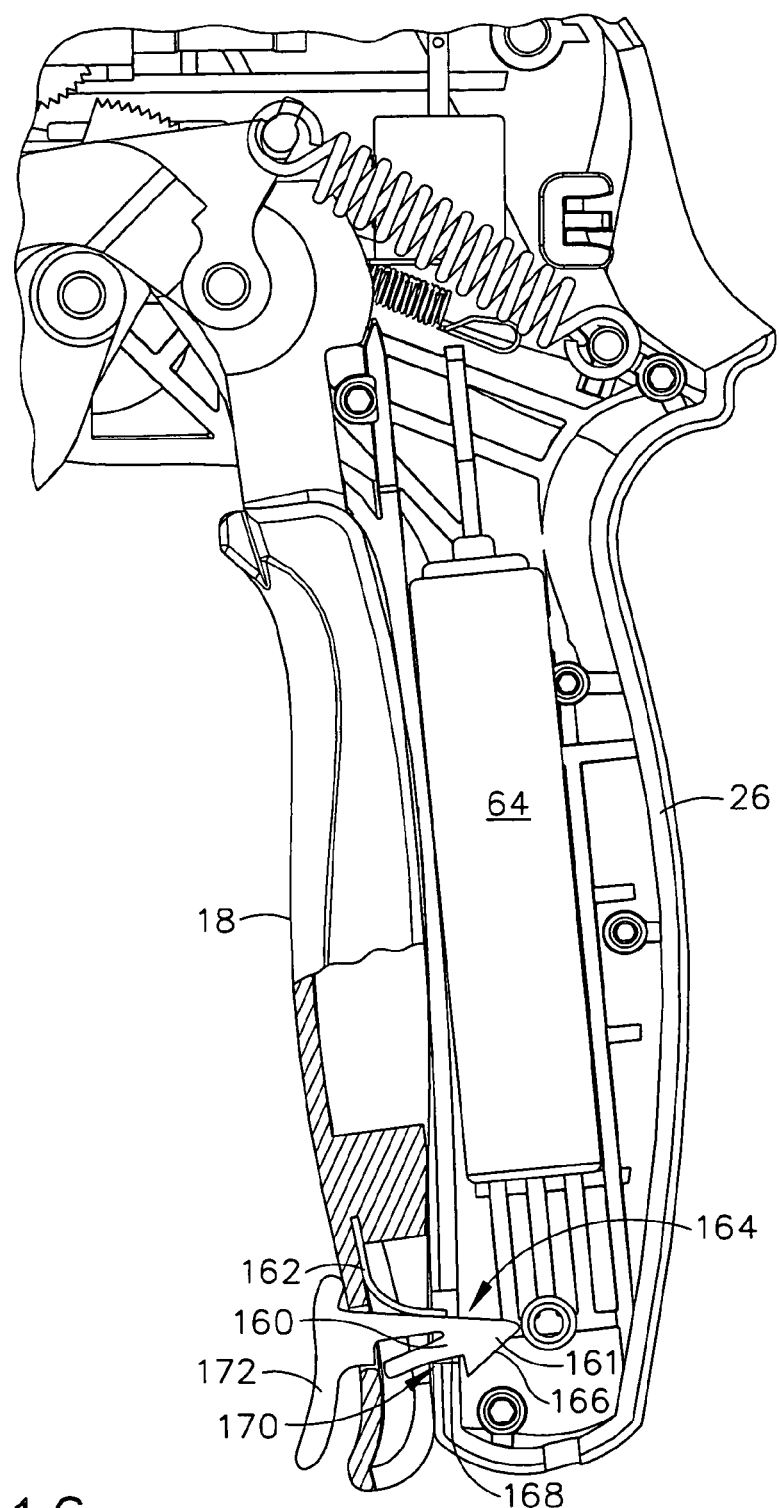

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or CW) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate CCW. Eventually the lower chamfered surface 166 fully passes the lower sidewall 168, removing the CCW force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate CCW and allowing the arrow-head portion 161 to slide out of the opening 164.

Figure 17:
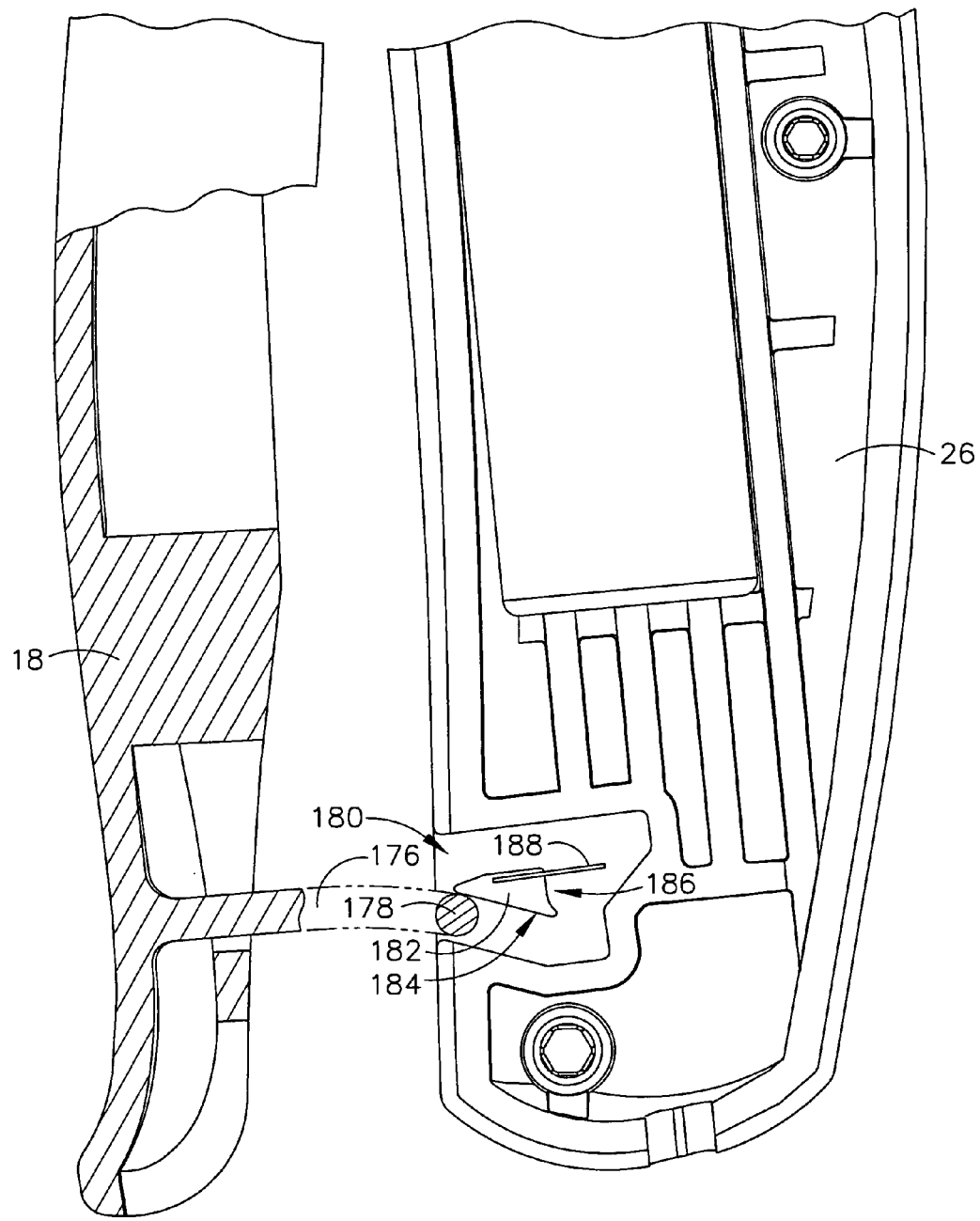
Figure 18:
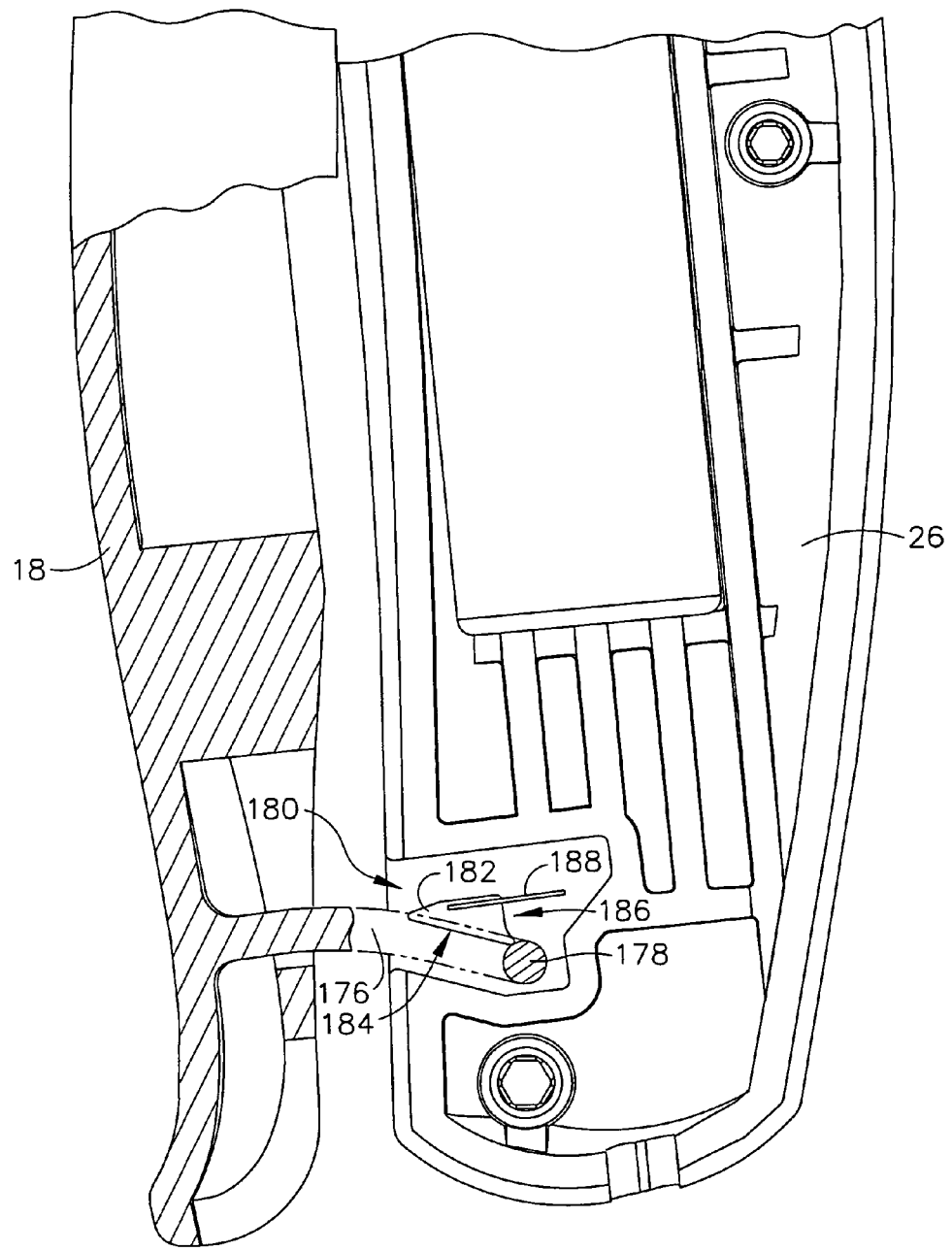
Figure 19:
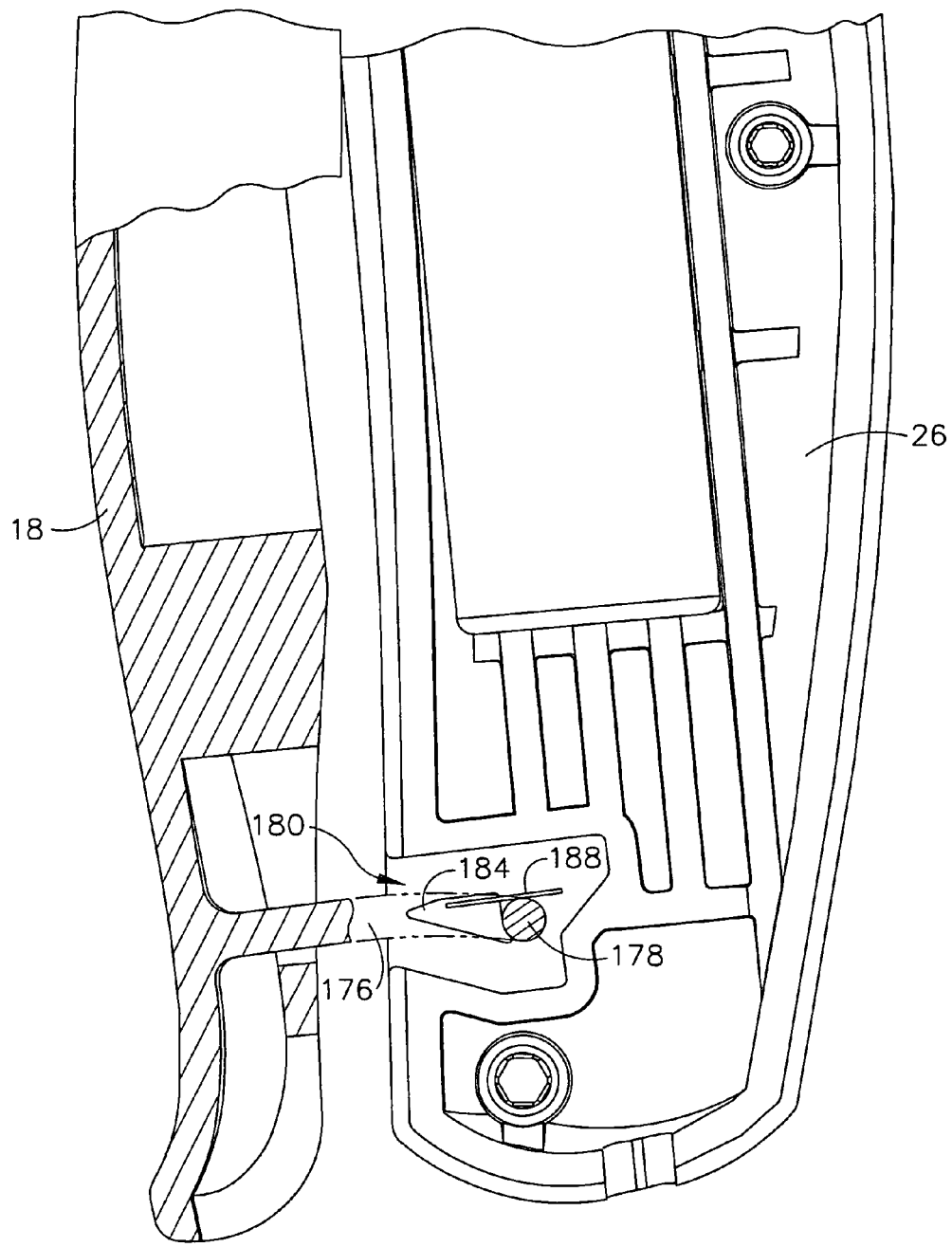

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated CW) by the lower surface 184 of the wedge 182, as shown in FIGS. 17 and 18. When the pin 178 fully passes the lower surface 184, the CW force on the arm 176 is removed, and the pin 178 is rotated CCW such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
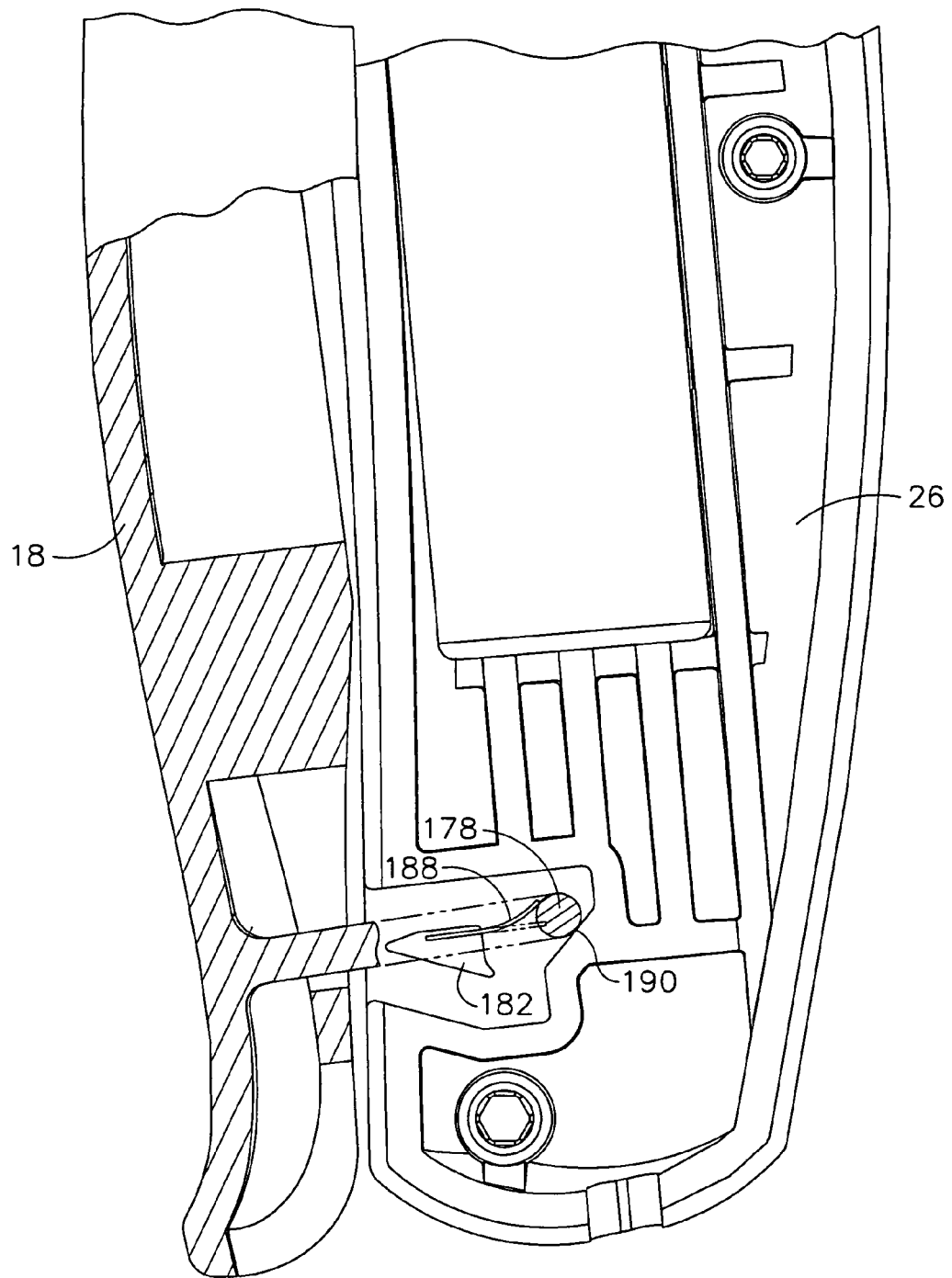
Figure 21:
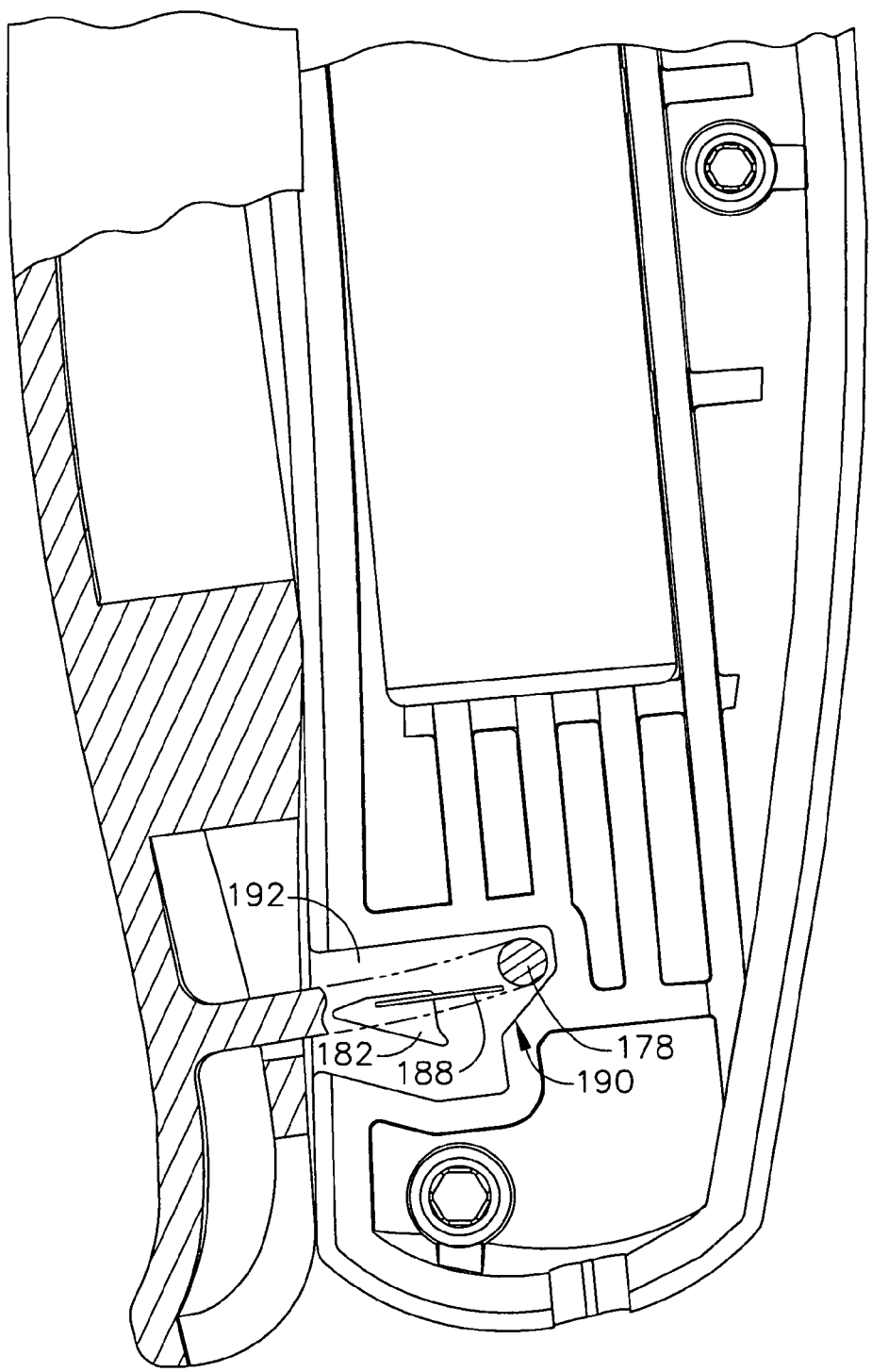
Figure 22:
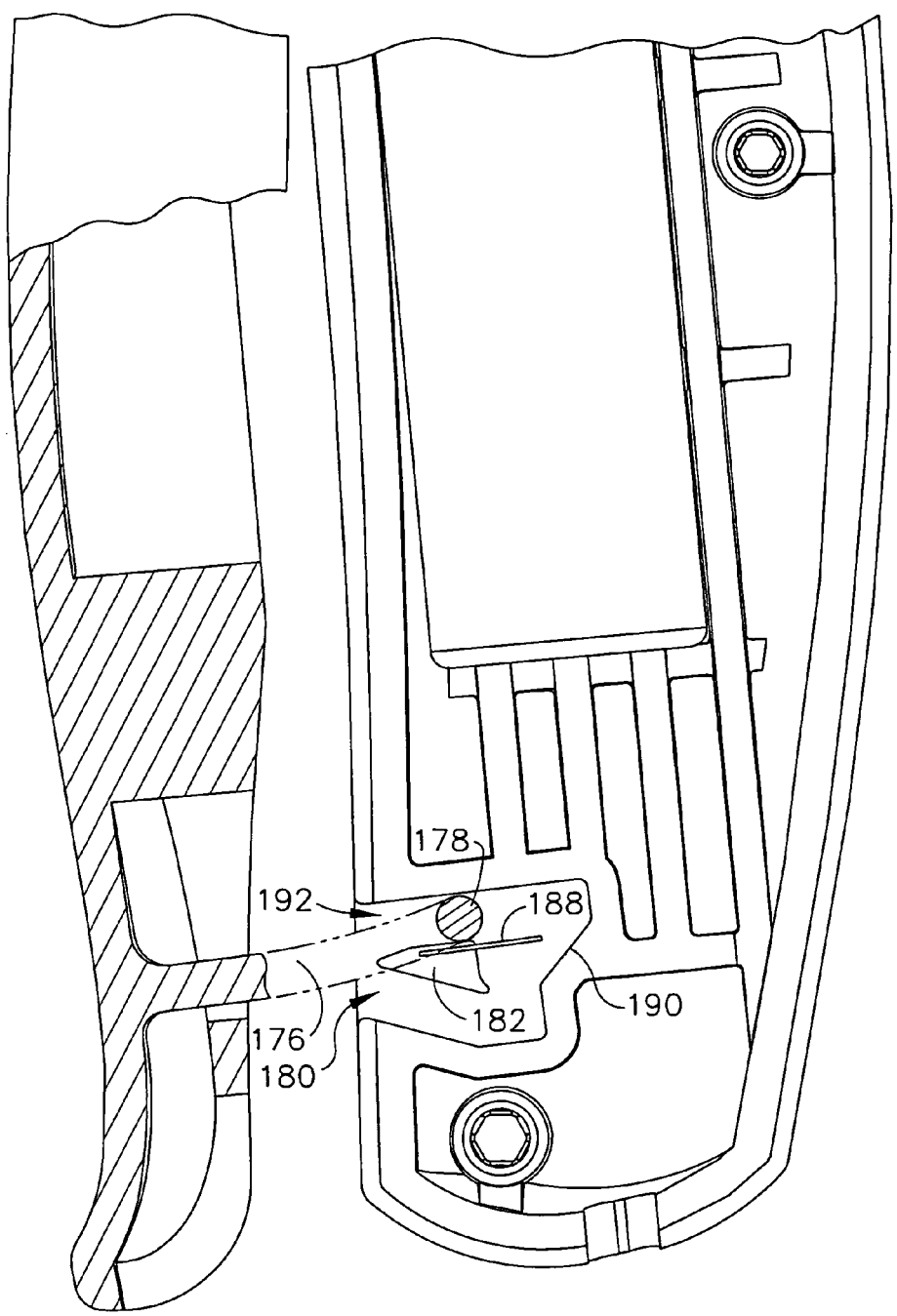
Figure 25:
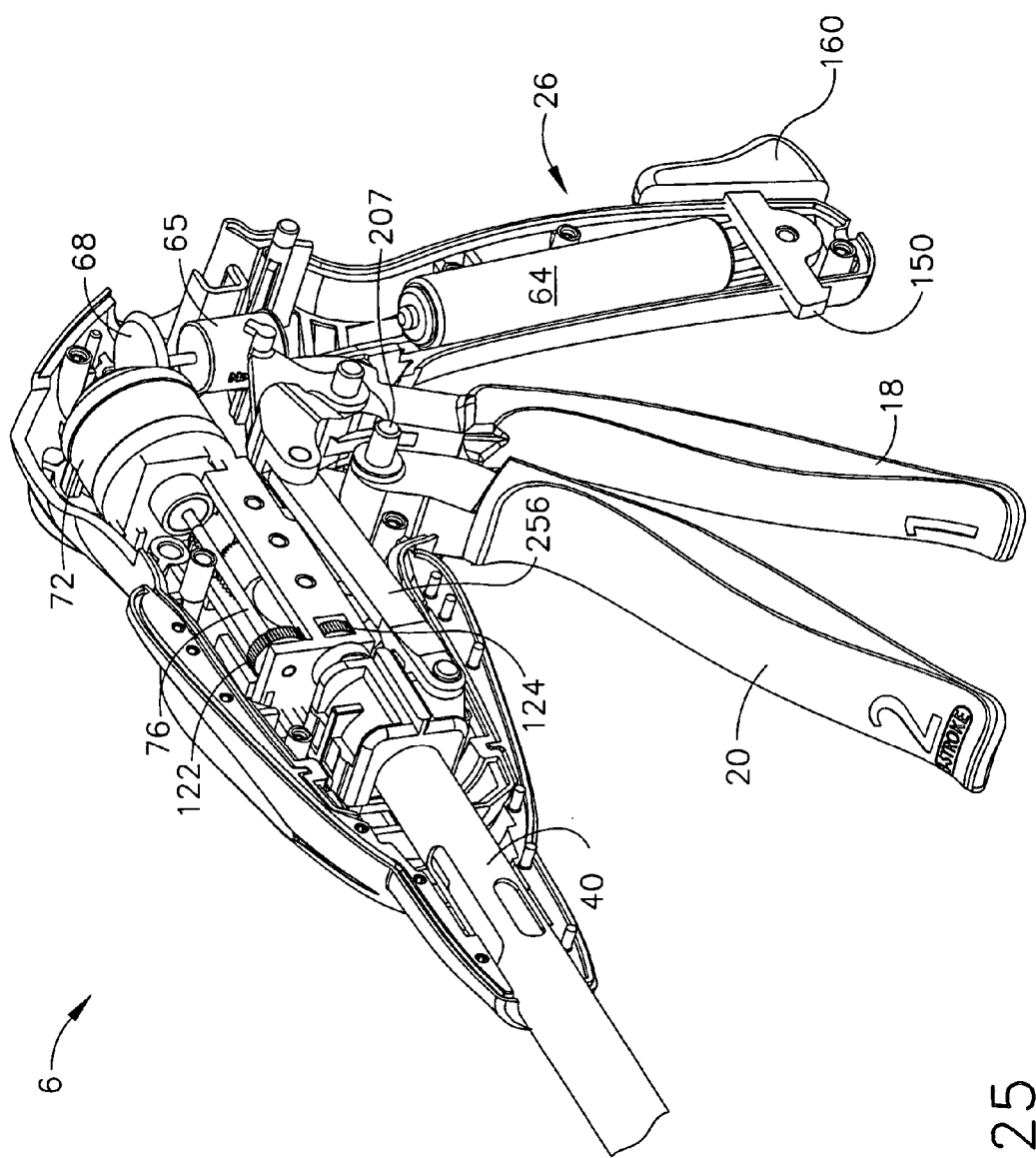
Figure 26:
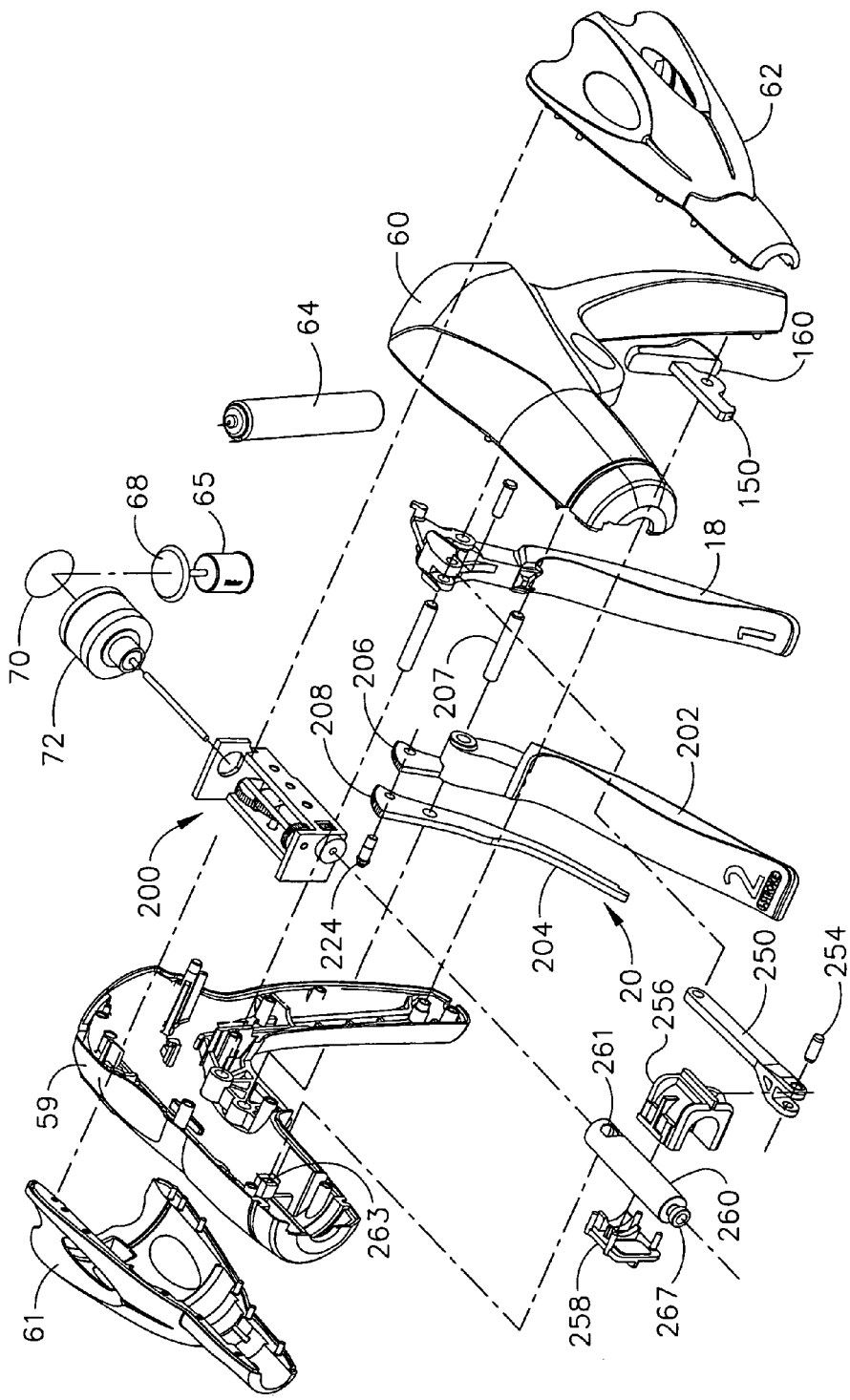
Figure 27:
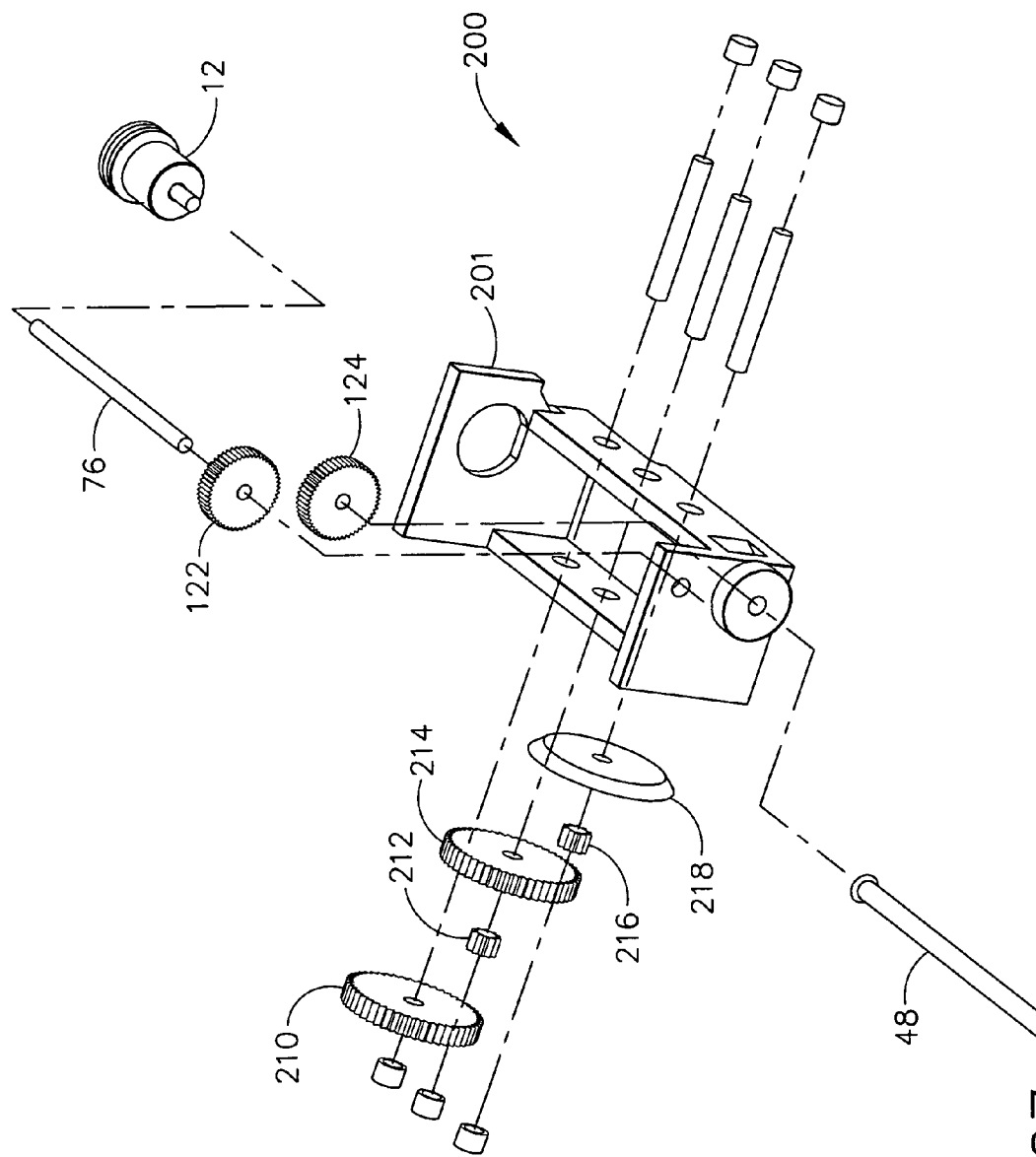
Figure 28:
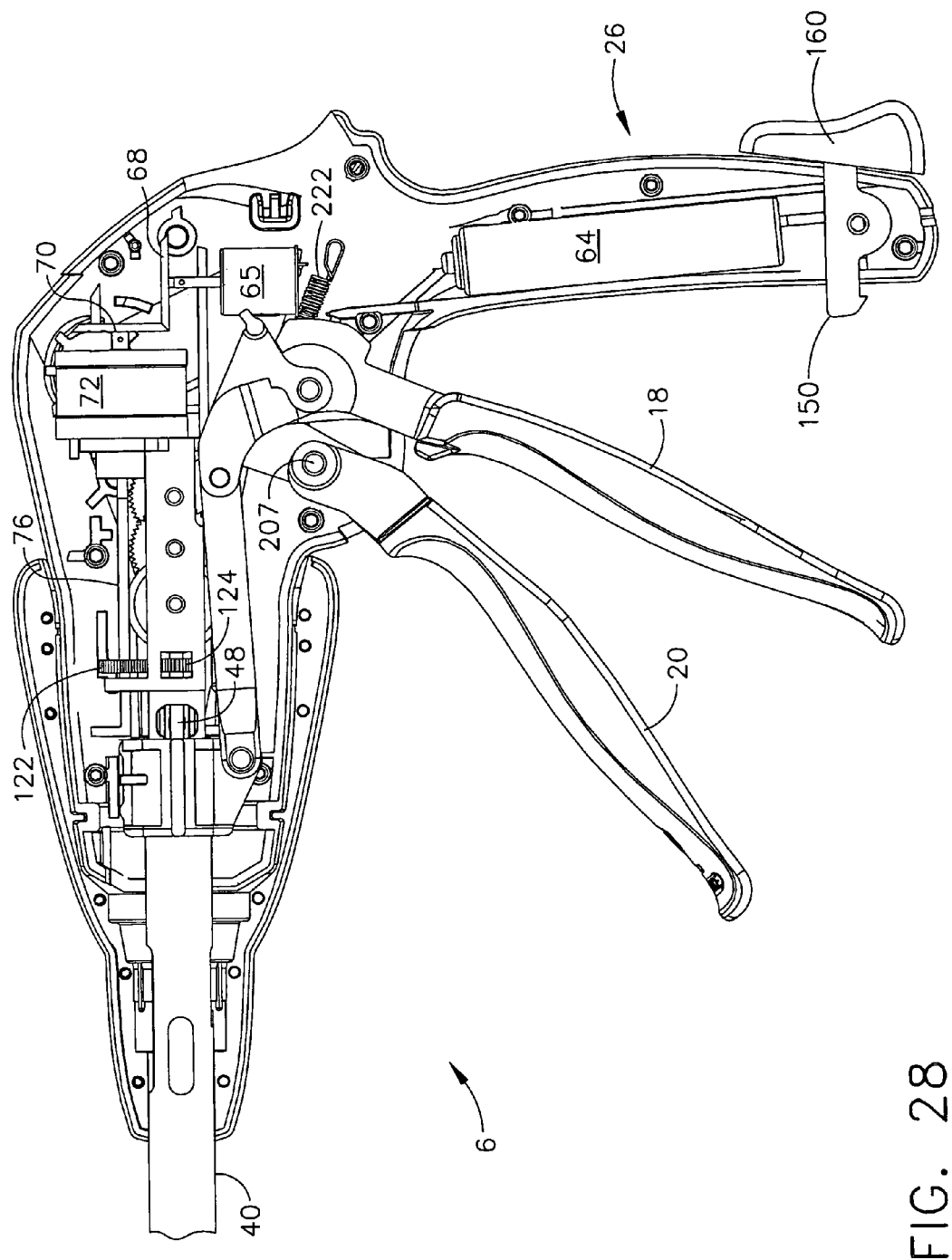
Figure 29:
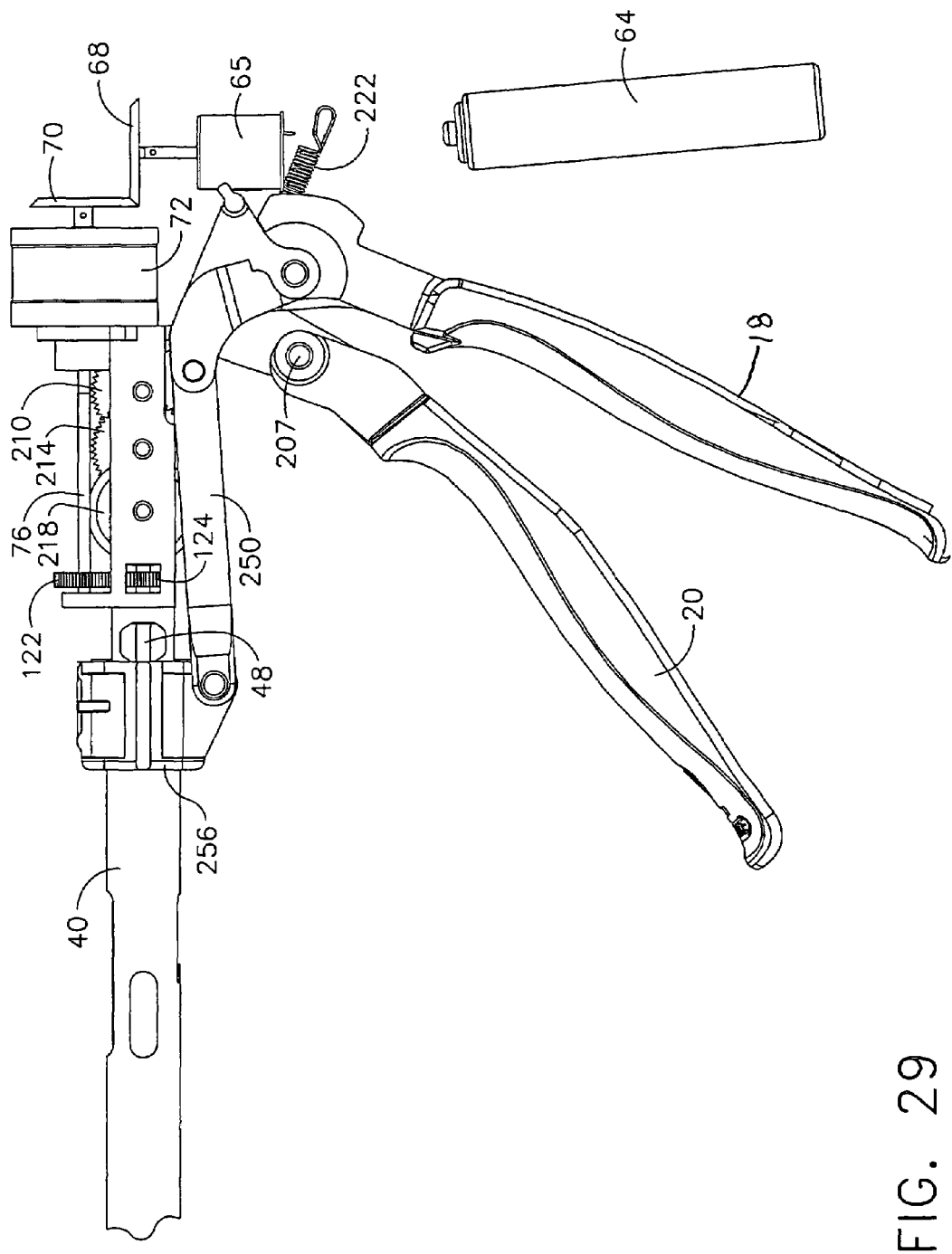
Figure 30:
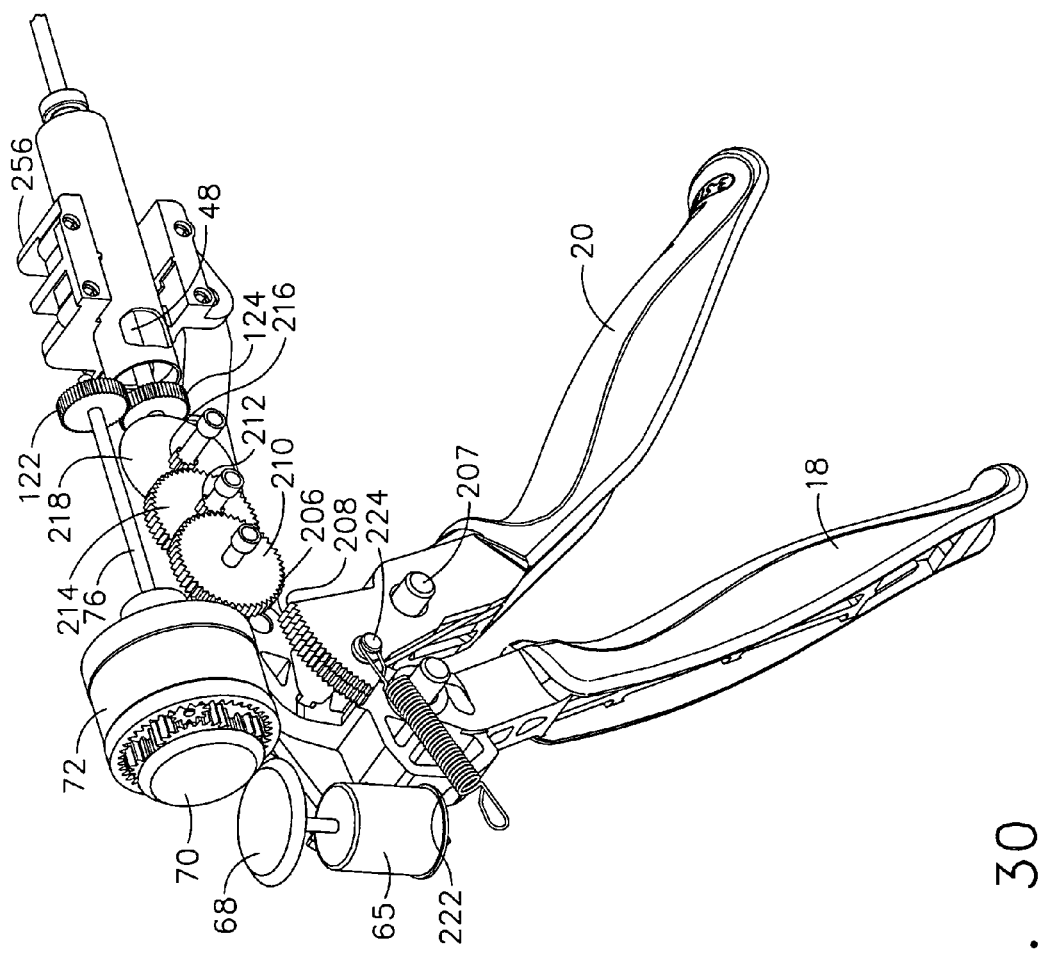
Figure 31:
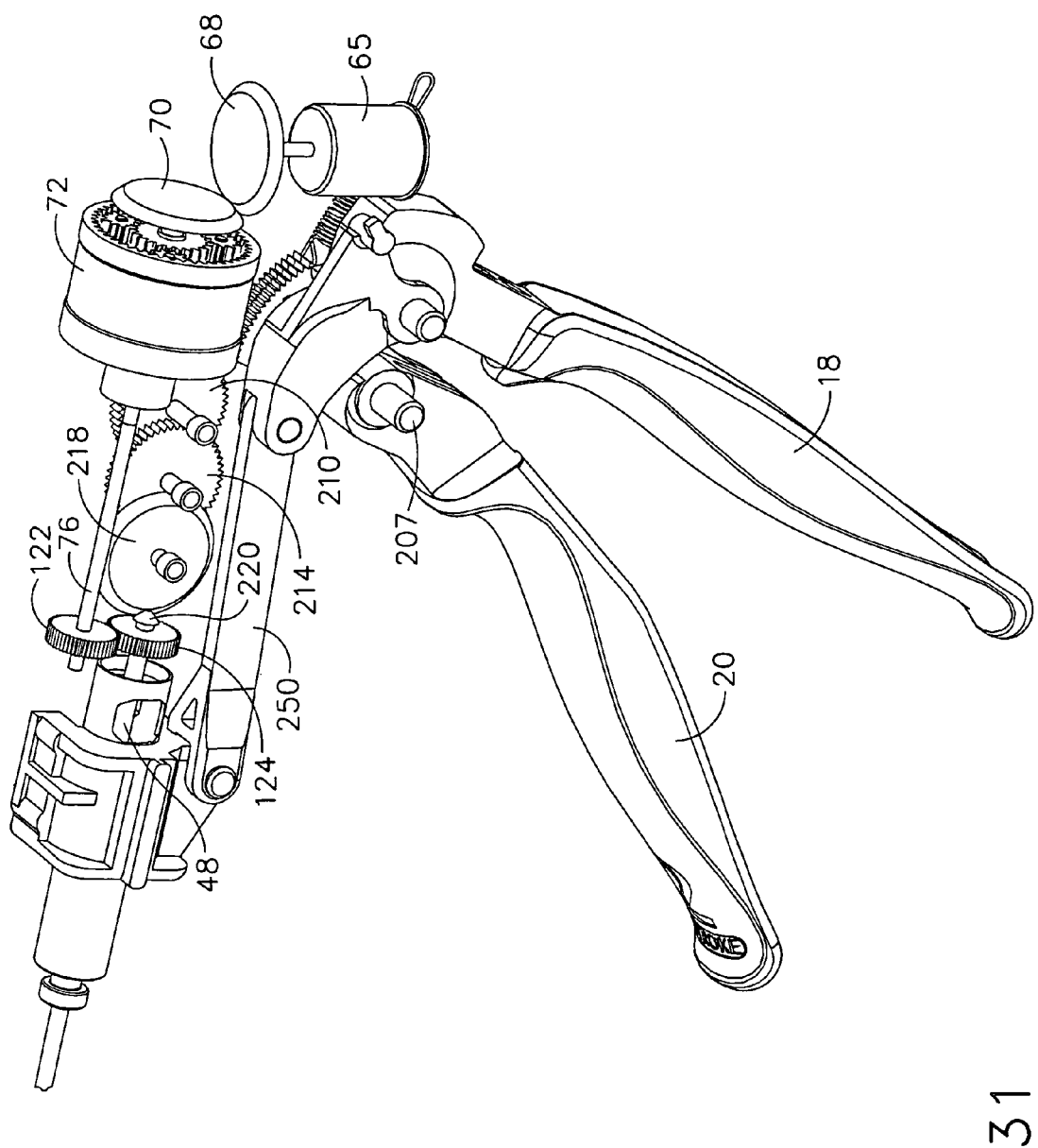

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist according to another embodiment of the present invention. The embodiment of FIGS. 25-31 is similar to that of FIGS. 6-10 except that instead of the helical gear drum 80, the embodiment of FIGS. 25-31 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximate end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 25-31 is another power assist, motorized instrument 10 that provides feedback to the user regarding the loading force experienced by the cutting instrument 32.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a CCW direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 include gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear 216 being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 66, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate CCW when the motor 65 provides forward drive for the end effector 12 (and to rotate CCW when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate CCW, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife 32 and sled 33) and the end of retraction operation (full retraction of the knife 32). A circuit similar to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the CW direction. The upper portion 230 may also include a lower arm 234 that contacts an upper surface of the lower portion 228 of the firing trigger 20 such that when the upper portion 230 is caused to rotate CW the lower portion 228 also rotates CW, and when the lower portion 228 rotates CCW the upper portion 230 also rotates CCW. Similarly, the lower portion 228 includes a rotational stop 238 that engages a lower shoulder of the upper portion 230. In that way, when the upper portion 230 is caused to rotate CCW the lower portion 228 also rotates CCW, and when the lower portion 228 rotates CW the upper portion 230 also rotates CW.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include a reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
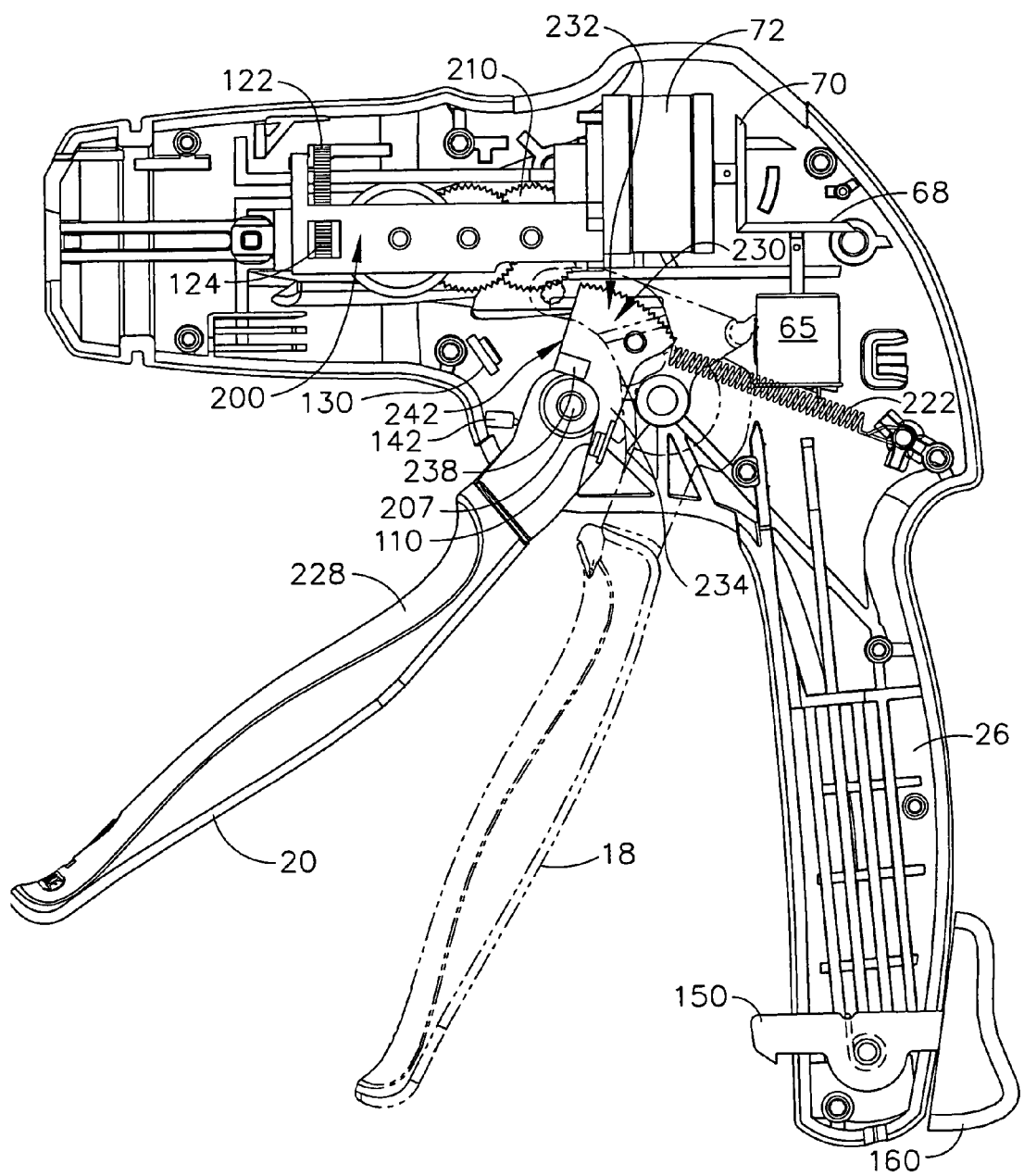
Figure 33:
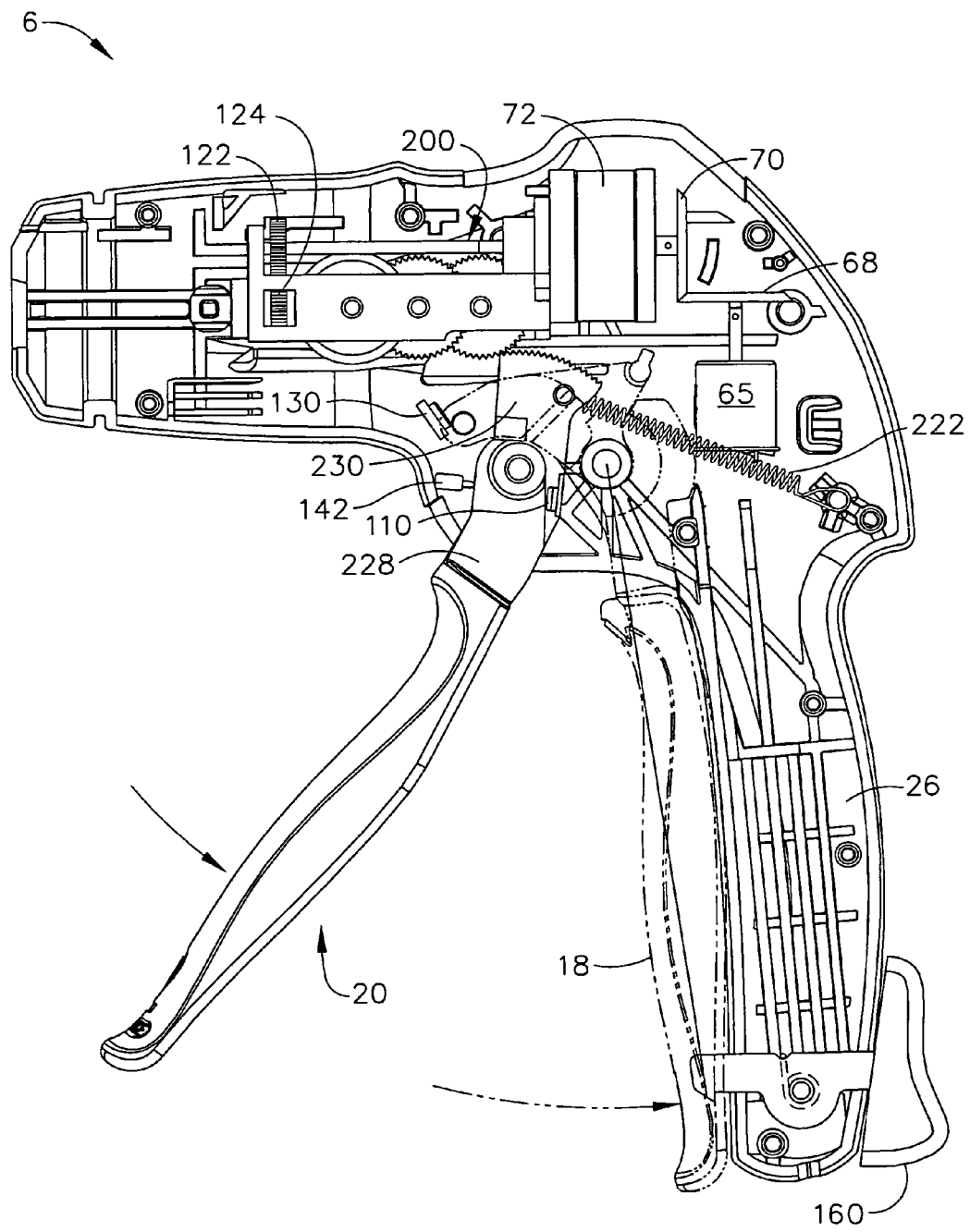
Figure 34:
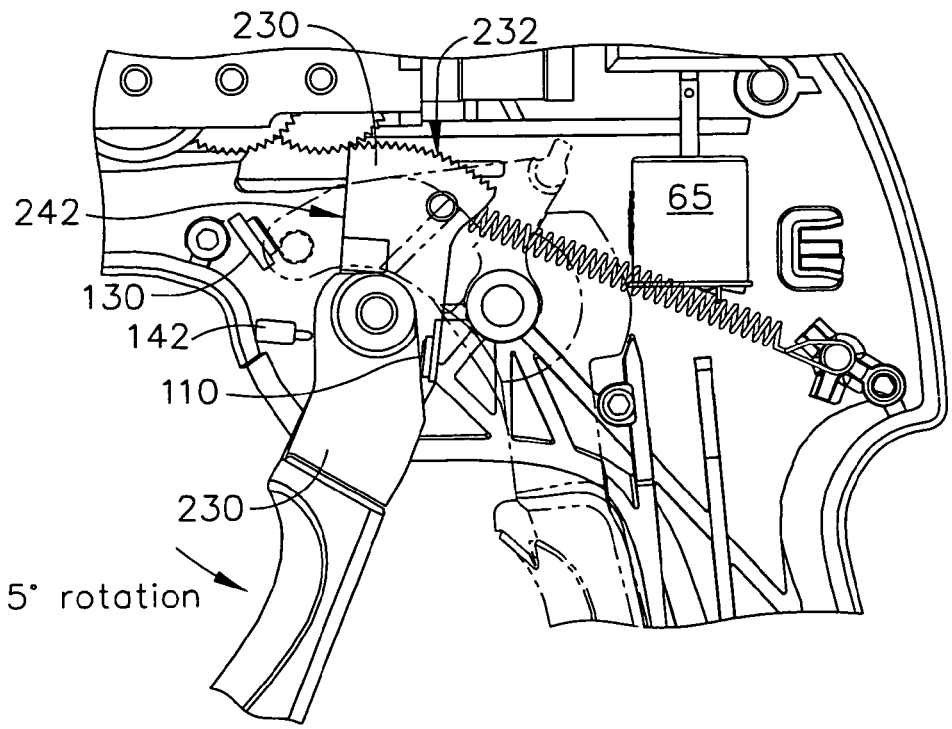
Figure 35:
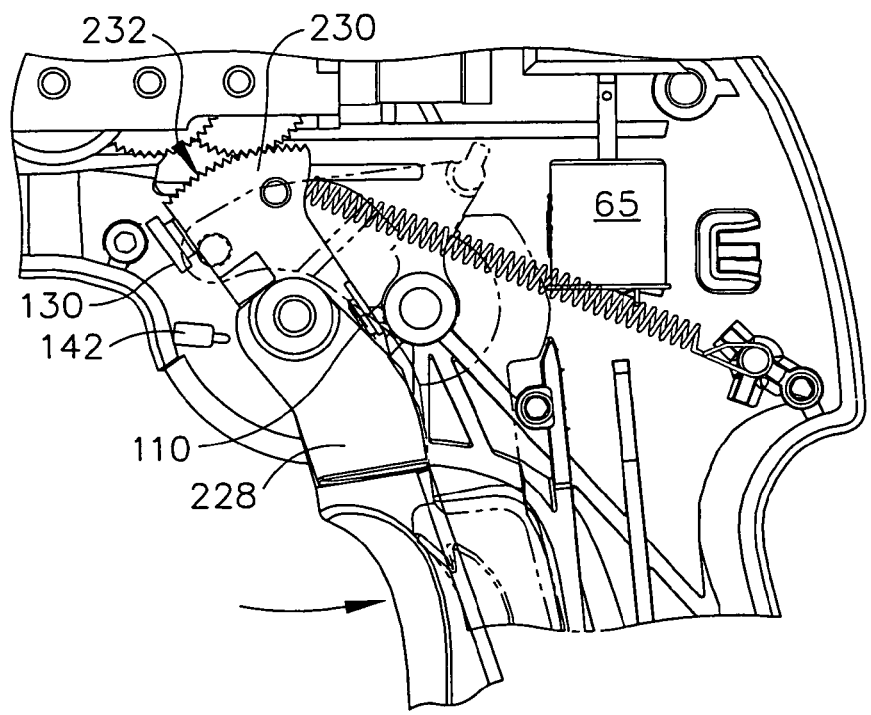
Figure 36:
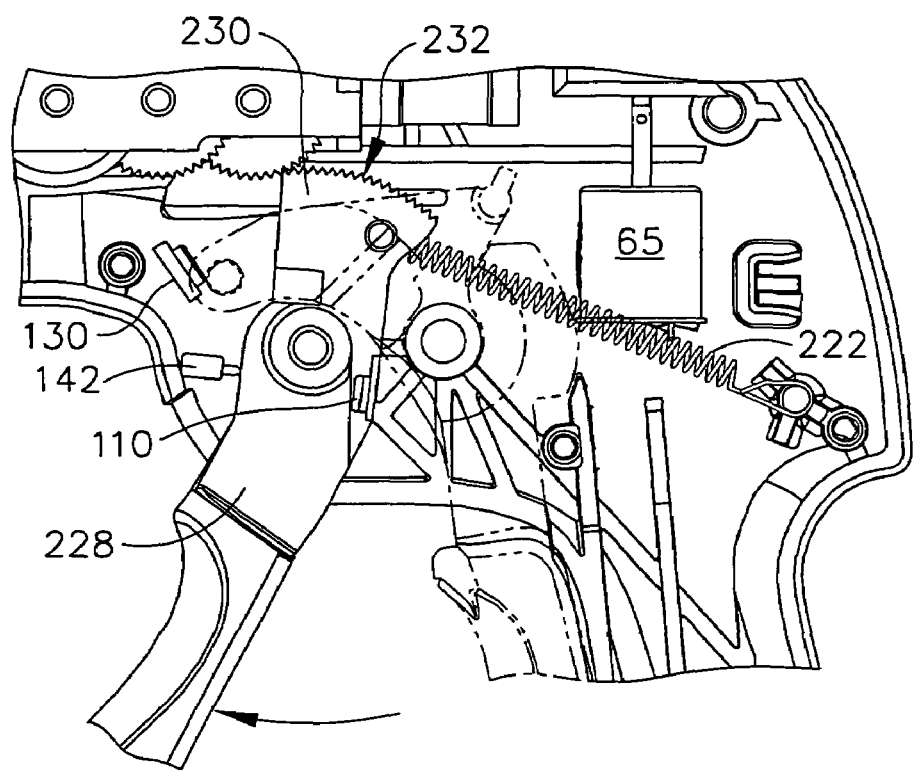

In operation, when an operator retracts the closure trigger 18 into the locked position, the firing trigger 20 is retracted slightly (through mechanisms known in the art, including U.S. Pat. No. 6,978,921, entitled "Surgical Stapling Instrument Incorporating An E-Beam Firing Mechanism" and U.S. Pat. No. 6,905,057, entitled "Surgical Stapling Instrument Incorporating A Firing Mechanism Having A Linked Rack Transmission," both of which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 230 is caused to rotate CCW, which causes the lower portion 228 to also rotate CCW.

When the knife 32 is fully deployed (i.e., at the end of the cutting stroke), the front face 242 of the upper portion 230 trips the reverse motor sensor 130, which sends a signal to the motor 65 to reverse rotational direction. This causes the main drive shaft assembly to reverse rotational direction to retract the knife 32. Reverse rotation of the main drive shaft assembly causes the gears 210-220 in the gear box assembly to reverse direction, which causes the upper portion 230 of the firing trigger 20 to rotate CW, which causes the lower portion 228 of the firing trigger 20 to rotate CW until the front face 242 of the upper portion 230 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate CCW, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor, gear drive train, and end effector) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments of the present invention, the user may be provided with tactile feedback regarding the position of the knife 32 in the end effector 12, but without having the firing trigger 20 geared into the gear drive train. FIGS. 37-40 illustrate a motorized surgical cutting and fastening instrument 10 with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument 10 includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
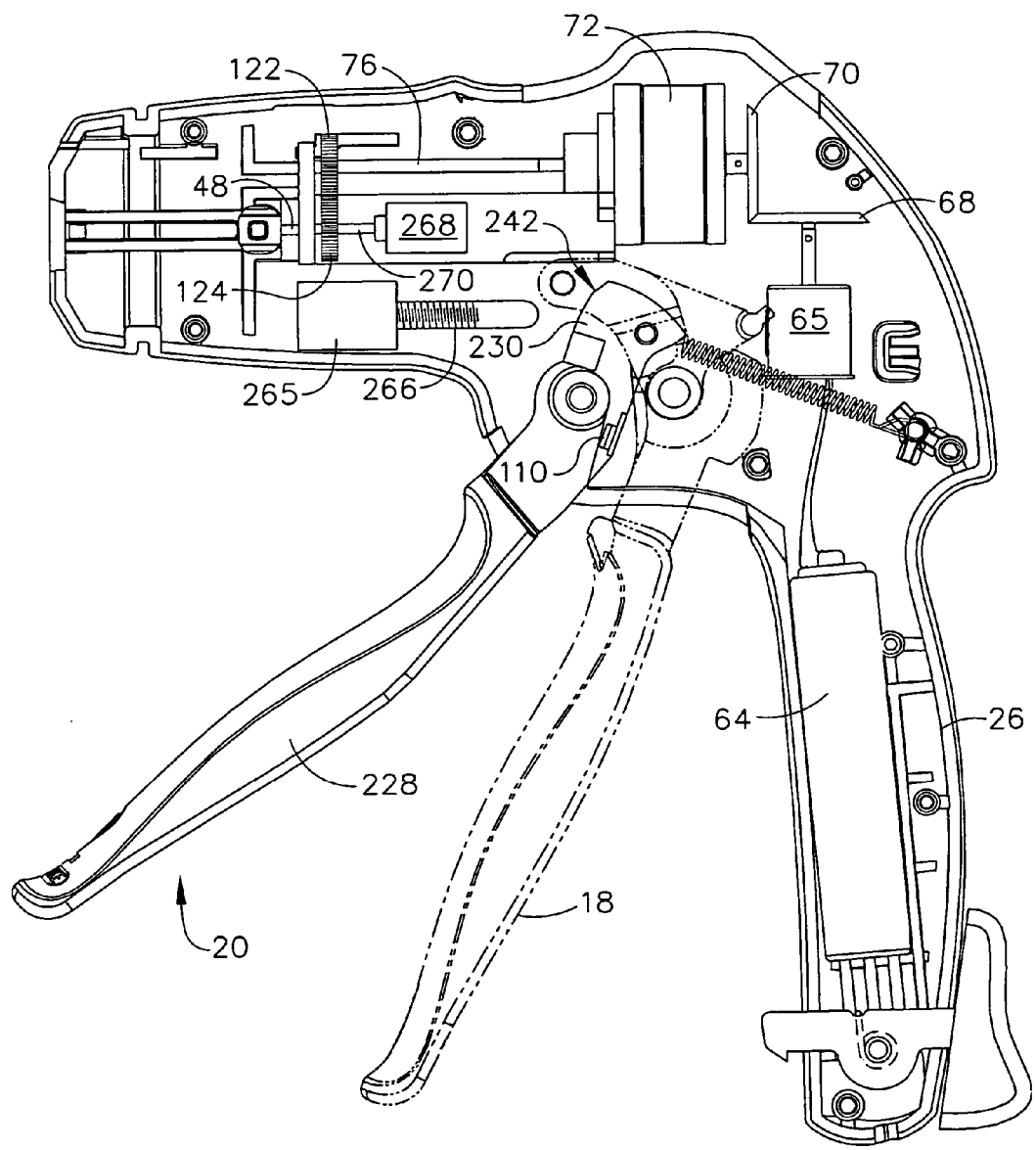
Figure 38:
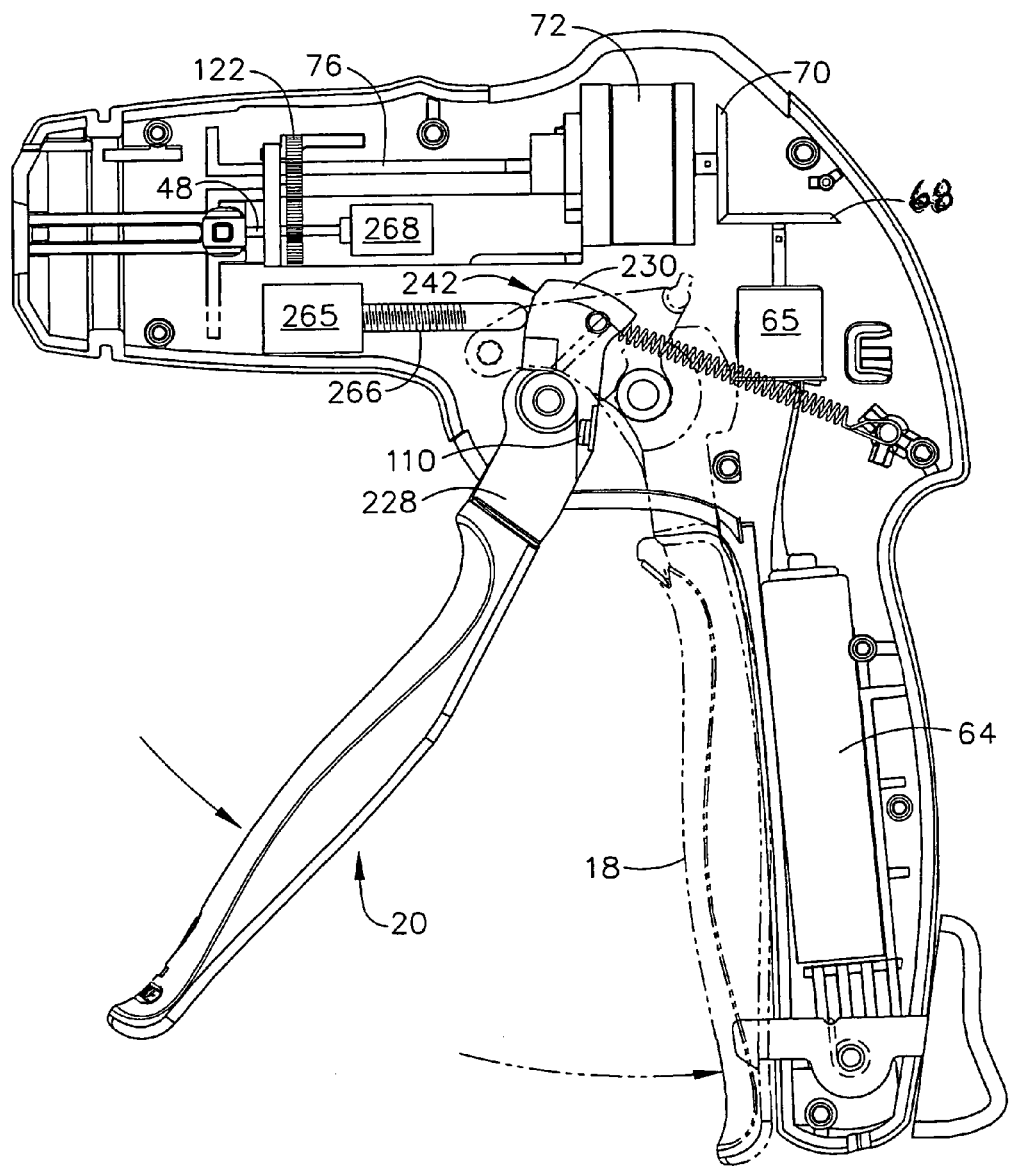
Figure 39:
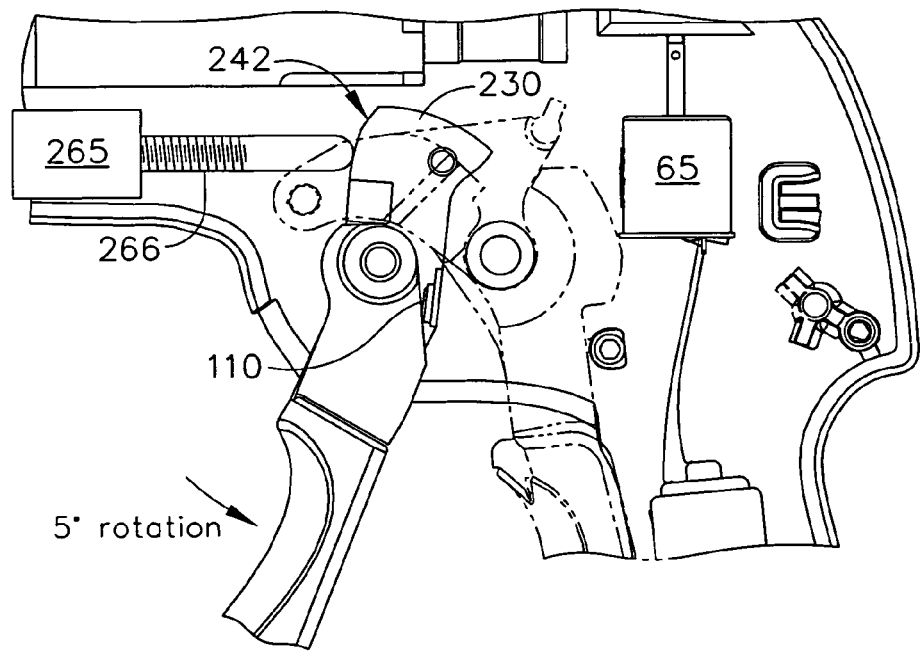
Figure 40:
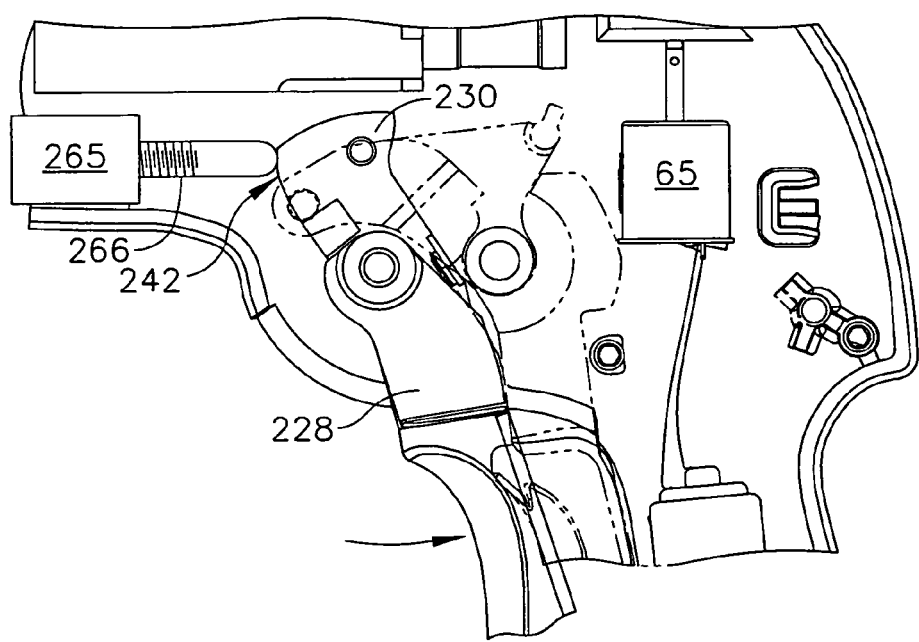

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 18 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g., 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to cause the second motor 265 to rotate, which causes the threaded rod 266 to retract into the motor 265. This allows the upper portion 230 of the firing trigger 20 to rotate CCW, which allows the lower portion 228 of the firing trigger to also rotate CCW. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate CW, which causes the lower portion 228 to rotate CW. In that way, the operator may experience a CW force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

FIG. 43 illustrates various embodiments of a surgical instrument 300. The surgical instrument 300 may be similar to the surgical instrument 10 described hereinabove. In these embodiments, the handle 6 comprises a primary portion 302 and a grip portion 304 that is releasably connected to the primary portion 302. The grip portion 304 may be engaged with the primary portion 302 by any suitable arrangement. For example, according to various embodiments, the engagement of the grip portion 304 to the primary portion 302 may be realized by a straight linear slide arrangement as shown, for example, in FIG. 44, by an arrangement that requires rotation of the grip portion 304 and/or the primary portion 302 to finalize the engagement, etc.

According to various embodiments, the grip portion 304 may comprise the pistol grip 26, a portion of exterior side piece 59, and a portion of exterior side piece 60 described hereinabove. According to various embodiments, the primary portion 302 may comprise the rest of the handle 6. As shown, for example, in FIGS. 48 and 49, the grip portion 304 further comprises first and second upper slide rails 306 and first and second lower slide rails 308. As shown in FIG. 44, the first upper slide rail 306 defines a ramp 310. The relationship between the first upper slide rail 306 and the first lower slide rail 308 is shown in FIG. 44.

Although the battery 64 is shown in FIG. 43 as being within the grip portion 304, it is understood that according to other embodiments the battery 64 may be within the primary portion 302. According to various embodiments, the grip portion 304 is structured and arranged to allow the battery 64 to be removed from the grip portion 304. For example, the grip portion 304 may include a removable portion that covers an opening sized to allow the battery 64 to be removed from the grip portion 304. Alternatively, the portion of the exterior side piece 59 may be disconnected from the portion of the exterior side piece portion 60 to allow easy access to the battery 64 for separate disposal. According to various embodiments, the battery 64 may be a rechargeable battery.

Although the motor 65 is shown in FIG. 43 as being within the primary portion 302, it is understood that according to other embodiments the motor 65 may be within the grip portion 304. The motor 65 is in electrical communication with the battery 64 via conductors 314. Although only conductors 314 are shown in FIG. 43, as will described in more detail hereinbelow, according to other embodiments, the electrical communication path between the battery 64 and the motor 65 may also include one or more motor interlocks.

The surgical instrument 300 may further comprise a lockout system 316 within the handle 6. The lockout system 316, shown in greater detail, for example, in FIGS. 44 and 47, is structured and arranged to block connection of the grip portion 304 to the primary portion 302 after the grip portion 304 is disconnected from the primary portion 302 a predetermined number of times. The predetermined number of times may be any number of times. For example, according to various embodiments, the lockout system 316 may block connection of the grip portion 304 to the primary portion 302 after the grip portion 304 is disconnected from the primary portion 302 two times. Although the lockout system 316 is shown predominately within the primary portion 302, it is understood that according to other embodiments the lockout system 316 may be predominately within the grip portion 304.

As shown in FIG. 44, the lockout system 316 comprises a counter 318, and a blocking assembly 320 coupled to the counter 318. The counter 318 is structured and arranged to advance when the grip portion 304 is disconnected from the primary portion 302 of the handle 6. The counter 318 is connected to a shaft 322 (shown more clearly in FIGS. 46 and 47) which is supported by a boss 323 (shown in FIGS. 46 and 47) connected to the primary portion 302. The counter 318 comprises an index wheel 324 couped to the shaft 322, and a biasing member 326 coupled to the index wheel 324. The biasing member 326 may be embodied, for example, by a torsion spring configured to bias the index wheel 324 in a counterclockwise direction.

The index wheel 324 defines protrusions 328 that cooperate with the blocking assembly 320 to limit the advancement of the index wheel 324. One of the protrusions 328 is structured and arranged to cooperate with the blocking assembly 320 to block connection of the grip portion 304 to the primary portion 302 after the grip portion 304 is disconnected from the primary portion 302 a predetermined number of times. Although the index wheel 324 is shown as defining protrusions 328, it is understood that according to other embodiments, the index wheel 324 may define indents that cooperate with the blocking assembly 320 to limit the advancement of the index wheel 324, and one of the indents may cooperate with the blocking assembly 320 to block connection of the grip portion 304 to the primary portion 302 after the grip portion 304 is disconnected from the primary portion 302 a predetermined number of times.

The shaft 322 is structured and arranged to permit the index wheel 324 to be reset to a previous position. For example, the shaft may define a hexagonal shaped opening 330, and a hexagonal shaped tool may be inserted through an opening 331 defined by the primary portion 302 (shown in FIG. 47) and into the hexagonal shaped opening 330, then rotated in clockwise direction to reset the index wheel 324 to a previous position.

The blocking assembly 320 is structured and arranged to block connection of the grip portion 304 to the primary portion 302 after the grip portion 304 is disconnected from the primary portion 302 a predetermined number of times. As shown in FIG. 44, the blocking assembly 320 comprises a blocking member 332, a blocking member guide 334, a gate member 336, and a biasing member 338. The blocking member 332 is structured and arranged to block connection of the grip portion 304 to the primary portion 302 after the grip portion 304 is disconnected from the primary portion 302 a predetermined number of times. The blocking member guide 334 is connected to the primary portion 302 (shown more clearly in FIGS. 46 and 47), is in contact with the blocking member 332, and serves to guide movement of the blocking member 332. The gate member 336 is in contact with the blocking member 332, is pivotably connected to the blocking member guide 334, and cooperates with the protrusions 328 to limit the advancement of the index wheel 324. The biasing member 338 is coupled to the gate member 336. The biasing member 338 may be embodied, for example, by a torsion spring configured to bias the gate member 336 in a clockwise direction. The operation of the lockout system 316 will be described in more detail hereinbelow with respect to FIGS. 50-55.

As shown, for example, in FIGS. 44, 45 and 47, the handle 6 further comprises a release system 340 structured and arranged to initiate disengagement of the grip portion 304 from the primary portion 302. The release system 340 is within the primary portion 302 and comprises a release button 342, and first and second release members 344 connected to or integral with the release button 342. The first and second release members 344 each define a release ramp 346. The release system 340 further comprises first and second release pins 348 in contact with the respective release ramps 346, first and second lock springs 350 in contact with the first and second release pins 348, and first and second ejection springs 352 (shown more clearly in FIG. 49) in contact with the first and second lower slide rails 308.

To initiate the disengagement of the grip portion 304 from the primary portion 302, the release button 342 is advanced, causing the first and second release members 344 and the respective release ramps 346 to also advance. As the release ramps 346 advance, the release ramps 346 cause the first and second release pins 348 to change position. The change of the respective positions of the first and second release pins 348 causes the first and second lock springs 350 to change position. Once the first and second lock springs 350 change their respective positions enough to allow the first and second upper slide rails 306 to pass thereby, each of the first and second ejection springs 352 release stored energy, thereby respectively imparting a force against each of the the first and second lower slide rails 308. The imparted force assists the disengagement of the grip portion 304 from the primary portion 302. It is understood that, according to other embodiments, the release system 340 may comprise other components and/or configurations suitable for initiating the release of the grip portion 304 from the primary portion 302.

Figure 50:
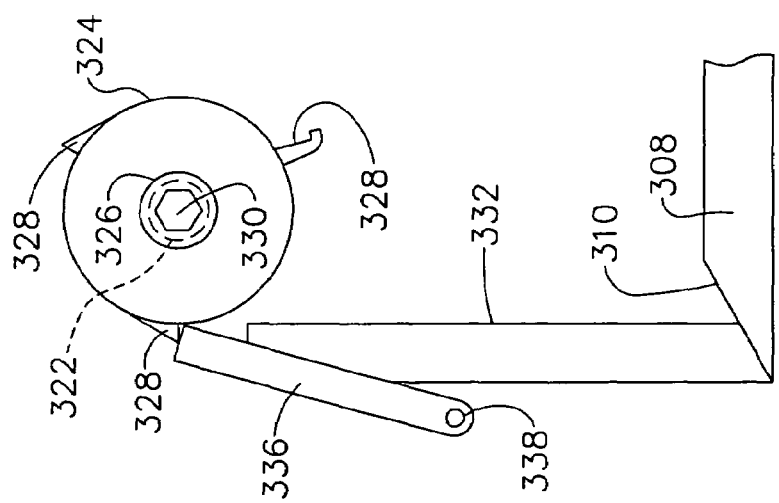

FIGS. 50-55 illustrate the relative positions of the components of the lockout system 316 at various times during the attachment/disconnect process. FIG. 50 illustrates the relative positions prior to the first full engagement of the grip portion 304 to the primary portion 302. The gate member 336 is in contact with one of the protrusions 328, thereby preventing the index wheel 324 from advancing.

Figure 51:
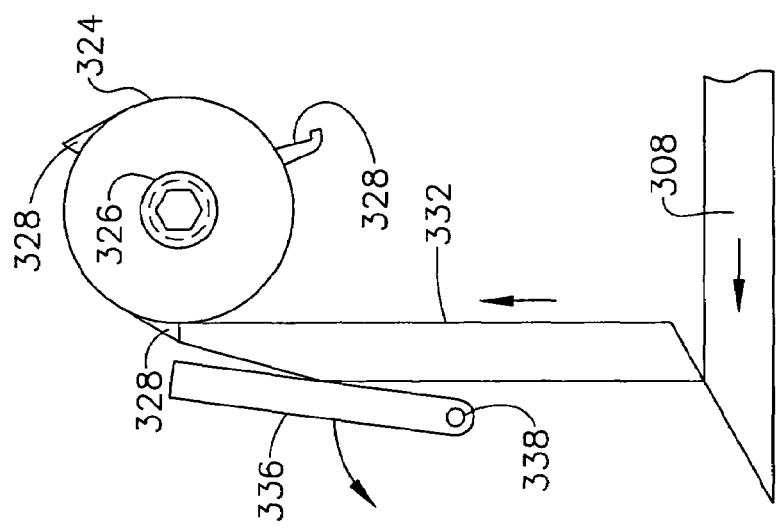

As the first and second upper slide rails 306 advance, the ramp 310 defined by the first upper slide rail 306 causes the blocking member 332 to advance toward the index wheel 324. As the blocking member 332 advances toward the index wheel 324, the blocking member 332 causes the gate member 336 to advance away from the index wheel 324. As the first upper slide rail 306 and the ramp 310 continue to advance, the blocking member 332 continues to advance toward the index wheel 324. When the grip portion 304 is fully engaged with the primary portion 302, the blocking member 332 is in contact with the protrusion 328 that was initially in contact with the gate member 336, thereby preventing the index wheel 324 from advancing as shown in FIG. 51.

Figure 52:
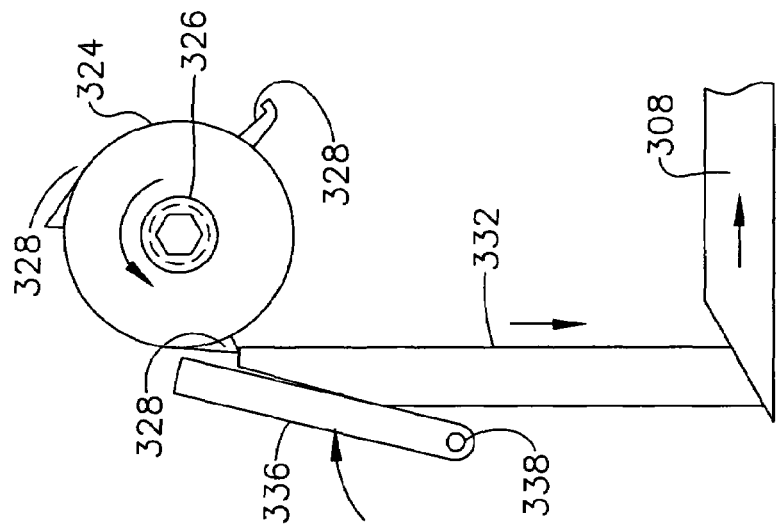
Figure 53:
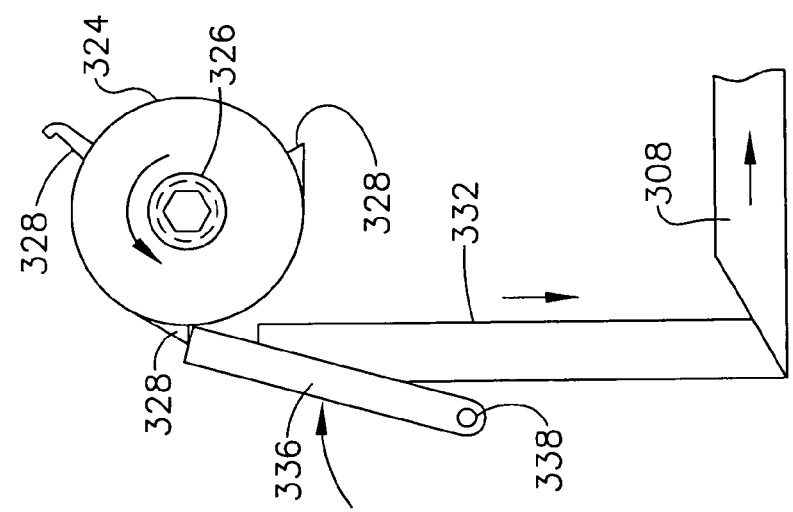

After the disengagement of the grip portion 304 from the primary portion 302 is initiated, the first and second upper slide rails 306 advance in the opposite direction, the ramp 310 defined by the first upper slide rail 306 allows the blocking member 332 to advance away from the index wheel 324. As the blocking member 332 advances away from the index wheel 324, the blocking member 332 allows the gate member 336 to advance toward the index wheel 324 and past the protrusion 328 as shown in FIG. 52. As the grip portion 304 is disconnected from the primary portion 302, the blocking member 332 advances far enough away from the index wheel 324 to lose contact with the protrusion 328 and allow index wheel 324 to rotate until a second protrusion 328 comes into contact with the gate member 336 as shown in FIG. 53.

Figure 55:
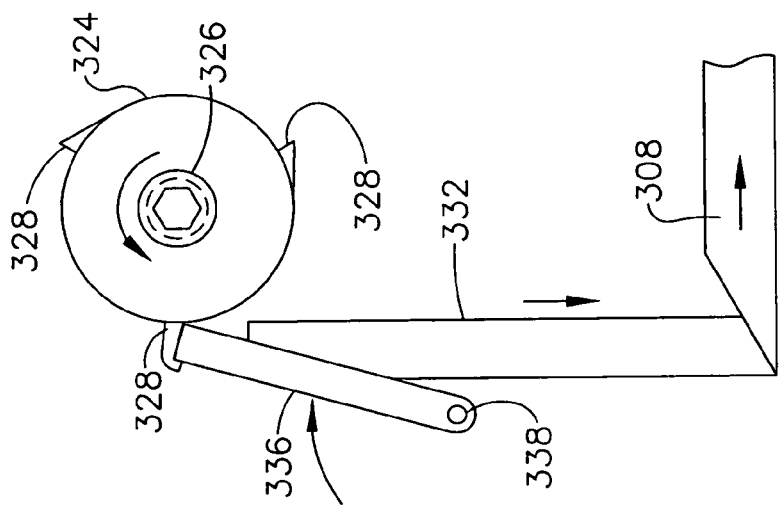
Figure 54:
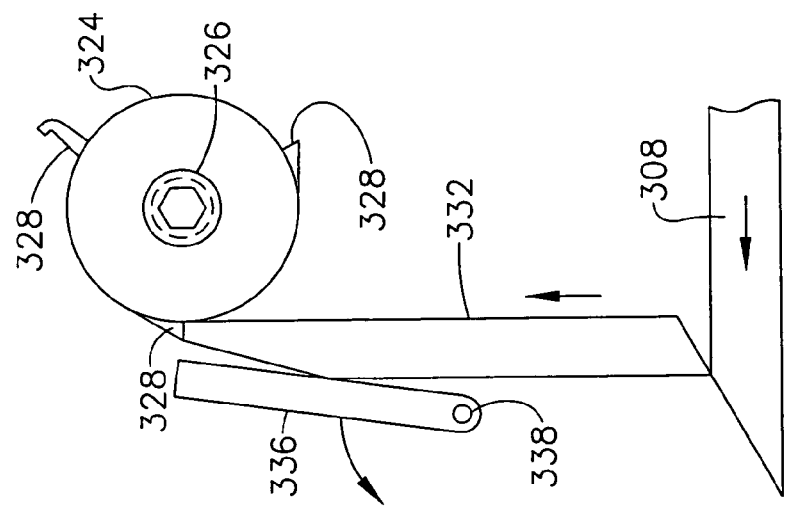

At this point, the counter 318 has advanced one position, and the primary portion 302 is able to be reattached to the grip portion 304 (or attached to a replacement grip section). The attachment/disconnect cycle may be repeated. When the grip portion 304 is fully engaged with the primary portion 302, the blocking member 332 is in contact with the protrusion 328 that was previously in contact with the gate member 336, thereby preventing the index wheel 324 from advancing as shown in FIG. 54. At the end of the second cycle, when the grip portion 304 is disconnected from the primary portion 302, the gate member 336 is in contact with a third protrusion 328 as shown in FIG. 55. The third protrusion 328 is structured and arranged to prevent the gate member 336 from being advanced away from the index wheel 324 by the blocking member 332, thereby preventing the primary portion 302 from being reattached to the grip portion 304 (or attached to a replacement grip section). Therefore, according to these embodiments, the surgical instrument 10 is effectively a two-use instrument. However, one skilled in the art will appreciate that the number of uses can be increased if the index wheel 324 defines additional protrusions 328 or indents.

FIG. 56 illustrates various embodiments of a surgical instrument 400. The surgical instrument 400 may be similar to surgical instrument 300, but does not include the lockout system 316. Surgical instrument 400 is also different in that a portion 402 of the grip portion 304 is structured and arranged to break off of the grip portion 304 and remain in contact with the primary portion 302 when the grip portion 304 is disconnected from the primary portion 302. After separation from the grip portion 304, the breakoff portion 402 remains in contact with the primary portion 302 and operates to physically block reattachment of the grip portion 304 (or attachment of a replacement grip portion) to the primary portion 302. Therefore, the surgical instrument 400 is effectively a single-use instrument. Although the breakoff portion 402 is shown in FIG. 56 as being a portion of the first upper slide rail 306, according to other embodiments the breakoff portion 402 may be any portion of the grip portion 304.

FIG. 57 illustrates various embodiments of surgical instrument 500. The surgical instrument 500 may be similar to surgical instrument 300, but does not include the lockout system 316. Rather, surgical instrument 500 comprises a counter 502 within the handle 6, wherein the counter 502 is structured and arranged to open a motor interlock 504. As shown in FIG. 58, the motor interlock 504 is in the electrical communication path between the battery 64 and the motor 65. The circuit shown in FIG. 58 is similar to the circuit shown in FIG. 11, but includes the motor interlock 504 connected in series with the cartridge lockout sensor 136. Therefore, when the motor interlock 504 is in the open position, the relay 138 is placed into a non-energized state, thereby preventing the battery 64 from powering the motor 65.

According to various embodiments, the motor interlock 504 comprises a portion of the counter 502. The counter 502 may be embodied as a mechanical counter, an electro-mechanical counter, or an electrical counter structured and arranged to open the motor interlock 504 after the counter 502 reaches a predetermined count. According to various embodiments, the input to the counter 502 may be a non-electrical input. According to other embodiments, the counter 502 may comprise an integrated circuit chip that includes one or more motor interlocks 504. Although only one motor interlock 504 is shown in FIG. 58, it is understood that there may be any number of motor interlocks 504 in the electrical communication path between the battery 64 and the motor 65.

According to various embodiments, the counter 502 is structured and arranged to open the motor interlock 504 after the battery 64 is removed from the surgical instrument 500 a predetermined number of times. The predetermined number of times may be any number of times. For example, according to various embodiments, the counter 502 may open the motor interlock 504 after the battery 64 is removed from the instrument 500 two times.

According to other embodiments, the counter 502 is structured and arranged to open the motor interlock 504 after the grip portion 304 is disconnected from the primary portion 302 a predetermined number of times. The predetermined number of times may be any number of times. For example, according to various embodiments, the counter 502 may open the motor interlock 504 after the grip portion 304 is disconnected from the primary portion 302 two times.

According to other embodiments, the counter 502 is structured and arranged to open the motor interlock 504 after the closure trigger 18 and/or the firing trigger 20 is actuated a predetermined number of times. The predetermined number of times may be any number of times. For example, according to various embodiments, the counter 502 may open the motor interlock 504 after the firing trigger 20 is actuated twelve times.

According to other embodiments, the counter 502 is structured and arranged to open the motor interlock 504 a predetermined amount of time after a first use of the surgical instrument 500. For such embodiments, the counter 502 may be embodied as a timer. The first use may be defined in any manner corresponding to the use of the surgical instrument 500. For example, the first use may correspond to attachment of the grip portion 304 to the primary portion 302, actuation of the closure trigger 18, actuation of the firing trigger 20, etc. The predetermined amount of time may be any amount of time.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
a handle comprising:
a primary portion; and a grip portion releasably connected to the primary portion;

a battery within the grip portion;

a motor in electrical communication with the battery;

a lockout system within the handle, the lockout system comprising a counter to advance when the grip portion is disconnected from the primary portion, wherein the lockout system blocks the grip portion from connecting to the primary portion after the counter has advanced a predetermined number of times;

an index wheel; and a biasing member coupled to the index wheel.

2. The surgical instrument of claim 1, wherein the battery is removable from the grip portion.

3. The surgical instrument of claim 1, wherein the battery is a rechargeable battery.

4. The surgical instrument of claim 1, wherein the lockout system further comprises a blocking assembly coupled to the counter, wherein the blocking assembly blocks connection of the grip portion to the primary portion after the counter has advanced the predetermined number of times.

5. The surgical instrument of claim 4, wherein the blocking assembly comprises a blocking member blocks connection of the grip portion to the primary portion after the counter has advanced the predetermined number of times.

6. The surgical instrument of claim 5, wherein the blocking assembly further comprises a gate member in contact with the blocking member.

7. The surgical instrument of claim 6, wherein the blocking assembly further comprises a biasing member coupled to the gate member.

8. The surgical instrument of claim 1, wherein the counter is a resettable counter.

9. The surgical instrument of claim 1, wherein the lockout system blocks the grip portion from physically connecting to the primary portion after the counter has advanced a predetermined number of times.

10. The surgical instrument of claim 1, wherein the lockout system blocks the grip portion from electrically connecting to the primary portion after the counter has advanced a predetermined number of times.

* * * * *